US010092526B2

(12) United States Patent
Chen et al.

(10) Patent No.: US 10,092,526 B2
(45) Date of Patent: *Oct. 9, 2018

(54) COMPOSITIONS AND METHODS FOR TREATING RESPIRATORY INJURY OR DISEASE

(71) Applicants: University of Pittsburgh—Of the Commonwealth System of Higher Education, Pittsburgh, PA (US); The United States of America as represented by the Department of Veterans Affairs, Washington, DC (US)

(72) Inventors: Beibei Chen, Wexford, PA (US); Rama Mallampalli, Sewickley, PA (US)

(73) Assignees: University of Pittsburgh—Of the Commonwealth System of Higher Education, Pittsburgh, PA (US); The United States of America as represented by the Department of Veterans Affairs, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/816,963

(22) Filed: Nov. 17, 2017

(65) Prior Publication Data

US 2018/0071232 A1    Mar. 15, 2018

Related U.S. Application Data

(63) Continuation of application No. 15/102,827, filed as application No. PCT/US2014/069368 on Dec. 9, 2014, now Pat. No. 9,849,098.

(Continued)

(51) Int. Cl.
| | |
|---|---|
| *A01N 43/54* | (2006.01) |
| *A61K 31/135* | (2006.01) |
| *A61K 31/137* | (2006.01) |
| *C07D 401/12* | (2006.01) |
| *C07D 409/12* | (2006.01) |
| *A61K 9/00* | (2006.01) |
| *A61K 31/341* | (2006.01) |
| *A61K 31/381* | (2006.01) |
| *A61K 31/4025* | (2006.01) |

(Continued)

(52) U.S. Cl.
CPC ............ *A61K 31/137* (2013.01); *A61K 9/007* (2013.01); *A61K 31/341* (2013.01); *A61K 31/381* (2013.01); *A61K 31/4025* (2013.01); *A61K 31/4155* (2013.01); *A61K 31/4178* (2013.01); *A61K 31/427* (2013.01); *A61K 31/444* (2013.01); *A61K 31/4545* (2013.01); *A61K 31/506* (2013.01); *A61K 31/5377* (2013.01); *A61K 45/06* (2013.01); *C07C 211/27* (2013.01); *C07D 295/135* (2013.01); *C07D 401/12* (2013.01); *C07D 403/12* (2013.01); *C07D 407/12* (2013.01); *C07D 409/12* (2013.01); *C07D 417/12* (2013.01)

(58) Field of Classification Search
CPC ...................................................... C07D 239/42
USPC .................................................. 514/256, 649
See application file for complete search history.

(56) References Cited

U.S. PATENT DOCUMENTS

| | | |
|---|---|---|
| 4,010,282 A | 3/1977 | Binning et al. |
| 9,359,284 B2 | 6/2016 | Chen et al. |

(Continued)

FOREIGN PATENT DOCUMENTS

| | | |
|---|---|---|
| EP | 1127883 | 6/2005 |
| JP | 20011278869 | 10/2001 |

(Continued)

OTHER PUBLICATIONS

Albano, et al., "Novel chiral diamino-oligothiophenes as valuable ligands in Pd-catalyzed allylic alkylations. On the primary role of secondary interactions in asymmetric catalysis," *Advanced Synthesis & Catalysis*, vol. 347, 1507-1512, Oct. 19, 2005.

Caterina et al. "Imidazolidines are new anti-Trypanosoma cruzi agents: Biological evaluation and structure-activity relationships", *Bioorganic & Medicinal Chemistry*, 16: 2226-2234, 2008.

Chen et al., "A combinatorial F box protein directed pathway controls TRAF adaptor stability to regulate inflammation," *Nature Immunology*, 14(5): 470-479, May 2013.

(Continued)

*Primary Examiner* — Raymond J Henley, III
(74) *Attorney, Agent, or Firm* — Klarquist Sparkman, LLP

(57) ABSTRACT

A method for treating a respiratory injury or disease comprising: administering to a patient in need of treatment a pharmaceutical composition comprising a compound of general Formula I:

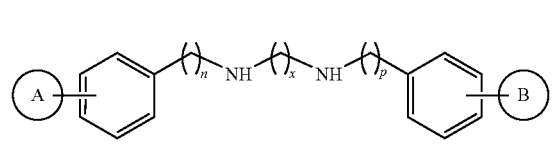

or salt, ester, solvate, hydrate, or prodrug thereof;
wherein:
x is an integer from 1 to 10;
A and B are each, independently, $C_{3-7}$cycloalkyl, $C_{3-7}$cycloalkyl-$C_{1-6}$alkyl, $C_{3-7}$heterocycloalkyl, $C_{3-7}$heterocycloalkyl-$C_{1-6}$alkyl, $C_{6-10}$aryl, $C_{6-10}$aryl-$C_{1-6}$alkyl, $C_{3-9}$heteroaryl, or $C_{3-9}$heteroaryl-$C_{1-6}$alkyl; and
n and p are each, independently, integers from 1 to 10; and
a pharmaceutically acceptable carrier, excipient, or diluent.

21 Claims, 20 Drawing Sheets

Related U.S. Application Data

(60) Provisional application No. 61/913,849, filed on Dec. 9, 2013, provisional application No. 61/913,853, filed on Dec. 9, 2013, provisional application No. 61/914,278, filed on Dec. 10, 2013, provisional application No. 61/914,287, filed on Dec. 10, 2013.

(51) Int. Cl.

| | |
|---|---|
| *A61K 31/4155* | (2006.01) |
| *A61K 31/4178* | (2006.01) |
| *A61K 31/427* | (2006.01) |
| *A61K 31/444* | (2006.01) |
| *A61K 31/4545* | (2006.01) |
| *A61K 31/506* | (2006.01) |
| *A61K 31/5377* | (2006.01) |
| *C07C 211/27* | (2006.01) |
| *C07D 295/135* | (2006.01) |
| *C07D 417/12* | (2006.01) |
| *C07D 407/12* | (2006.01) |
| *C07D 403/12* | (2006.01) |
| *A61K 45/06* | (2006.01) |

(56) References Cited

U.S. PATENT DOCUMENTS

| | | |
|---|---|---|
| 2003/0013772 A1 | 1/2003 | Murphy et al. |
| 2006/0148904 A1 | 7/2006 | Protopopova et al. |
| 2015/0152041 A1 | 6/2015 | Chen et al. |

FOREIGN PATENT DOCUMENTS

| | | |
|---|---|---|
| WO | WO 1999/024395 | 5/1999 |
| WO | WO 01/72685 | 10/2001 |
| WO | WO 03/096989 | 11/2003 |
| WO | WO 2008/142623 | 11/2008 |
| WO | WO 2013/184202 | 12/2013 |

OTHER PUBLICATIONS

Chen et al., "Calmodulin Antagonizes a Calcium-Activated SCF Ubiquitin E3 Ligase Subunit, FBXL2, to Regulate Surfactant Homeostasis," *Molecular and Cellular Biology*, 31(9): 1905-1920, May 1, 2011.

Grabenko et al., "Synthesis and study of p-substituted toluoyl derivatives of ethylenediamine and piperzine," *Ukrainskii Khimicheskii Zhurnal*, 47(9): 956-959, 1981 (English translation).

Huang et al., "Syntheses, crystal structures and properties of silver (I) and copper (II) complexes with an oxazoline-containing tetradentate ligand," *New Journal of Chemistry*, No. 34, pp. 2436-2444, Jun. 3, 2010.

International Search Report and Written Opinion from International application No. PCT/US2013/030995, dated Jun. 13, 2013.

International Search Report and Written Opinion from International application No. PCT/US2014/069368, dated Mar. 17, 2015.

Kauffman, et al., "A heterocyclohexaaromatic compound with 'face-to-face' arrangement of two benzene rings," *Angewandte Chemie*, 90(10): 804-805, 1978. (English abstract only).

Khan et al., "Synthesis, anti-inflammatory and analgesic activity of new hexahydro-pyrimidine derivatives", *Pharmazie*, 57:377-383, 2002.

Kraml et al., "Agents Affecting Lipid Metabolism. VIII. N,N'-Dibenzylethylenediamine, the Key to a Novel Class of Cholesterol Biosynthesis Inhibitors," *J. Med. Chem.*, vol. 7, pp. 500-503, Feb. 4, 1964.

Lakatos et al., "Two pyridine derivatives as potential Cu(II) and Zn(II) chelators in therapy for Alzheimer's disease," *The International Journal for Inorganic, Organometallic and Bioinorganic Chemistry*, vol. 39, 1302-1315, Jan. 1, 2010.

Lakatos et al., "Two pyridine derivatives as potential Cu(II) and Zn(II) chelators in therapy for Alzheimer's disease," *Dalton Transctions*, vol. 39, pp. 1302-1315, 2010.

Lexy et al, "Heterocyclopolyaromatics. X. The first cyclohexaaromatic compound with 'face-to-face' arrangement of two aromatic ring members," *Chemiste Berichte*, 113(8): 2749-2754, 1980. (English abstract only).

Mallamapalli et al., "Targeting F box protein FBXO3 to control cytokine-driven inflammation," *The Journal of Immunology*, 191(10): 5247-5255, Oct. 11, 2013.

Newman et al., "Chiral metal complexes. Part 33. Coordination stereoselectivity in ternary cobalt(III) complexes of dipeptides and an optically active triamine," *Inorganica Chimica Acta*, vol. 183, pp. 145-155, 1991.

PubChem, SID 103190923, Dec. 22, 2010, http://pubchem.ncbi.nlm.nih.gov/substance/103190923.

PubChem, SID 103191203, Dec. 22, 2010, http://pubchem.ncbi.nlm.nih.gov/substance/103191203.

Sharma et al., "Synthesis, antimicrobial activity and structure-activity relationship study of N, N-dibenzyl-cyclohexane-1,2-diamine derivatives", *European Journal of Medicinal Chemistry*, 46:480-487, 2011.

Sundravel et al., "Synthesis, structure, spectra and reactivity of iron(III) complexes of facially coordinating and sterically hindering 3N ligands as models for catechol dioxygenases," *Dalton Transactions*, pp. 7012-7025, 2008.

U.S. Appl. No. 15/138,120, filed Apr. 25, 2016.

U.S. Appl. No. 15/138,137, filed Apr. 25, 2016.

Written Opinion issued for International Application No. PCT/US2014/069368 dated Mar. 17, 2015, 13 pages.

Yigit, "The Synthesis of Some Perhydrobenzimidazolinium Salts and Their Application in Pd-Carbene Catyalyzed Heck and Suzuki Reactions," *Molecules*, vol. 14, pp. 2032-2042, 2009.

PA103 + Vehicle

PA103 + Com. 005

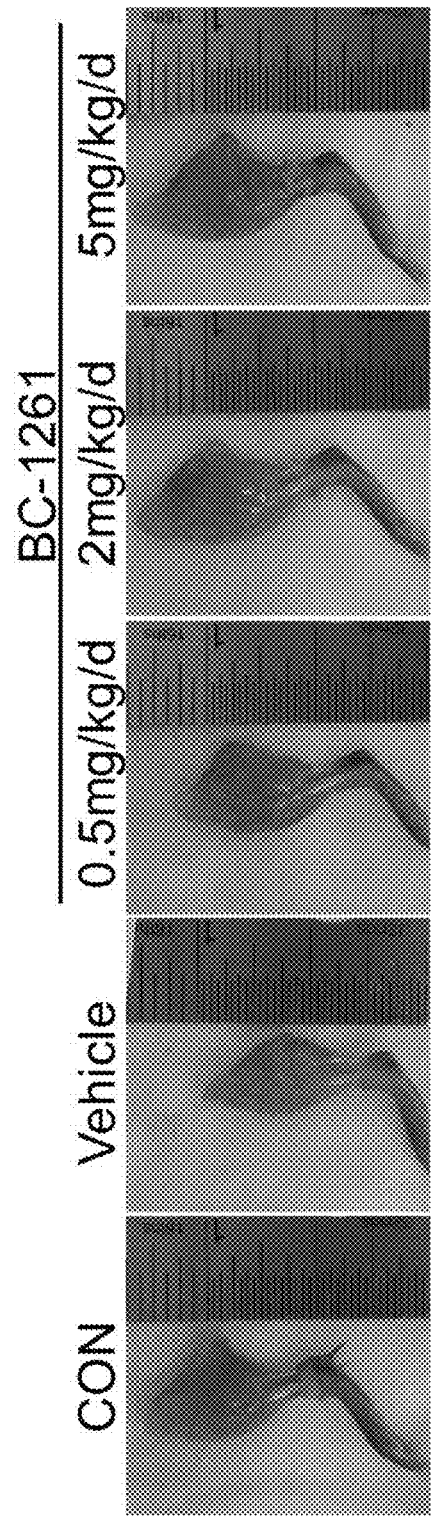
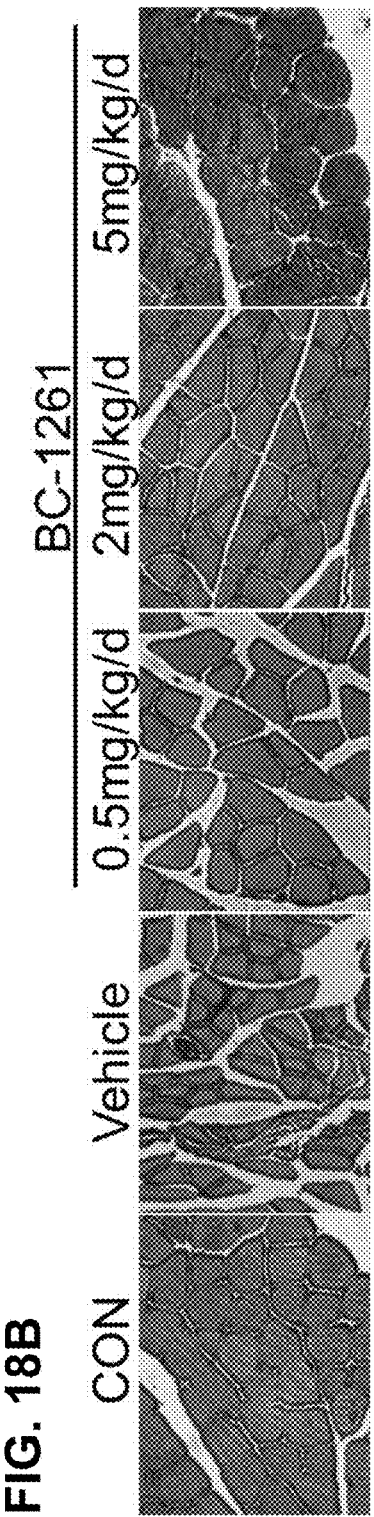
FIG. 18A
FIG. 18B

COMPOSITIONS AND METHODS FOR TREATING RESPIRATORY INJURY OR DISEASE

CROSS REFERENCE TO RELATED APPLICATIONS

This application is a continuation of U.S. application Ser. No. 15/102,827, filed Jun. 8, 2016, now U.S. Pat. No. 9,849,098, which is the U.S. National Stage of International Application No. PCT/US2014/069368, filed Dec. 9, 2014, which was published in English under PCT Article 21(2), which in turn claims the benefit of U.S. Provisional Appl. 61/913,849, filed Dec. 9, 2013, U.S. Provisional Appl. 61/913,853, filed Dec. 9, 2013, U.S. Provisional Appl. No. 61/914,278, filed Dec. 10, 2013, and U.S. Provisional Appl. 61/914,287, filed Dec. 10, 2013, all of which are incorporated herein by reference.

ACKNOWLEDGMENT OF GOVERNMENT SUPPORT

This invention was made with government support under grants HL068135, HL081784, HL096376, HL097376, and HL098174 awarded by the National Institutes of Health. The government has certain rights in the invention.

BACKGROUND

Secretion of pro-inflammatory cytokines after infection with virulent pathogens, in response to host cell injury, or related irritants that activate receptors on immune effector cells (T-cells, macrophages, etc.) underlies numerous diseases including various respiratory diseases. For example, acute and chronic bronchitis, emphysema, respiratory infections (pneumonia, pleurisy), flu (including influenza), post-lung transplant rejection including acute and chronic rejection and bronchiolitis obliterans, acute lung injury or the acute respiratory distress syndrome, pulmonary fibrosis, asthma, cystic fibrosis, and bronchiectasis are all linked to activation of injurious cytokines. Efforts to block cytokine release and circulation have focused on administration of systemic corticosteroids or targeted anti-inflammatory agents to specific cytokines such as TNFα and IL-1β.

TNF receptor associated factors (TRAFs) are a family of proteins primarily involved in the regulation of inflammation, antiviral responses, and apoptosis. Six well-characterized TRAF proteins ($TRAF_{1-6}$) exist and a newer homologue TRAF7 was recently identified. All TRAF members share a highly conserved C-terminal domain that mediates interactions with transmembrane TNF receptors. Identification of TRAF proteins has contributed significantly to the elucidation of the molecular mechanisms of signal transduction emanating from the TNFR superfamily and the Toll like/interleukin-1 receptor (TLR/IL-1R) family TRAF family proteins interact with the IL-1 receptor, TLRs, CD40, RANK, I-TAC, p75 NGF receptor, etc. Specifically, TRAF2, TRAF5, and TRAF6 serve as adapter proteins that link cell surface receptors with downstream kinase cascades, which in turn activate key transcription factors, such as nuclear factor kB (NFkB), resulting in cytokine gene expression. With an exaggerated immune response, TRAF-mediated cytokine release leads to profound effects of edema, multi-organ failure and shock. The TRAF proteins, however, have a central role as they mediate signal transduction to elicit transcriptional activation of several downstream cytokines. These findings suggest that maneuvers designed to selectively modulate the abundance of TRAF proteins might serve as a novel strategy for therapeutic intervention. However, to date, very little is known regarding the molecular regulation of the TRAF family at the level of protein stability. Strategies directed at modulation of TRAF protein concentrations in cells might serve as the basis for the design of a new class of anti-inflammatory agents.

Ubiquitination of proteins brands them for degradation, either by the proteasome or via the lysosome, and regulates diverse processes. The conjugation of ubiquitin to a target protein is orchestrated by a series of enzymatic reactions involving an E1 ubiquitin-activating enzyme, ubiquitin transfer from an E1-activating enzyme to an E2-conjugating enzyme, and last, generation of an isopeptide bond between the substrate's e-amino lysine and the c-terminus of ubiquitin catalyzed by a E3-ubiquitin ligase. Of the many E3 ligases, the Skp-Cullinl-F box (SCF) superfamily is among the most studied. The SCF complex has a catalytic core complex consisting of Skpl, Cullinl, and the E2 ubiquitin-conjugating (Ubc) enzyme. The SCF complex also contains an adaptor receptor subunit, termed F-box protein, that targets hundreds of substrates through phosphospecific domain interactions. F-box proteins have two domains: an NH2-terminal F-box motif and a C-terminal leucine-rich repeat (LRR) motif or WD repeat motif. The SCF complex uses the F-box motif to bind Skpl, whereas the leucine-rich/WD repeat motif is used for substrate recognition.

Ubiquitin E3 ligase subunit, FBXO3, has been found to be sufficient to ubiquitinate and mediate proteasomal degradation of another relatively recently-identified ubiquitin E3 ligase subunit, FBXL2. Further, FBXL2 appears to act as a "break" on inflammation, by targeting the TRAF family of proteins for their disposal in epithelia and monocytes. Thus, activation of FBXO3 results in FBXL2 ubiquitination and degradation increasing immunoreactive TRAFs and cytokine production, and impairing lung function. Bronchitis and other respiratory diseases and respiratory injury cause increased FBXO3 activity. Therefore, small molecule inhibitors of FBXO3 function may be useful in the prophylaxis and treatment of these respiratory diseases and injuries.

SUMMARY

Various embodiments of the invention are directed to compounds of general Formula I:

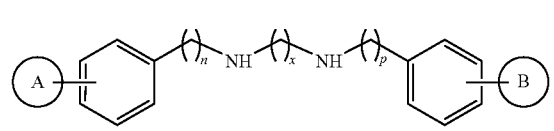

or salts, esters, solvates, hydrates, or prodrugs thereof; wherein x is an integer from 1 to 10; A and B are each, independently, $C_{3-7}$cycloalkyl, $C_{3-7}$cycloalkyl-$C_{1-6}$alkyl, $C_{3-7}$heterocycloalkyl, $C_{3-7}$heterocycloalkyl-$C_{1-6}$alkyl, $C_{6-10}$aryl, $C_{6-10}$aryl-$C_{1-6}$alkyl, $C_{3-9}$heteroaryl, or $C_{3-9}$heteroaryl-$C_{1-6}$alkyl; and n and p are each, independently, integers from 1 to 10.

In some embodiments, at least one of A and B can be substituted with at least one substituent independently selected from halogen, $C_{1-6}$alkyl, $C_{1-6}$haloalkyl, hydroxyl, $C_{1-6}$alkoxy, $C_{1-6}$haloalkoxy, amino, $C_{1-6}$alkylamino, or di-$C_{1-6}$alkylamino. In particular embodiments, A and B are the same, and in some embodiments, A and B are in para configuration. In certain embodiments, A and B may each, independently, be selected from cyclohexyl, phenyl, 6-membered heteroaryl, 6-membered heterocycloalkyl, cyclopentyl, cyclopentene, cyclopentadiene, 5-membered heteroaryl, or 5-membered heterocycloalkyl. In some embodiments, A and B may each, independently, be selected from pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, pyranyl, thiopyranyl, piperidinyl, morpholinyl, thiomorpholinyl, piperazinyl, or triazinyl, and in other embodiments, A and B may each, independently, be selected from imidazolyl, pyridyl, pyrazolyl, oxadiazolyl and pyrimidinyl. In further embodiments, A and B may each, independently, be selected from:

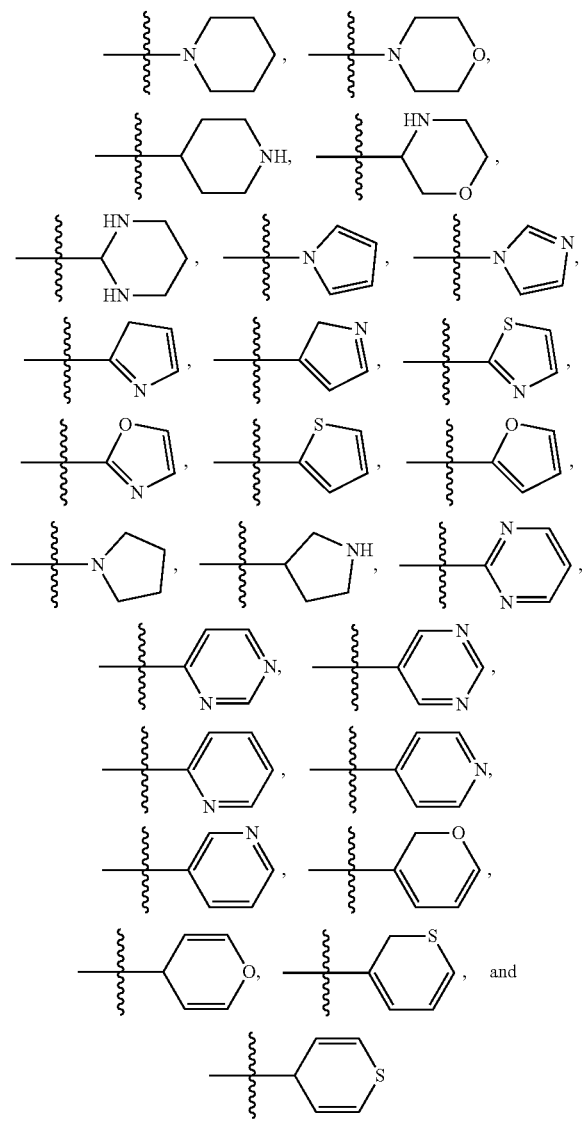

Particular embodiments are directed to compounds of Formula Ia:

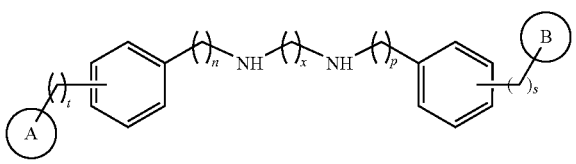

or salts, esters, solvates, hydrates, or prodrugs thereof; wherein x is an integer from 1 to 10; A and B are each, independently, $C_{3-7}$cycloalkyl, $C_{3-7}$cycloalkyl-$C_{1-6}$alkyl, $C_{3-7}$heterocycloalkyl, $C_{3-7}$heterocycloalkyl-$C_{1-6}$alkyl, $C_{6-10}$aryl, $C_{6-10}$aryl-$C_{1-6}$alkyl, $C_{3-9}$heteroaryl, or $C_{3-9}$heteroaryl-$C_{1-6}$alkyl; n and p are each, independently, integers from 1 to 10; and s and t are each, independently, integers from 1 to 5.

In some embodiments, at least one of A and B can be substituted with at least one substituent independently selected from halogen, $C_{1-6}$alkyl, $C_{1-6}$haloalkyl, hydroxyl, $C_{1-6}$alkoxy, $C_{1-6}$ haloalkoxy, amino, $C_{1-6}$alkylamino, or di-$C_{1-6}$alkylamino. In particular embodiments, A and B are the same, and in some embodiments, A and B are in para configuration. In certain embodiments, A and B may each, independently, be selected from cyclohexyl, phenyl, 6-membered heteroaryl, 6-membered heterocycloalkyl, cyclopentyl, cyclopentene, cyclopentadiene, 5-membered heteroaryl, or 5-membered heterocycloalkyl. In some embodiments, A and B may each, independently, be selected from pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, pyranyl, thiopyranyl, piperidinyl, morpholinyl, thiomorpholinyl, piperazinyl, or triazinyl, and in other embodiments, A and B may each, independently, be selected from imidazolyl, pyridyl, pyrazolyl, oxadiazolyl or pyrimidinyl. In further embodiments, A and B may each, independently, be selected from:

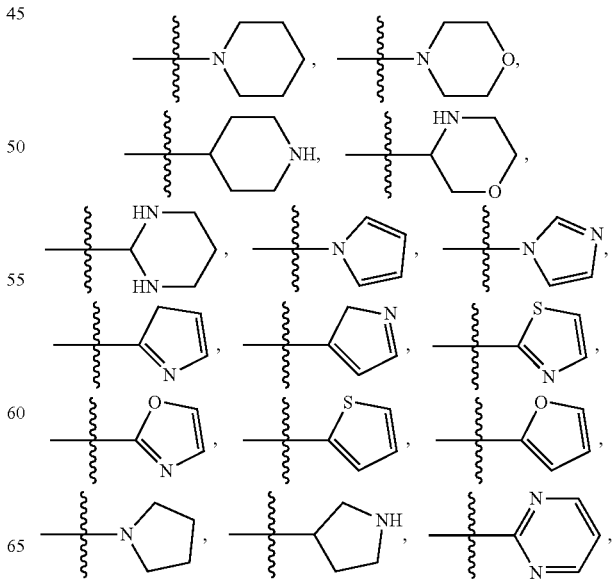

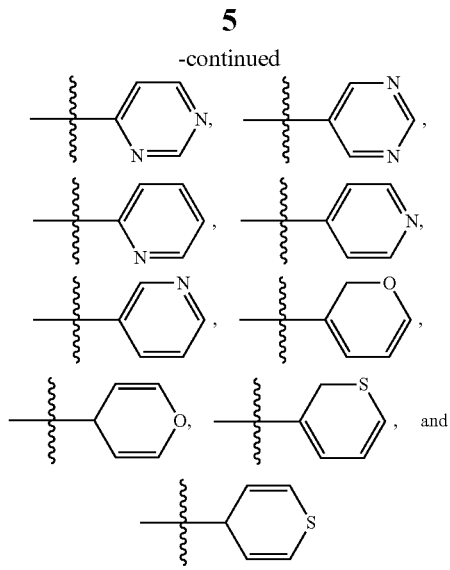

Other embodiments are directed to pharmaceutical compositions including compounds of general Formula I:

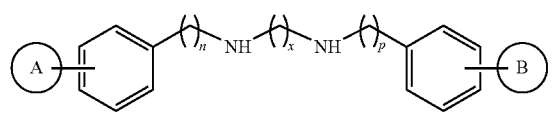

I or salts, esters, solvates, hydrates, or prodrugs thereof; wherein x is an integer from 1 to 10; A and B are each, independently, $C_{3-7}$cycloalkyl, $C_{3-7}$cycloalkyl-$C_{1-6}$alkyl, $C_{3-7}$heterocycloalkyl, $C_{3-7}$heterocycloalkyl-$C_{1-6}$alkyl, $C_{6-10}$aryl, $C_{6-10}$aryl-$C_{1-6}$alkyl, $C_{3-9}$heteroaryl, or $C_{3-9}$heteroaryl-$C_{1-6}$alkyl; and n and p are each, independently, integers from 1 to 10; and a pharmaceutically acceptable carrier, excipient, or diluent.

In some embodiments, at least one of A and B can be substituted with at least one substituent independently selected from halogen, $C_{1-6}$alkyl, $C_{1-6}$haloalkyl, hydroxyl, $C_{1-6}$alkoxy, $C_{1-6}$haloalkoxy, amino, $C_{1-6}$alkylamino, or di-$C_{1-6}$alkylamino In particular embodiments, A and B are the same, and in some embodiments, A and B are in para configuration. In certain embodiments, A and B may each, independently, be selected from cyclohexyl, phenyl, 6-membered heteroaryl, 6-membered heterocycloalkyl, cyclopentyl, cyclopentene, cyclopentadiene, 5-membered heteroaryl, or 5-membered heterocycloalkyl. In some embodiments, A and B may each, independently, be selected from pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, pyranyl, thiopyranyl, piperidinyl, morpholinyl, thiomorpholinyl, piperazinyl, or triazinyl, and in other embodiments, A and B may each, independently, be selected from imidazolyl, pyridyl, pyrazolyl, oxadiazolyl or pyrimidinyl. In further embodiments, A and B may each, independently, be selected from:

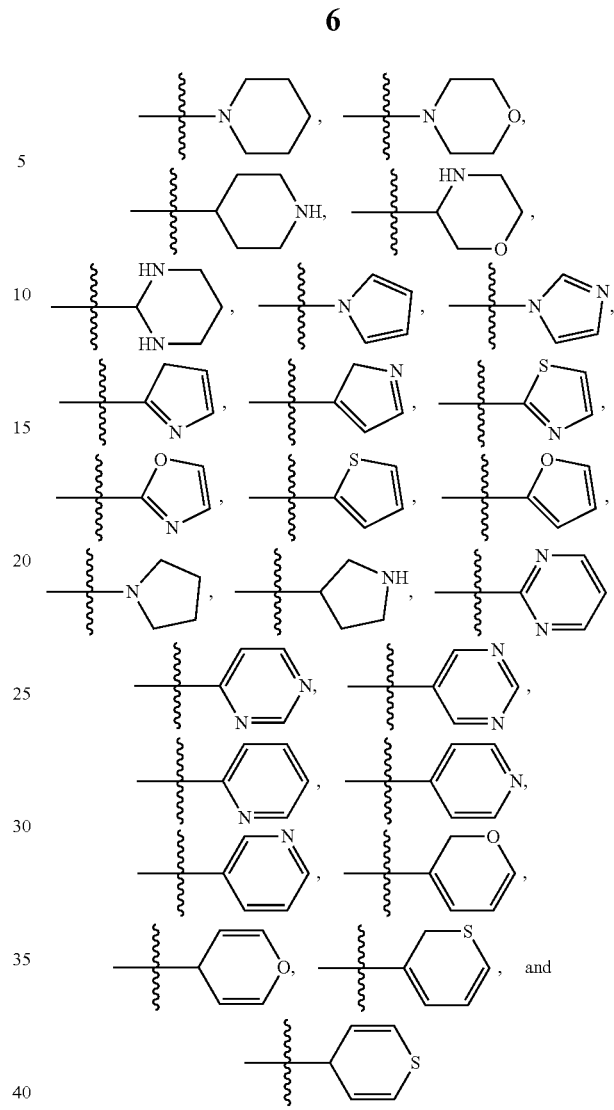

Also disclosed herein in one embodiment are methods using FBXO3 inhibitors. Illustrative FBXO3 inhibitors include benzathine compounds, optionally-substituted diaminoalkanes (e.g., 1,10-diaminodecane), substituted quinolines (e.g., quinidine, hydroxychloroquine, primaquine), haematoxylin, tetramethylenebis, naphthacaine, ampicillin, and elliptine, and pharmaceutically acceptable salts and esters thereof.

The benzathine compound may be benzathine or a benzathine analog. In certain embodiments the benzathine compound is not benzathine penicillin In certain embodiments the benzathine analog includes a divalent diamine core moiety, a first aryl-containing moiety at a first terminal end of the divalent diamine core moiety, and a second aryl-containing moiety at a second terminal end of the divalent diamine core moiety. Each amino groups of the diamine group may be individually —NH— or —NR—, wherein R is a substituted group as described such as a lower alkyl, alkoxy, hydroxy, acyl, acyloxy, alkoxycarbonyl, aryl, carboxyl, or ester. The divalent diamine core moiety may include an optionally-substituted alkanediyl, an optionally-substituted cycloalkanediyl, an optionally-substituted aryldiyl, or an optionally-substituted alkanearyldiyl positioned between the two amino groups. In certain embodiments the two amino groups of the diamine may together with carbon atoms form a heteroaryldiyl group. The terminal aryl-containing groups may each individually be an aralkyl group (preferably a benzyl group) or an N-heteroaralkyl group such as -alkyl-pyrazinyl, -alkyl-pyrimidinyl, -alkyl-pyridazinyl, or -alkyl-pyridinyl. The aryl ring of the aralkyl group may be substituted with an optionally-substituted N-heterocyclic group. In certain embodiments, the optionally-substituted N-heterocyclic group is located at a ring position para to the point of attachment of the aralkyl group to the divalent diamine core moiety.

Illustrative benzathine analogs include optionally-substituted N-heterocyclic-substituted benzathines. In certain embodiments, the benzathine analogs include two phenyl rings, wherein at least one, and preferably both, of the phenyl rings are substituted with an optionally-substituted N-heterocyclic group, which optionally-substituted N-heterocyclic may be the same or different. In certain embodiments, the optionally-substituted N-heterocyclic group is located at a ring position para to the point of attachment of the phenyl ring to the benzathine molecular scaffold.

Illustrative N-heterocyclic groups include, for example, pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, piperidinyl, morpholinyl, thiomorpholinyl, piperazinyl, and triazinyl. Particularly preferred N-heterocyclic groups include imidazolyl, pyridyl, pyrazolyl, oxadiazolyl and pyrimidinyl.

The benzathine analogs, or pharmaceutically acceptable salts or esters thereof, may have structure of formula V:

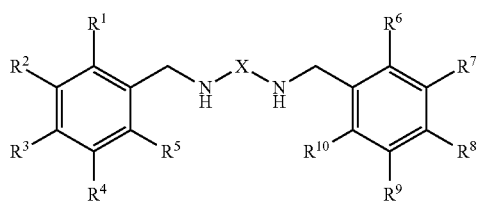

wherein X is a divalent or tetravalent linking moiety; and $R^1$-$R^{10}$ are each individually H, optionally-substituted alkyl, optionally-substituted alkoxy, optionally-substituted aryl, optionally-substituted cycloalkyl, optionally-substituted heterocyclic, halogen, amino, or hydroxy.

In various embodiments, the carrier for the pharmaceutical compositions may be selected from water, ethanol, polyol, glycerol, propylene glycol, liquid polyethylene glycol, vegetable oils, nut oils, and mixtures thereof. In some embodiments, the pharmaceutical composition may further include, for example, at least one flavoring agent, binding agent, lubricant, disintegrant, surface modifying agent, surfactant, suspending agent, stabilizing agent, fillers, glidant, compression aid, disintegrating agent, encapsulating material, or combinations thereof. In certain embodiments, the pharmaceutical compositions may further include at least one anti-inflammatory agents, antimicrobial agents, matrix metalloprotease inhibitors, lipoxygenase inhibitors, cytokine antagonists, immunosuppressants, anti-cancer agents, anti-viral agents, cytokines, growth factors, immunomodulators, prostaglandins, anti-vascular hyperproliferation compounds, and combinations thereof. In various embodiments, the pharmaceutical composition is in unit dose form. In some embodiments, the compound of Formula I or salt, ester, solvate, hydrate, or prodrug thereof may be about 15 wt. % to about 95 wt. % of a total weight of the pharmaceutical composition, and in certain embodiments, each unit dose may include about 0.5 mg to about 500 mg of the compound of Formula I or salt, ester, solvate, hydrate, or prodrug thereof.

Further embodiments are directed to methods for treating a respiratory injury or disease including the steps of administering to a patient in need of treatment a pharmaceutical composition comprising a compound of general Formula I:

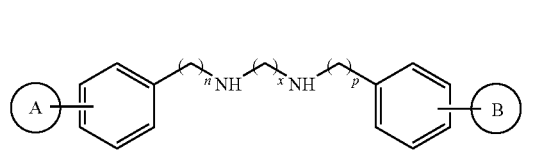

or salt, ester, solvate, hydrate, or prodrug thereof; wherein x is an integer from 1 to 10; A and B are each, independently, $C_{3-7}$cycloalkyl, $C_{3-7}$cycloalkyl-$C_{1-6}$alkyl, $C_{3-7}$heterocycloalkyl, $C_{3-7}$heterocycloalkyl-$C_{1-6}$alkyl, $C_{6-10}$arkyl, $C_{6-10}$aryl-$C_{1-6}$alkyl, $C_{3-9}$heteroaryl, or $C_{3-9}$heteroaryl-$C_{1-6}$alkyl; and n and p are each, independently, integers from 1 to 10; and a pharmaceutically acceptable carrier, excipient, or diluent.

In some embodiments, at least one of A and B can be substituted with at least one substituent independently selected from halogen, $C_{1-6}$alkyl, $C_{1-6}$haloalkyl, hydroxyl, $C_{1-6}$alkoxy, $C_{1-6}$haloalkoxy, amino, $C_{1-6}$alkylamino, or di-$C_{1-6}$alkylamino. In particular embodiments, A and B are the same, and in some embodiments, A and B are in para configuration. In certain embodiments, A and B may each, independently, be selected from cyclohexyl, phenyl, 6-membered heteroaryl, 6-membered heterocycloalkyl, cyclopentyl, cyclopentene, cyclopentadiene, 5-membered heteroaryl, or 5-membered heterocycloalkyl. In some embodiments, A and B may each, independently, be selected from pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, pyranyl, thiopyranyl, piperidinyl, morpholinyl, thiomorpholinyl, piperazinyl, or triazinyl, and in other embodiments, A and B may each, independently, be selected from imidazolyl, pyridyl, pyrazolyl, oxadiazolyl or pyrimidinyl. In further embodiments, A and B may each, independently, be selected from:

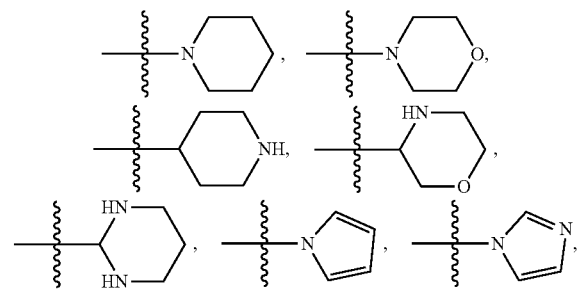

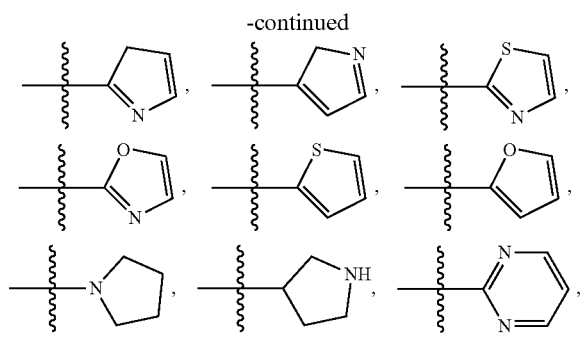

In various embodiments, the compound of Formula I or salt, ester, solvate, hydrate, or prodrug thereof may be administered in an effective amount. In some embodiments, an effective amount may be from about 0.5 mg to about 500 mg of the compound of Formula I or salt, ester, solvate, hydrate, or prodrug thereof, and in certain embodiments, an effective amount comprises about 0.5 mg/kg to about 500 mg/kg per kg of patient body weight of the compound of Formula I or salt, ester, solvate, hydrate, or prodrug thereof. In particular embodiments, administering may include oral administration, administration via implants, parenteral injection, intravenous injection, intraperitoneal injection, subcutaneous injection, bolus injection, infusion, rectal administration, vaginal administration, transdermal administration, inhalation, and combinations thereof. In additional embodiments, the methods may further include the step of administrating at least one anti-inflammatory agents, antimicrobial agents, matrix metalloprotease inhibitors, lipoxygenase inhibitors, cytokine antagonists, immunosuppressants, anti-cancer agents, anti-viral agents, cytokines, growth factors, immunomodulators, prostaglandins, anti-vascular hyperproliferation compounds, and combinations thereof concurrently with or in the same course of treatment with the compounds of Formula I.

Further embodiments of the invention are directed to a compound having the structure:

Other embodiments are directed to compositions including a compound having the structure:

Certain embodiments are directed to pharmaceutical compositions including a compound having the structure:

or a salt, ester, solvate, hydrate, or prodrug thereof, and a pharmaceutically acceptable carrier, excipient, or diluent. In some embodiments, the carrier may be selected from water, ethanol, polyol, glycerol, propylene glycol, liquid polyethylene glycol, vegetable oils, nut oils, and mixtures thereof. In various embodiments, the pharmaceutical composition may further include at least one flavoring agent, binding agent, lubricant, disintegrant, surface modifying agent, surfactant, suspending agent, stabilizing agent, fillers, glidant, compression aid, disintegrating agent, encapsulating material, or combinations thereof. In some embodiments, the pharmaceutical composition may further include at least one anti-inflammatory agents, antimicrobial agents, matrix metalloprotease inhibitors, lipoxygenase inhibitors, cytokine antagonists, immunosuppressants, anti-cancer agents, anti-viral agents, cytokines, growth factors, immunomodulators, prostaglandins, anti-vascular hyperproliferation compounds, and combinations thereof. In certain embodiments, the pharmaceutical composition is in unit dose form. In some embodiments, the compound having the structure:

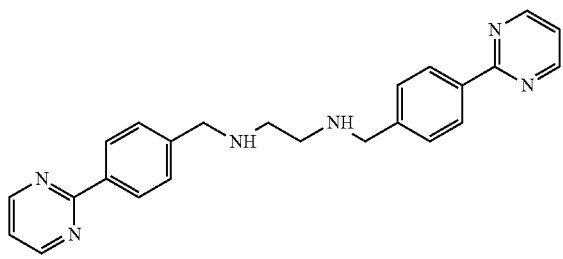 [SMILES: c1cnc(-c2ccc(CNCCNCc3ccc(-c4ncccn4)cc3)cc2)nc1]

or salt, ester, solvate, hydrate, or prodrug thereof may be about 15 wt. % to about 95 wt. % of total weight of the pharmaceutical composition, and in particular embodiments, each unit dose may include about 0.5 mg to about 500 mg of the compound depicted above or salt, ester, solvate, hydrate, or prodrug thereof.

Further embodiments are directed to methods for treating a respiratory injury or disease including the steps of administering to a patient in need of treatment a pharmaceutical composition comprising a compound having the structure:

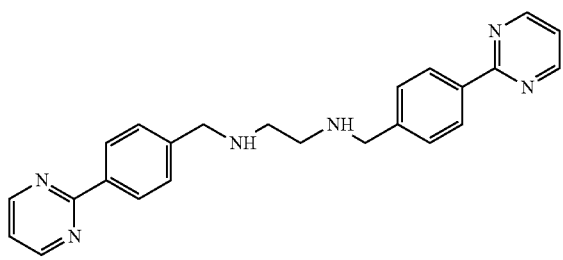 [SMILES: c1cnc(-c2ccc(CNCCNCc3ccc(-c4ncccn4)cc3)cc2)nc1]

or salt, ester, solvate, hydrate, or prodrug thereof; and a pharmaceutically acceptable carrier, excipient, or diluent. In various embodiments, the compound depicted above or salt, ester, solvate, hydrate, or prodrug thereof may be administered in an effective amount. In some embodiments, an effective amount may be from about 0.5 mg to about 500 mg of the compound or salt, ester, solvate, hydrate, or prodrug thereof, and in certain embodiments, an effective amount may include about 0.5 mg/kg to about 500 mg/kg per kg of patient body weight of the compound or salt, ester, solvate, hydrate, or prodrug thereof. In various embodiments, administering may include oral administration, administration via implants, parenteral injection, intravenous injection, intraperitoneal injection, subcutaneous injection, bolus injection, infusion, rectal administration, vaginal administration, transdermal administration, inhalation, and combinations thereof. In some embodiments, the pharmaceutical composition may further include a carrier such as, for example, water, ethanol, polyol, glycerol, propylene glycol, liquid polyethylene glycol, vegetable oils, nut oils, and mixtures thereof. In particular embodiments, the pharmaceutical composition may further include at least one flavoring agent, binding agent, lubricant, disintegrant, surface modifying agent, surfactant, suspending agent, stabilizing agent, fillers, glidant, compression aid, disintegrating agent, encapsulating material, or combinations thereof. In some embodiments, such methods may further include the step of administrating at least one anti-inflammatory agents, antimicrobial agents, matrix metalloprotease inhibitors, lipoxygenase inhibitors, cytokine antagonists, immunosuppressants, anti-cancer agents, anti-viral agents, cytokines, growth factors, immunomodulators, prostaglandins, anti-vascular hyperproliferation compounds, and combinations thereof either concurrently with the compound depicted above or in the same course of treatment with the compound depicted above.

The foregoing will become more apparent from the following detailed description, which proceeds with reference to the accompanying figures.

BRIEF DESCRIPTION OF THE DRAWINGS

For a better understanding of the disclosure and to show how the same may be carried into effect, reference will now be made to the accompanying drawings. It is stressed that the particulars shown are by way of example only and for purposes of illustrative discussion of the preferred embodiments of the present disclosure only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

(FIG. 8A) and micrographs of lung tissue for mice treated with Compound 005 and challenged with H1N1 (H1N1+005) compared to untreated, challenged mice (H1N1+Vehicle) (FIG. 8B).

FIGS. 18A-18E show a dexamethasone induced muscle myopathy model. Dexamethasone significantly increases FBXO3/TRAF6 protein levels in the TA muscle, induces a significant decrease in muscle weight and cross-sectional length. BC-1261 attenuates Dexamethasone-induced muscle atrophy in mice by degrading up-regulated TRAF6 protein. BC-1261 significantly ameliorates dexamethasone-induced tibialis anterior muscle loss even at the lost treatment dose at 0.5 mg/kg/d. Muscle wasting was also prevented indicated by the cross sectional measurements in the TA muscle H&E staining

DETAILED DESCRIPTION

Figure 1:
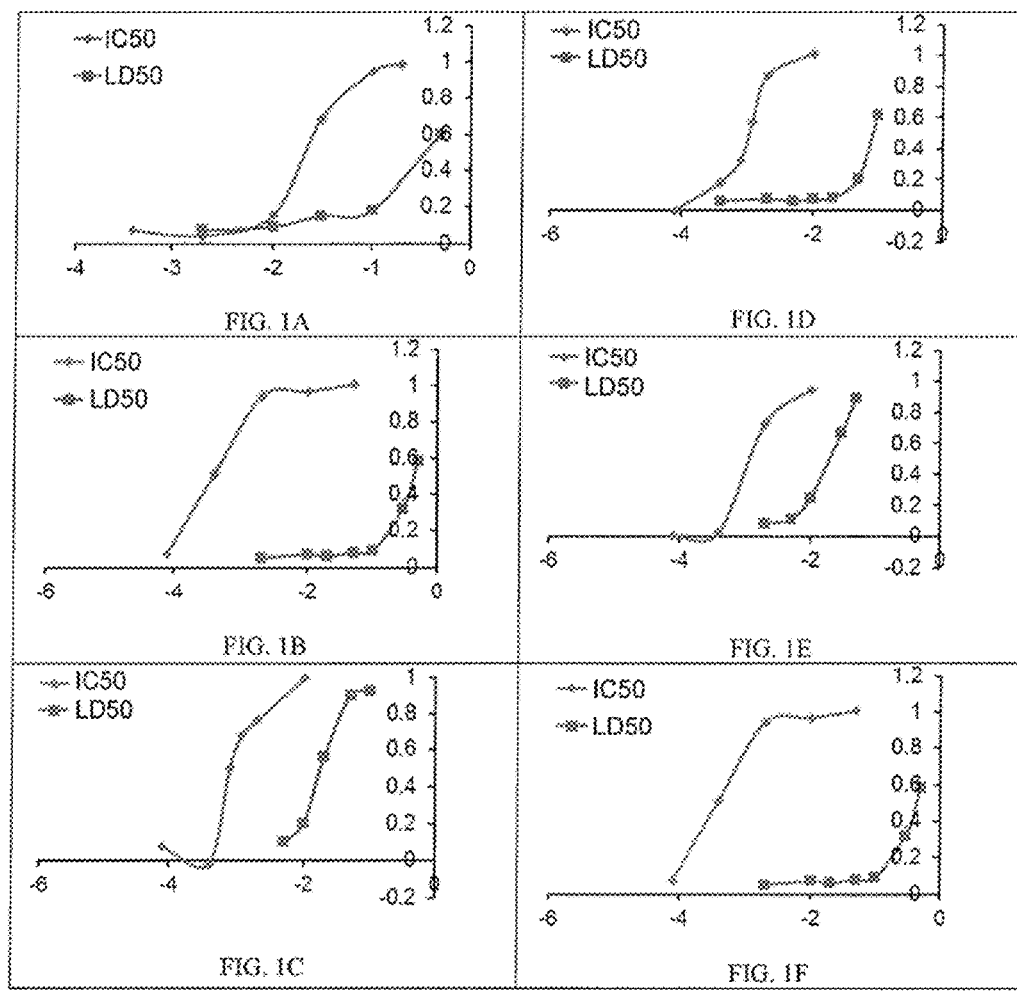
FIG. 1 shows representative IC50 data for Compound 014 (FIG. 1A), benzathine (FIG. 1B), Compound 004 (FIG. 1C), Compound 005 (FIG. 1D), Compound 010 (FIG. 1E), and Compound 015 (FIG. 1F).
Figure 2A:
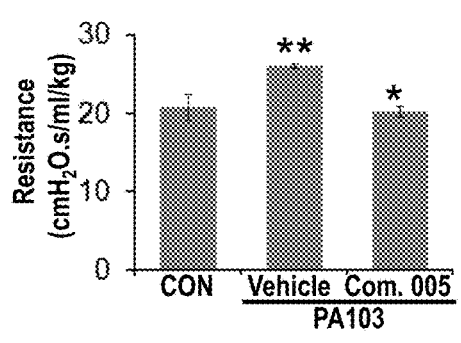
FIGS. 2A-2D show representative data, including lung resistance (FIG. 2A), lung elastance (FIG. 2B), lung compliance (FIG. 2C), and lung volume (FIG. 2D) data, for mice treated with Compound 005 and challenged with *Pseudomonas aeruginosa* strain PA103 compared to untreated and unchallenged mice.
Figure 2B:
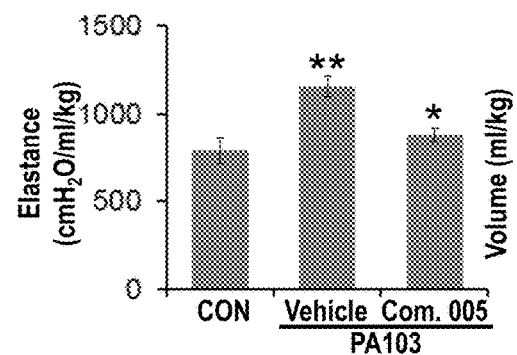
Figure 2C:
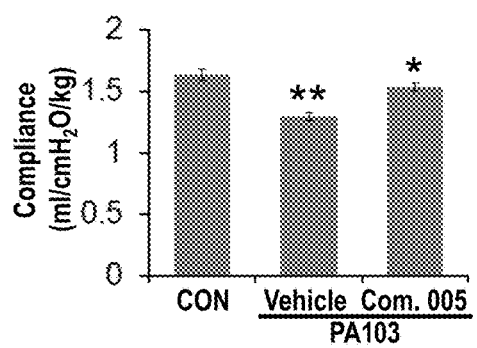
Figure 2D:
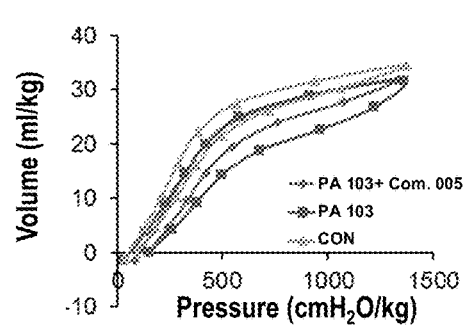

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise.

As used herein, the term "about" means plus or minus 10% of the numerical value of the number with which it is being used. Therefore, about 50% means in the range of 45%-55%.

"Optional" or "optionally" may be taken to mean that the subsequently described structure, event or circumstance may or may not occur, and that the description includes instances where the event occurs and instances where it does not.

"Administration" as used herein is inclusive of administration by another person to the subject or self-administration by the subject.

The term "alkyl" by itself or as part of another group refers to a straight and branched saturated carbon chain radical having a having from 1 to 10 carbon atoms. Unless the chain length is otherwise limited, such "alkyl groups" include, but are not limited to, methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl, nonyl, and decyl.

The term "alkoxy" or "alkyloxy" refers to any of the above alkyl groups linked to an oxygen atom, represented by the formula —OR where R is an alkyl group. Typical examples of "alkoxy groups" or "alkyloxy groups" include methoxy, ethoxy, n-propyloxy, isopropyloxy, n-butoxy, i-butoxy, sec-butyloxy, and t-butyloxy.

The term "alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "alkenyl" by itself or as part of another group refers to a straight or branched unsaturated carbon chain radical having from 2 to 10 carbon atoms and having at least one double bond between two of the carbon atoms in the chain. Unless the chain length is otherwise limited, such "alkenyl groups" include, but are not limited to, ethenyl, 1-propenyl, 2-propenyl, 2-methyl-1-propenyl, 1-butenyl, 2-butenyl, and the like.

The term "alkynyl" by itself or as part of another group refers to a straight or branched unsaturated carbon chain radical having 2 to 10 carbon atoms and having at least one triple bond between two of the carbon atoms in the chain. Unless the chain length is otherwise limited, such "alkynyl groups" include, but are not limited to, ethynyl, 1-propynyl, 2-propynyl, and the like.

In all instances herein where there is an alkenyl or alkynyl moiety as a substituent group, the unsaturated linkage, i.e., the vinyl or ethenyl linkage, is, generally, not directly attached to a nitrogen, oxygen, or sulfur moiety.

The term "aryl" by itself or as part of another group refers to monocyclic or bicyclic aromatic groups containing from 6 to 12 carbons in the ring portion. Typical examples include phenyl, biphenyl, naphthyl or tetrahydronaphthyl.

The term "aralkyl" or "arylalkyl" by itself or as part of another group refers to $C_{1-6}$alkyl groups as discussed above having an aryl substituent, such as benzyl, phenylethyl or 2-naphthylmethyl.

"Aryloxy" or "heteroaryloxy" refers to a group of the formula —OAr, wherein Ar is an aryl group or a heteroaryl group, respectively.

"Heteroaryl" as employed herein refers to groups having 5 to 14 ring atoms; 6, 10, or 14 pi electrons shared in a cyclic array; and containing carbon atoms and 1, 2, 3, or 4 oxygen, nitrogen, or sulfur heteroatoms. Examples of heteroaryl groups include, but are not limited to, thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups). The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

The terms "heteroarylalkyl" or "heteroaralkyl" as employed herein both refer to a heteroaryl group attached to an alkyl group. Typical examples include 2-(3-pyridyl)ethyl, 3-(2-furyl)-n-propyl, 3-(3-thienyl)-n-propyl, and 4-(1-isoquinolinyl)-n-butyl.

The term "cycloalkyl," by itself or as part of another group, refers to any saturated or partially unsaturated ringed structure containing 3 to 9 carbon atoms. Typical examples are cyclopropyl, cyclobutyl, cyclopentyl, cyclohexyl, cycloheptyl, cyclooctyl and cyclononyl.

The term "cycloalkylalkyl" or "cycloalkyl(alkyl)," by itself or as part of another group, refers to a cycloalkyl group attached to an alkyl group. Typical examples are 2-cyclopentylethyl, cyclohexylmethyl, cyclopentylmethyl, 3-cyclohexyl-n-propyl, and 5-cyclobutyl-n-pentyl.

The term "cycloalkenyl," by itself or as part of another group, refers to a partially unsaturated ringed structure containing 3 to 9 carbon atoms and 1 to 3 carbon-carbon double bonds. Typical examples include cyclopropenyl, cyclobutenyl, cyclopentenyl, cyclohexenyl, cyclohexadienyl, cycloheptenyl, cycloheptadienyl, cyclooctenyl, cyclooctadienyl, cyclooctatrienyl, cyclononenyl, and cyclononadienyl.

The term "heterocycle" or "heterocycloalkyl," by itself or as part of another group, refers to any saturated or partially unsaturated ring system having 5 to 14 ring carbon atoms and 1, 2, 3, or 4 oxygen, nitrogen, or sulfur ring heteroatoms. Typical examples include pyrrolidinyl, imidazolidinyl, pyrazolidinyl, tetrahydrofuranyl, tetrahydropyranyl, piperidyl, piperazinyl, quinuclidinyl, morpholinyl, and dioxacyclohexyl. Typical partially unsaturated examples include pyrrolinyl, imidazolinyl, pyrazolinyl, dihydropyridinyl, tetrahydropyridinyl, and dihydropyranyl.

The term "heteroatom" is used to mean an oxygen atom ("O"), a sulfur atom ("S") or a nitrogen atom ("N") that is incorporated into a aliphatic or ringed carbon chain, which may or may not include one or more double bonds. For example, when the heteroatom is nitrogen, it may form an $NR^aR^b$ moiety, where $R^a$ and $R^b$ are, independently, hydrogen or $C_1$ to $C_8$ alkyl, or together with the nitrogen to which they are bound form a saturated or unsaturated 5-, 6-, or 7-membered ring.

"Substituted" or "substitution" refer to replacement of a hydrogen atom of a molecule or an R-group with one or more additional R-groups.

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-groups/substituents include, for example, from $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, acyloxy groups, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, mercapto groups, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, $arC_{1-6}$alkyl, heterocyclyl and heteroaryl wherein each alkyl, alkenyl, alkynyl, cycloalkyl, aryl and heterocyclyl and groups containing them may be further optionally substituted.

Unless otherwise defined, the term "optionally-substituted" or "optional substituent" as used herein refers to a group which may or may not be further substituted with 1, 2, 3, 4 or more groups. The substituents may be optional substituents in the case N-heterocycles may also include but are not limited to $C_{1-6}$alkyl,i.e., N—$C_{1-3}$alkyl, more preferably methyl particularly N-methyl.

The term "carboxylate" or "carboxyl" refers to the group —COO⁻ or —COOH.

The term "ester" refers to a carboxyl group having the hydrogen replaced with, for example, a $C_{1-6}$alkyl group ("carboxyl$C_{1-6}$alkyl" or "alkylester"), an aryl or aralkyl group ("arylester" or "aralkylester") and so on. CO2C1-3alkyl groups are preferred, such as for example, methylester (CO 2Me), ethylester (CO2Et) and propylester (CO$_2$Pr) and includes reverse esters thereof (e.g. —OCOMe, —OCOEt and —OCOPr).

The term "halogen" refers to fluoro, bromo, chloro and iodo substituents.

The terms "halogenated alkyl" or "haloalkyl group" refer to an alkyl group as defined above with one or more hydrogen atoms present on these groups substituted with a halogen (F, Cl, Br, I).

"Nitro" refers to an R-group having the structure —$NO_2$.

The terms "hydroxyl" and "hydroxyl" are used interchangeably to refer to the radical —OH.

The terms "carbamoyl" and "aminocarbonyl" are used interchangeably to refer to the radical $NH_2$—C(O)—.

"Acyl" refers to a group having the structure —C(O)R, where R may be, for example, optionally substituted alkyl, optionally substituted aryl, or optionally substituted heteroaryl.

"Acyloxy" refers to a group having the structure —OC(O)R—, where R may be, for example, optionally substituted alkyl, optionally substituted aryl, or optionally substituted heteroaryl.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group. For example, an "alkylamino" or "alkylated amino" refers to —NRR', wherein at least one of R or R' is an alkyl.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H).

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Inhibiting" refers to inhibiting the full development of a disease or condition.

"Inhibiting" also refers to any quantitative or qualitative reduction in biological activity or binding, relative to a control.

The term "co-administration" or "co-administering" refers to administration of a FBXO3 inhibitor with at least one other therapeutic agent within the same general time period, and does not require administration at the same exact moment in time (although co-administration is inclusive of administering at the same exact moment in time). Thus, co-administration may be on the same day or on different days, or in the same week or in different weeks. The additional therapeutic agent may be included in the same composition as the FBXO3 inhibitor.

A "therapeutically effective amount" refers to a quantity of a specified agent sufficient to achieve a desired effect in a subject being treated with that agent. For example, a therapeutically amount of an FBXO3 inhibitor is an amount sufficient to inhibit inflammation in a subject. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as cancer. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments disclosed herein, the treatment inhibits inflammation in a subject.

Embodiments of the invention are directed to benzathine based compounds and pharmaceutical compositions for treating lung related injury and disease including these benzathine based compounds. Other embodiments are directed to methods for treating lung related injuries or diseases using these compounds and compositions, and methods for making compounds and pharmaceutical compositions including the benzathine based compounds.

The compounds of some embodiments may be of general Formula I:

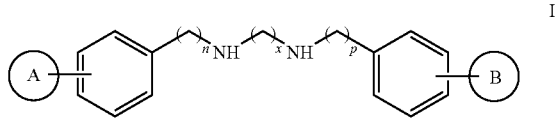

where:
x is an integer from 1 to 10;
A and B are each, independently, $C_{3-7}$cycloalkyl, $C_{3-7}$cycloalkyl-$C_{1-6}$alkyl, $C_{3-7}$heterocycloalkyl, $C_{3-7}$heterocycloalkyl-$C_{1-6}$alkyl, $C_{6-10}$aryl, $C_{6-10}$aryl-$C_{1-6}$alkyl, $C_{3-9}$heteroaryl, or $C_{3-9}$heteroaryl-$C_{1-6}$alkyl are each optionally substituted with 1, 2 or 3 independently selected $R^g$ groups;
each $R^g$ is, independently, halogen, $C_{1-6}$alkyl, $C_{1-6}$haloalkyl, hydroxyl, $C_{1-6}$alkoxy, $C_{1-6}$haloalkoxy, amino, $C_{1-6}$alkylamino, or di-$C_{1-6}$alkylamino; and
n and p are each, independently, integers from 1 to 10.

In various embodiments, A and B can be the same or different, and each of A and B can be substituted at any position on each phenyl ring. For example, A and B can be positioned in the ortho (o), meta (m), or para (p) position relative to the diamine connector portion of the molecule. In certain embodiments, each of A and B may be in para position.

While A and B can be any ringed structure, in some embodiments, each A and B may, independently, be a cyclohexyl, phenyl, 6-membered heteroaryl, 6-membered heterocycloalkyl, cyclopentyl, cyclopentene, cyclopentadiene, or 5-membered heteroaryl, 5-membered heterocycloalkyl each of which may be substituted with one or more $R^g$ groups. Various examples of 6-membered heteroaryl, 6-membered heterocycloalkyl, 5-membered heteroaryl, and 5-membered heterocycloalkyl are provided above with reference to the term "heterocycle." In certain embodiments, A and B may each, independently, be 6-membered heteroaryl, 6-membered heterocycloalkyl, 5-membered heteroaryl, and 5-membered heterocycloalkyl such as, but not limited to, pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, pyranyl, thiopyranyl, piperidinyl, morpholinyl, thiomorpholinyl, piperazinyl, or triazinyl. In particular embodiments, each A and B may, independently, be imidazolyl, pyridyl, pyrazolyl, oxadiazolyl and pyrimidinyl.

In embodiments where A and B are 6-membered heterocycloalkyl, 5-membered heteroaryl, and 5-membered heterocycloalkyl, the bond between each phenyl ring of the base structure may be facilitated through a carbon or a hetero atom. For example, A and B include:

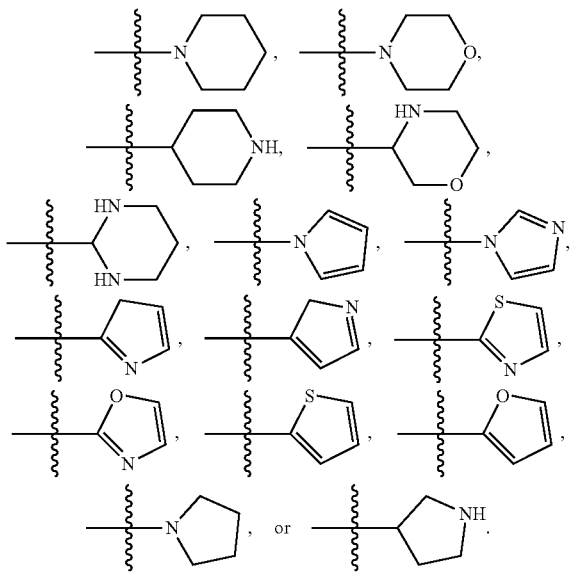

Of course, 6-membered heterocycloalkyl, 5-membered heteroaryl, and 5-membered heterocycloalkyl encompassed by A and B can include additional heteroatoms, different heteroatoms, and various arrangements of heteroatoms in addition to those provided above.

Like the 6-membered heterocycloalkyl, 5-membered heteroaryl, and 5-membered heterocycloalkyl described above, the bond connecting A and B to the phenyl ring of the base structure and each of A and B can be at any position on a 6-membered heteroaryl. For example, A and B include:

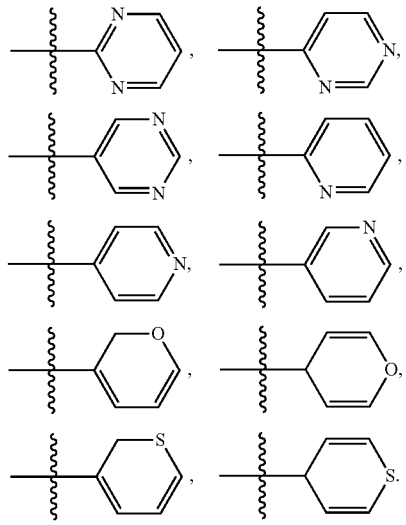

Of course, 6-membered heteroaryl encompassed by A and B can include additional heteroatoms and various arrangements of heteroatoms in addition to those provided above.

In embodiments, in which A and B are, independently, cycloalkyl-alkyl, heterocycloalkyl-alkyl, aryl-alkyl, or heteroaryl-alkyl, the alkyl portion of these substituents may be disposed between the phenyl ring of the base structure of the cycloalkyl, heterocycloalkyl, aryl, or heteroaryl portion of the substituent. Examples of such compounds are provided by Formula Ia:

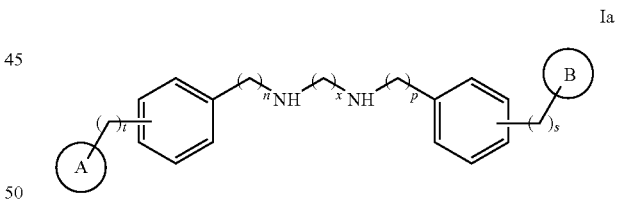

Ia where each s and t are, independently, 1 to 5 or 1 to 3. In such embodiments, A and B can be any of the substituents described above, and in particular embodiments, A and B can be any of the 6-membered heteroaryl, 6-membered heterocycloalkyl, 5-membered heteroaryl, and 5-membered heterocycloalkyl substituents described above.

In various embodiments described with reference to Formula I or Formula Ia, x may be an integer of from 2 to 8, 2 to 6, or 2 to 10, and in particular embodiments, x may be 2. In various embodiments, n and p may be the same or different. For example, in some embodiments, n and p may, independently be integers from 1 to 8, 1 to 6, or 2 to 10. In particular embodiment, n and p may be the same and may be 1 to 3, and in certain embodiments, n and p may be 1.

Examples of the compounds encompassed by the Formulae I and Ia are provided in Table 1:
TABLE 1
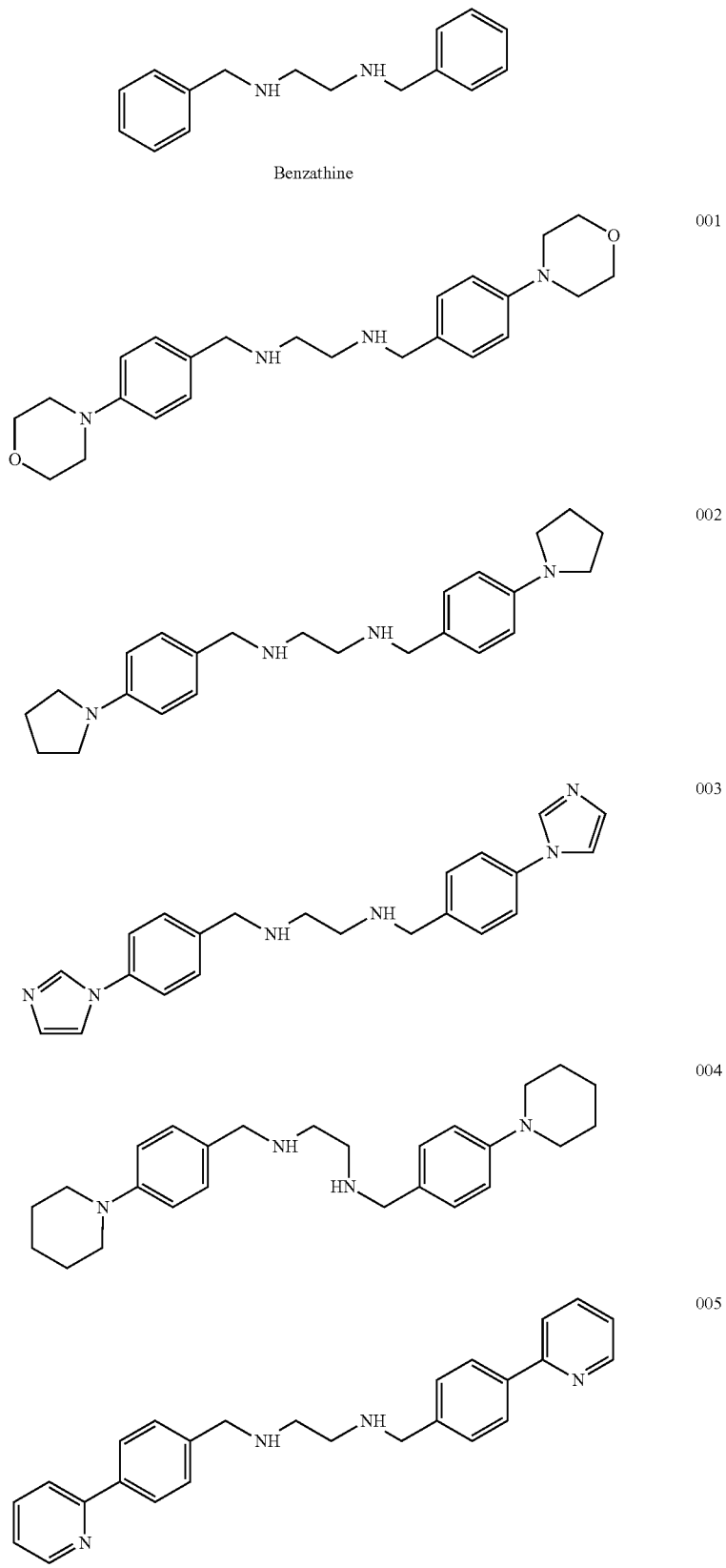

TABLE 1-continued
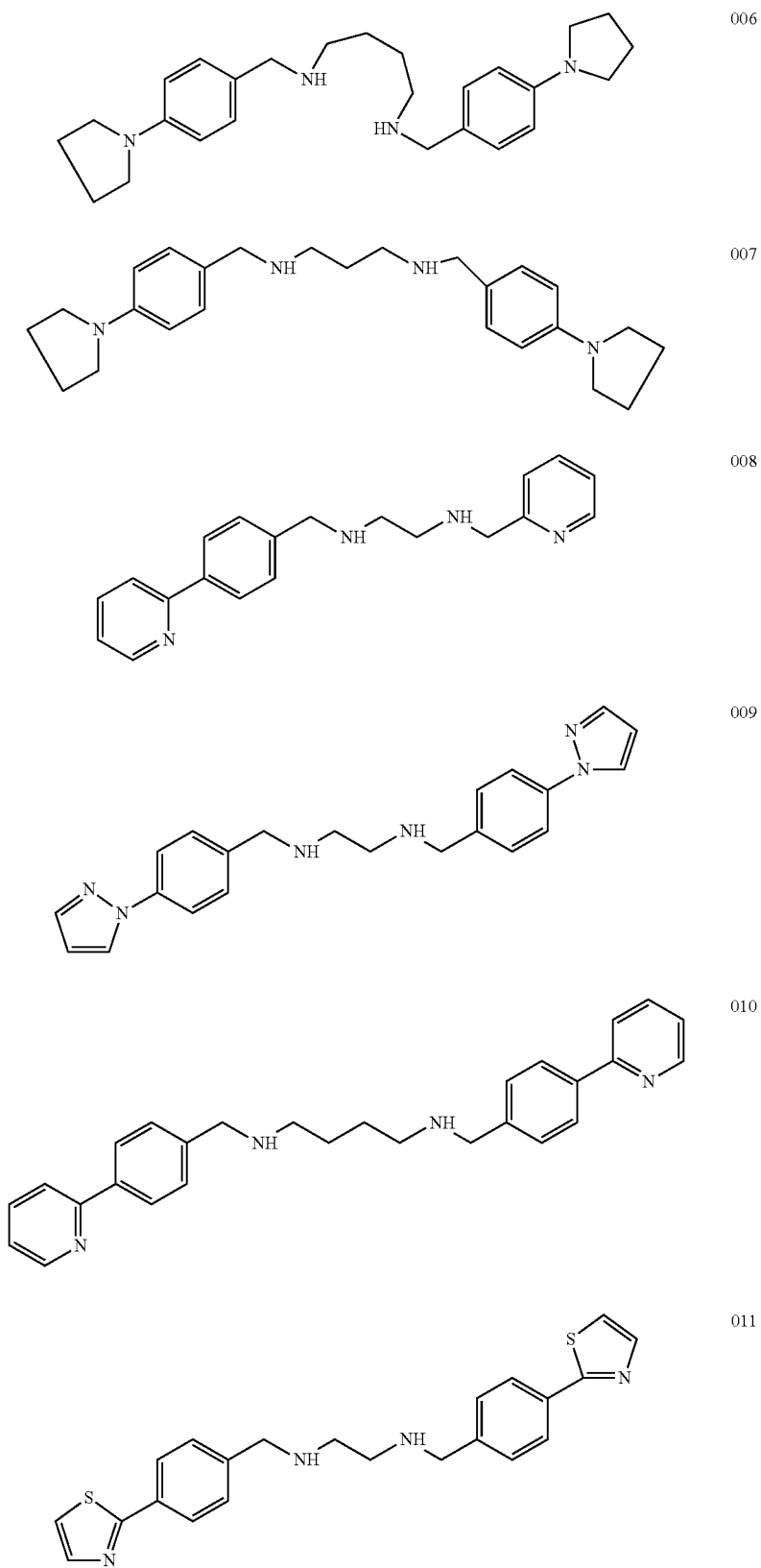

TABLE 1-continued
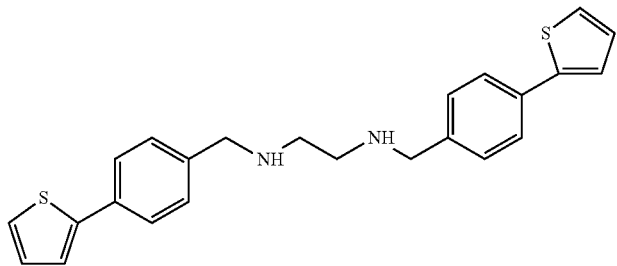 [SMILES: c1csc(-c2ccc(CNCCNCc3ccc(-c4cccs4)cc3)cc2)c1]
012
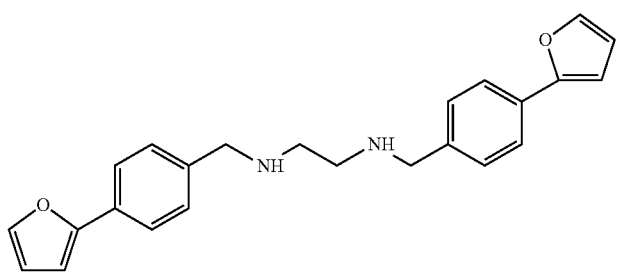 [SMILES: c1coc(-c2ccc(CNCCNCc3ccc(-c4ccco4)cc3)cc2)c1]
013
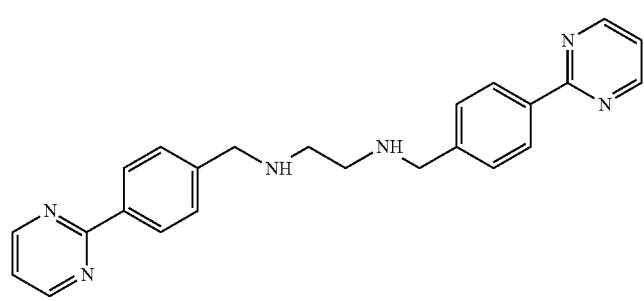 [SMILES: c1cnc(-c2ccc(CNCCNCc3ccc(-c4ncccn4)cc3)cc2)nc1]
014
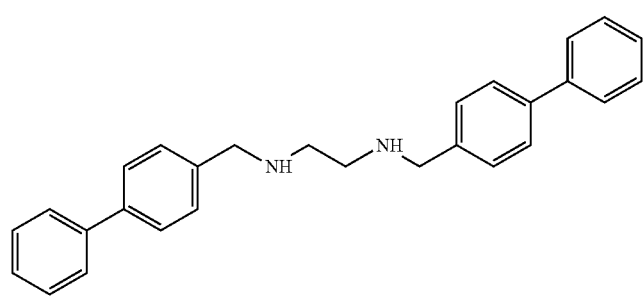 [SMILES: c1ccc(-c2ccc(CNCCNCc3ccc(-c4ccccc4)cc3)cc2)cc1]
015
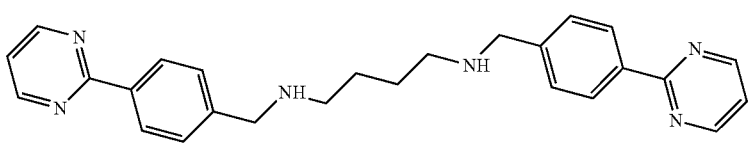 [SMILES: c1cnc(-c2ccc(CNCCCCNCc3ccc(-c4ncccn4)cc3)cc2)nc1]
016
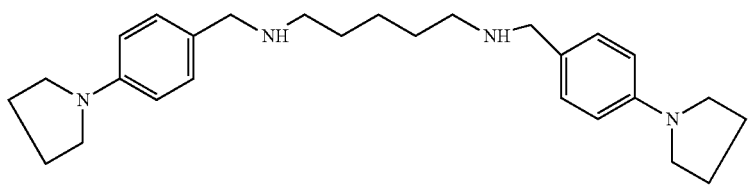 [SMILES: c1cc(N2CCCC2)ccc1CNCCCCCNCc1ccc(N2CCCC2)cc1]
017

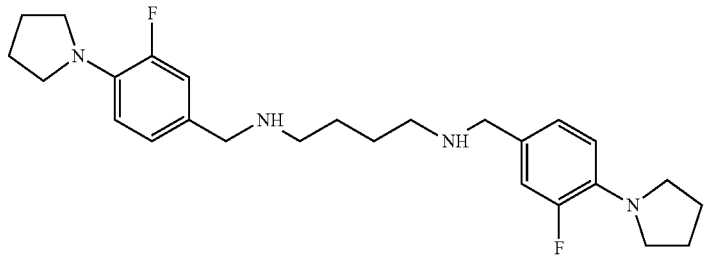 [SMILES: Fc1cc(CNCCCCNCc2ccc(N3CCCC3)c(F)c2)ccc1N1CCCC1]

018

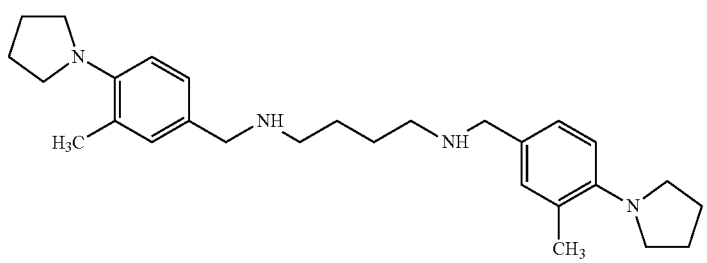 [SMILES: Cc1cc(CNCCCCNCc2ccc(N3CCCC3)c(C)c2)ccc1N1CCCC1]

0019

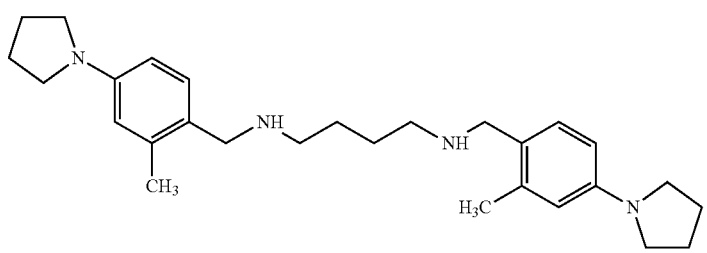 [SMILES: Cc1cc(N2CCCC2)ccc1CNCCCCNCc1ccc(N2CCCC2)cc1C]

020

Also disclosed herein in one embodiment are methods using FBXO3 inhibitors. Illustrative FBXO3 inhibitors include benzathine compounds, optionally-substituted diaminoalkanes (e.g., 1,10-diaminodecane), substituted quinolines (e.g., quinidine, hydroxychloroquine, primaquine), haematoxylin, tetramethylenebis, naphthacaine, ampicillin, and elliptine, and pharmaceutically acceptable salts and esters thereof.

The benzathine compound may be benzathine or a benzathine analog. In certain embodiments the benzathine compound is not benzathine penicillin In certain embodiments the benzathine analog includes a divalent diamine core moiety, a first aryl-containing moiety at a first terminal end of the divalent diamine core moiety, and a second aryl-containing moiety at a second terminal end of the divalent diamine core moiety. Each amino groups of the diamine group may be individually —NH— or —NR—, wherein R is a substituted group as described such as a lower alkyl, alkoxy, hydroxy, acyl, acyloxy, alkoxycarbonyl, aryl, carboxyl, or ester. The divalent diamine core moiety may include an optionally-substituted alkanediyl, an optionally-substituted cycloalkanediyl, an optionally-substituted aryldiyl, or an optionally-substituted alkanearyldiyl positioned between the two amino groups. In certain embodiments the two amino groups of the diamine may together with carbon atoms form a heteroaryldiyl group. The terminal aryl-containing groups may each individually be an aralkyl group (preferably a benzyl group) or an N-heteroaralkyl group such as -alkyl-pyrazinyl, -alkyl-pyrimidinyl, -alkyl-pyridazinyl, or -alkyl-pyridinyl. The aryl ring of the aralkyl group may be substituted with an optionally-substituted N-heterocyclic group. In certain embodiments, the optionally-substituted N-heterocyclic group is located at a ring position para to the point of attachment of the aralkyl group to the divalent diamine core moiety.

Illustrative benzathine analogs include optionally-substituted N-heterocyclic-substituted benzathines. In certain embodiments, the benzathine analogs include two phenyl rings, wherein at least one, and preferably both, of the phenyl rings are substituted with an optionally-substituted N-heterocyclic group, which optionally-substituted N-heterocyclic may be the same or different. In certain embodiments, the optionally-substituted N-heterocyclic group is located at a ring position para to the point of attachment of the phenyl ring to the benzathine molecular scaffold.

Illustrative N-heterocyclic groups include, for example, pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, piperidinyl, morpholinyl, thiomorpholinyl, piperazinyl, and triazinyl. Particularly preferred N-heterocyclic groups include imidazolyl, pyridyl, pyrazolyl, oxadiazolyl and pyrimidinyl.

The benzathine analogs, or pharmaceutically acceptable salts or esters thereof, may have structure of formula V:

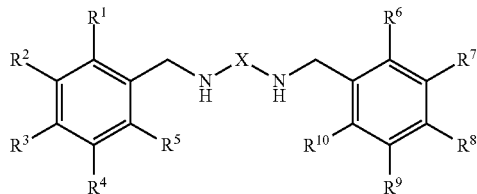

wherein X is a divalent or tetravalent linking moiety; and $R^1$-$R^{10}$ are each individually H, optionally-substituted alkyl, optionally-substituted alkoxy, optionally-substituted aryl, optionally-substituted cycloalkyl, optionally-substituted heterocyclic, halogen, amino, or hydroxy.

In certain embodiments of formula V, X is an optionally-substituted alkanediyl, an optionally-substituted cycloalkanediyl, an optionally-substituted aryldiyl, or an optionally-substituted alkanearyldiyl. For example, X may be an alkanediyl having a structure of —$C_nH_{2n}$— wherein n is 1 to 10, more preferably 2 to 5; X may be a —$C_6H_{10}$— cycloalkanediyl; or X may be a —$C_6H_4$— aryldiyl. A particularly preferred X moiety is —$CH_2$—$CH_2$—.

In certain embodiments of formula V, X is a tetravalent moiety that is derived from a spiro structure wherein the nitrogen atoms of the diamine core form N-heteroatoms of the spiro structure. For example, X together with the diamine may form a diazaspirodecane.

In certain embodiments of formula V, at least one of $R^1$-$R^{10}$ is not H. In certain embodiments of formula V, at least one of $R^3$ or $R^8$ is an optionally-substituted alkyl, optionally-substituted alkoxy, optionally-substituted aryl, optionally-substituted cycloalkyl, optionally-substituted heterocyclic, halogen, amino, or hydroxy. In certain embodiments of formula I, at least one of $R^3$ or $R^8$, and preferably both of $R^3$ and $R^8$, is an unsubstituted alkoxy, aryl-substituted alkoxy, halo-substituted alkoxy, aryl, optionally-substituted heterocyclic, halogen, amino, or hydroxy. In certain embodiments of formula V, at least one of $R^1$-$R^{10}$ is an N-heterocyclic, particularly a 5-membered or 6-membered N-heterocyclic. In certain embodiments of formula I, at least one of $R^3$ or $R^8$, and preferably both of $R^3$ and $R^8$, is an N-heterocyclic, particularly a 5-membered or 6-membered N-heterocyclic. Illustrative N-heterocyclic groups include, for example, pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, piperidinyl, morpholinyl, thiomorpholinyl, piperazinyl, and triazinyl. Particularly preferred N-heterocyclic groups include imidazolyl, pyridyl, pyrazolyl, and pyrimidinyl. Especially preferred N-heterocyclic groups include imidazolyl, pyridyl, and pyrazolyl. In certain embodiments of formula V, $R^1$, $R^2$, $R^4$, $R^5$, $R^6$, $R^7$, $R^9$ and $R^{10}$ are each H. In certain embodiments of formula V, $R^1$, $R^2$, $R^4$, $R^5$, $R^6$, $R^7$, $R^9$ and $R^{10}$ are each H; X is an optionally-substituted alkanediyl, and $R^3$ and $R^8$ are each individually an optionally-substituted 5-membered or 6-membered N-heterocyclic. In certain embodiments of formula I, $R^3$ and $R^8$ are each the same group.

Disclosed herein in a further embodiment are methods of using compounds, or pharmaceutically acceptable salts or esters thereof, having a structure of formula VI:

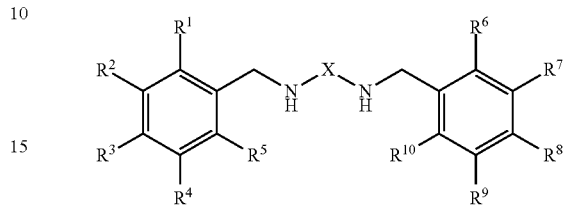

wherein X is a divalent linking moiety; and $R^1$-$R^{10}$ are each individually H, optionally-substituted alkyl, optionally-substituted alkoxy, optionally-substituted aryl, optionally-substituted cycloalkyl, optionally-substituted heterocyclic, halogen, amino, or hydroxy, provided that at least one of $R^3$ or $R^8$ is an optionally-substituted alkyl, a substituted alkoxy, optionally-substituted aryl, optionally-substituted cycloalkyl, optionally-substituted heterocyclic, or halogen.

In certain embodiments of formula VI, X is an optionally-substituted alkanediyl, an optionally-substituted cycloalkanediyl, an optionally-substituted aryldiyl, or an optionally-substituted alkanearyldiyl. For example, X may be an alkanediyl having a structure of —$C_nH_{2n}$— wherein n is 1 to 10, more preferably 2 to 5; X may be a —$C_6H_{10}$— cycloalkanediyl; or X may be a —$C_6H_4$— aryldiyl. A particularly preferred X moiety is —$CH_2$—$CH_2$—.

In certain embodiments of formula VI, at least one of $R^1$-$R^{10}$ is an N-heterocyclic, particularly a 5-membered or 6-membered N-heterocyclic. In certain embodiments of formula VI, at least one of $R^3$ or $R^8$, and preferably both of $R^3$ and $R^8$, is an N-heterocyclic, particularly a 5-membered or 6-membered N-heterocyclic. Illustrative N-heterocyclic groups include, for example, pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, piperidinyl, morpholinyl, thiomorpholinyl, piperazinyl, and triazinyl. Particularly preferred N-heterocyclic groups include imidazolyl, pyridyl, pyrazolyl, oxadiazolyl and pyrimidinyl. Especially preferred N-heterocyclic groups include imidazolyl, pyridyl, and pyrazolyl. In certain embodiments of formula II, $R^1$, $R^2$, $R^4$, $R^5$, $R^6$, $R^7$, $R^9$ and $R^{10}$ are each H. In certain embodiments of formula VI, $R^1$, $R^2$, $R^4$, $R^5$, $R^6$, $R^7$, $R^9$ and $R^{10}$ are each H; X is an optionally-substituted alkanediyl, and $R^3$ and $R^8$ are each individually an optionally-substituted 5-membered or 6-membered N-heterocyclic. In certain embodiments of formula VI, $R^3$ and $R^8$ are each the same group.

Disclosed herein in a further embodiment are compounds, or pharmaceutically acceptable salts or esters thereof, having a structure of formula VII:

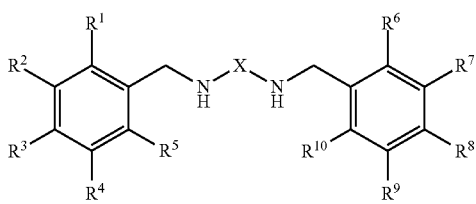

wherein X is a divalent linking moiety; and $R^2$-$R^5$ and $R^7$-$R^{10}$ are each individually H, optionally-substituted alkyl, optionally-substituted alkoxy, optionally-substituted aryl, optionally-substituted cycloalkyl, optionally-substituted heterocyclic, halogen, amino, or hydroxy.

In certain embodiments of formula VII, X is an optionally-substituted alkanediyl, an optionally-substituted cycloalkanediyl, an optionally-substituted aryldiyl, or an optionally-substituted alkanearyldiyl. For example, X may be an alkanediyl having a structure of —$C_nH_{2n}$— wherein n is 1 to 10, more preferably 2 to 5; X may be a —$C_6H_{10}$— cycloalkanediyl; or X may be a —$C_6H_4$— aryldiyl. A particularly preferred X moiety is —$CH_2$—$CH_2$—. In certain embodiments of formula VII, $R^2$-$R^5$ and $R^7$-$R^{10}$ are each individually H.

Disclosed herein in a further embodiment are methods of using compounds, or pharmaceutically acceptable salts or esters thereof, having a structure of formula VIII:

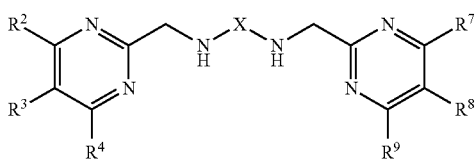

wherein X is a divalent linking moiety; and $R^2$-$R^4$ and $R^7$-$R^9$ are each individually H, optionally-substituted alkyl, optionally-substituted alkoxy, optionally-substituted aryl, optionally-substituted cycloalkyl, optionally-substituted heterocyclic, halogen, amino, or hydroxy.

In certain embodiments of formula VIII, X is an optionally-substituted alkanediyl, an optionally-substituted cycloalkanediyl, an optionally-substituted aryldiyl, or an optionally-substituted alkanearyldiyl. For example, X may be an alkanediyl having a structure of —$C_nH_{2n}$— wherein n is 1 to 10, more preferably 2 to 5; X may be a —$C_6H_{10}$— cycloalkanediyl; or X may be a —$C_6H_4$— aryldiyl. A particularly preferred X moiety is —$CH_2$—$CH_2$—. In certain embodiments of formula VIII, $R^2$-$R^5$ and $R^7$-$R^{10}$ are each individually H.

The various embodiments described above encompass all stereoisomers and optical isomers of the compounds described above including all individual enantiomers, any mixtures of enantiomers, and diastereomers that can arise as a consequence of structural asymmetry of atoms. Embodiments further include purified enantiomers that may or may not contain residual non-selected enantiomer or diastereomer. Accordingly, compounds and compositions may be provided as individual pure enantiomers or as stereoisomeric mixtures, including racemic mixtures. In certain embodiments, the compounds disclosed herein are synthesized in or are purified to be in substantially pure form such as in a 90% enantiomeric excess, a 95% enantiomeric excess, a 97% enantiomeric excess or even in greater than a 99% enantiomeric excess, such as in enantiopure form.

In some embodiments, the compounds described above may be in free base or salt form. The terms "pharmaceutically acceptable salt" refers to salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

Particular embodiments are directed to acid salts of the compounds described above, and some such embodiments include hydrochloric acid and acetic acid salts of any of the compounds described above including the compounds of Formula I and Formula Ia, any of the compounds of Table 1, or any other compounds disclosed herein. Acid salts of the compounds of various embodiments may become protonated. Some embodiments include compounds of the invention that are fully protonated compounds and other embodiments include compounds of the invention that are partially protonated.

These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., J. Pharm. Sci. 66:1 (1977).

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. Particular examples of amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl) methylamine, N,N-dimethyl-N-(2-hydroxyethyl)amine, tri-(2-hydroxyethyl)amine and N-methyl-D-glucamine For additional examples of "pharmacologically acceptable salts," see Berge et al., *J. Pharm. Sci.* 66:1 (1977).

In other embodiments, the compounds described above may be in ester form. "Pharmaceutically acceptable esters" includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocyclyl above. Pharmaceutically acceptable esters thus include C1-C22 fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$alkyl, or $C_{1-4}$alkoxy) or amino); sulphonate esters, such as alkyl- or aralkylsulphonyl (for example, methanesulphonyl); or amino acid esters (for example, L-valyl or L-isoleucyl). Still other embodiments include prodrugs of the compounds described above. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters, see Svensson and Tunek, Drug Metabolism Reviews 165 (1988).

A prodrug form of a compound may be administered in an inactive form or a form having reduced activity that is transformed into an active or more active form of the drug by an enzymatic or chemical process. For example, in some embodiments, a prodrug form of a compound such as those described above may include one or more metabolically cleavable groups that can be removed by solvolysis, hydrolysis, or physiological metabolisms to release the pharmaceutically active form of the compound. In other embodiments, prodrugs may include acid derivatives of the compounds of the invention. Acid derivatives are well known in the art and include, but are not limited to, esters or double esters such as, for example, (acyloxy) alkyl esters or ((alkoxycarbonyl)oxy)alkyl esters prepared by reaction of an acid on the parent molecule with a suitable alcohol. Without wishing to be bound by theory, the compounds of the invention may have activity in both their acid and acid derivative forms. However, the acid derivative form may exhibit enhanced solubility, tissue compatibility or delayed release in the mammalian organism (see, e.g., Bundgard, H., Design of Prodrugs, pp. 7-9, 21-24, Elsevier, Amsterdam 1985). In other embodiments, prodrugs may include an amide and can be prepared by reacting a parent compound containing an acid with an amine, and in yet other embodiments, simple aliphatic or aromatic esters derived from acidic groups pendent on a compound of this invention may be prepared as prodrugs.

Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Yet other embodiments include solvates or hydrates of the described above. In some cases, hydration of a compound may occur during manufacture of the compounds or compositions including the compounds as a consequence of the method for preparing the compound or as a result of a specific step used to create a hydrate or solvate of the compound. In other cases, hydration may occur over time due to the hygroscopic nature of the compounds. Such hydrated compounds whether intentionally prepared or naturally produced are encompassed by the invention.

Further embodiments are directed to pharmaceutical compositions including one or more of the compounds described above or pharmaceutically acceptable salts, pharmaceutically acceptable esters of the compounds described above or solvates, hydrates or prodrugs of any of the compounds described above. In some embodiments, such compounds may be administered neat and, therefore, the pharmaceutical composition may only include one or more of the compounds described above or salts, esters, solvates, hydrates, or prodrugs thereof. In other embodiments, the compounds, salts, esters, solvates, hydrates, or prodrugs thereof may be combined with at least one pharmaceutically acceptable carriers, excipient, or diluent. Examples of carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. The term "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

In some embodiments, pharmaceutical compositions may include one or more compound or salt, ester, solvate, hydrate, or prodrug thereof and a solid carriers for oral or parenteral administration. In certain embodiments, such pharmaceutical compositions may further include one or more additional components such as flavoring agents, lubricants, solubilizers, suspending agents, fillers, glidants, compression aids, binders or tablet-disintegrating agents, or various encapsulating materials. Oral formulations may be in any conventionally used oral form, including tablets, capsules, buccal forms, troches, lozenges, oral liquids, suspensions, or solutions. In powders, the carrier can be a finely divided solid, which is an admixture with a finely divided compound or salt, ester, solvate, hydrate, or prodrug thereof. In tablets, the compound or salt, ester, solvate, hydrate, or prodrug thereof can be mixed with a carrier having the appropriate compression properties and compacted in the shape and size desired. In various embodiments, the powders and tablets can contain up to 99 wt. % of the compound or salt, ester, solvate, hydrate, or prodrug thereof, and in some embodiments, the powder or tablet may include from about 10 wt. % to about 100 wt. %, about 15 wt. % to about 95 wt. %, about 20 wt. % to about 90 wt. %, about 25 wt. % to about 85 wt. %, or about 30 wt. % to about 75 wt. % compound or salt, ester, solvate, hydrate, or prodrug thereof or any individual concentration or range encompassed by these example ranges.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine Oral formulations herein can utilize standard delay or time-release formulations to alter the absorption of the compound. The oral formulation can also consist of administering a compound disclosed herein in water or fruit juice, containing appropriate solubilizers or emulsifiers as needed.

Capsules can contain mixtures of one or more compound or salt, ester, solvate, hydrate, or prodrug thereof and one or more inert fillers, diluents, or combinations thereof such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Liquid carriers can be used in preparing solutions, suspensions, emulsions, syrups, elixirs, and for inhaled delivery. Any of the compounds or salts, esters, solvates, hydrates, or prodrugs thereof described above can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). Liquid pharmaceutical compositions, which are sterile solutions or suspensions, can be utilized by, for example, intravenous, intramuscular, intraperitoneal or subcutaneous injection. For parenteral administration, the carrier can be an oily ester such as ethyl oleate and isopropyl myristate. Compositions for oral administration can be in either liquid or solid form. The liquid carrier for pressurized compositions can be halogenated hydrocarbon or other pharmaceutically acceptable propellants.

In some embodiments, the compound or salt, ester, solvate, hydrate, or prodrug thereof can be encapsulates with lipid formulations or formulated as nanocapsules. Lipid formulations and nanocapsules can be prepared by methods known in the art.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils. These preparations typically contain a preservative to inhibit the growth of microorganisms.

The pharmaceutical compositions of various embodiments can be prepared in unit dosage form such that each unit has one dose of the compound or salt, ester, solvate, hydrate, or prodrug thereof or a fraction of a dose of the compound or salt, ester, solvate, hydrate, or prodrug thereof, i.e., a sub-divided dose. For example, each tablets, capsules, powders, solutions, suspensions, emulsions, granules, or suppositories of the pharmaceutical composition may include a particular amount of the compound or salt, ester, solvate, hydrate, or prodrug thereof that provides a single dose or two or more units of the pharmaceutical composition can be combined to provide a single dose of the compound or salt, ester, solvate, hydrate, or prodrug thereof. Unit dosage forms can be packaged in, for example, powder packets, vials, ampoules, prefilled syringes, or sachets containing liquids. Alternatively, the unit dosage form can be a capsule or tablet itself. In various embodiments, each unit dose can contain from about 0.5 mg to about 500 mg of compound or salt, ester, solvate, hydrate, or prodrug thereof. In particular embodiments, each unit dose may include from about 0.75 mg to about 400 mg, about 1 mg to about 300 mg, about 2 mg to about 250 mg, about 5 mg to about 200 mg, about 10 to about 150 mg, or about 20 to about 100 mg of compound or salt, ester, solvate, hydrate, or prodrug thereof or any individual amount or range encompassed by these example ranges. The amount of compound or salt, ester, solvate, hydrate, or prodrug thereof in each unit dose can be selected to allow for variability in administration, for example, a patient may be instructed to take, 1 or 2 or 3 or 4 or more unit doses of the compound or salt, ester, solvate, hydrate, or prodrug thereof per day to achieve an effective amount, and the amount in each unit dose may allow for ease of ingestion, for example, a single tablet having a large amount of the compound or salt, ester, solvate, hydrate, or prodrug thereof may be more difficult to swallow than two or more smaller unit doses.

Pharmaceutical compositions of various embodiments may generally have a neutral pH. For example, in some embodiments, the pH of the pharmaceutical compositions may be about 5.0 to about 8.0 or about 5.0 to about 7.0. In embodiments in which the pharmaceutical composition includes an acid salt of the compounds described above including the compounds of Formula I and Formula Ia, any of the compounds of Table 1, or any other compounds disclosed herein, a carrier, buffer, or diluent may be incorporated into the pharmaceutical composition that is capable of reducing the pH of the compositions. The carrier, buffer, or diluent can vary among embodiments and may or may not have be alkaline or have a pH higher than the acid salt of the compounds of the invention. For example, in some embodiments, phosphate buffered saline (PBS), which typically has a neutral pH (about 7.4) may be used to reduce the pH of the pharmaceutical composition.

In particular embodiments, the compounds or salts, esters, solvates, hydrates, or prodrugs thereof can be combined with one or more additional therapeutic agents in a single pharmaceutical composition. Any therapeutic known in the art can be combined with the compounds or salts, esters, solvates, hydrates, or prodrugs thereof described above, and such additional therapeutics can be chosen to mitigate symptoms or otherwise aid in healing either independently or when combined with the compounds or salts, esters, solvates, hydrates, or prodrugs thereof described above. In particular embodiments, such agents may include, but are not limited to, another anti-inflammatory agent, an antimicrobial agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, or an anti-vascular hyperproliferation compound, and the like and combinations thereof.

In some embodiments, the compounds of the invention including the compounds of Formula I and Formula Ia, any of the compounds of Table 1, or any other compounds disclosed herein, can be used as stabilizers for other therapeutic compounds. For example, a pharmaceutical composition may include a therapeutically effective amount of anti-inflammatory agent, an antimicrobial agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, or an anti-vascular hyperproliferation compound and a sufficient amount of one or more of the compounds described above to improve the half-life following administration or shelf-life of the therapeutic compound.

Certain embodiments are directed to Compound 014:

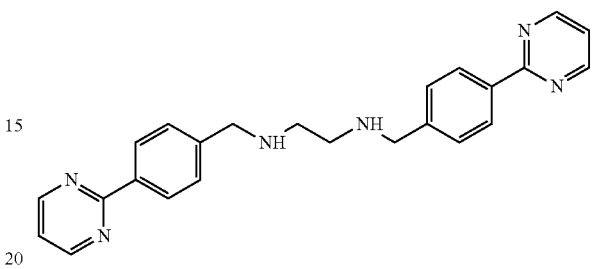

and stereoisomers, salts, esters, solvates, hydrates, or prodrugs thereof and pharmaceutical compositions including Compound 014. Various embodiments pharmaceutical compositions including any of the carriers, excipients, diluents, flavoring agent, binding agents, lubricants, disintegrants, surface modifying agents, surfactants, suspending agents, stabilizing agents, fillers, glidants, compression aids, disintegrating agents, encapsulating materials, described above, and any combinations thereof. Additionally, Compound 014 can be included in such pharmaceutical compositions any concentration described above, for example, from about 15 wt. % to about 95 wt. % of a total weight of the pharmaceutical composition, and about 0.5 mg to about 500 mg of compound 014 or salt, ester, solvate, hydrate, or prodrug thereof may be present in such pharmaceutical compositions. However, Compound 014 may provide improved efficacy over other compounds encompassed by Formulae I and Ia. As such, less Compound 014 may be necessary to provide equivalent relief from inflammation.

For example, FIG. 1 shows $IC50_{IL1\beta}$ measurements for various compounds encompassed by Formula I having some structural similarity to Compound 014. As illustrated in FIG. 1: benzathine exhibits an $IC50_{IL1\beta}$ of 25 µg/ml (FIG. 1B), Compound 004 exhibits an $IC50_{IL1\beta}$ of 0.8 µg/ml (FIG. 1C), Compound 005 exhibits an $IC50_{IL1\beta}$ of 0.9 µg/ml (FIG. 1D), Compound 010 exhibits an $IC50_{IL1\beta}$ of 1.5 µg/ml (FIG. 1E), and Compound 015 exhibits an $IC50_{IL1\beta}$ of 2.0 µg/ml (FIG. 1F). By comparison, Compound 014 exhibits an $IC50_{IL1\beta}$ of 0.4 µg/ml (FIG. 1A) thereby delivering twice (2x) the efficacy of other compounds of Formula I. As such, less than about half the amount of Compound 014 is necessary to achieve maximum inhibition of IL1β than the structurally similar compounds, and significantly less Compound 014 may be necessary to achieve efficacy when Compound 014 is administered to a patient as compared to structurally similar compounds. Reducing the amount of drug administrated may reduce side effects, reduced frequency of administration, reduced infusion or bolus injection volume, provide for smaller oral dose, and the like.

Additional embodiments are directed to methods for treating a patient with one or more of the compounds or salts, esters, solvates, hydrates, or prodrugs thereof described above. In general, such methods may include the step of administering the compound or salt, ester, solvate, hydrate, or prodrug thereof to a patient in need of treatment. In some embodiments, such methods may further include co-administering an additional therapeutic agent with the compounds or salts, esters, solvates, hydrates, or prodrugs thereof described above. Such additional agents include, but are not limited to, other anti-inflammatory agents, antimicrobial agents, matrix metalloprotease inhibitors, lipoxygenase inhibitors, cytokine antagonists, immunosuppressants, anti-cancer agents, anti-viral agents, cytokines, growth factors, immunomodulators, prostaglandins, anti-vascular hyperproliferation compounds, and the like and combinations thereof. In some embodiments, the compounds or salts, esters, solvates, hydrates, or prodrugs thereof described above and the additional agent may be combined such that administering can be carried out concurrently in, for example, a single oral dose or injection. In other embodiments, the compounds or salts, esters, solvates, hydrates, or prodrugs thereof described above and the additional agent may be administered in separate unit doses either concurrently or at different times throughout the course of treatment.

In certain embodiments the compound(s) and composition(s) disclosed herein may be administered to a patient in need of treatment for a respiratory injury or disease. The respiratory injury or disease is selected from the group consisting of acute and chronic bronchitis, emphysema, respiratory infections (pneumonia, pleurisy), flu (including influenza), post-lung transplant rejection including acute and chronic rejection and bronchiolitis obliterans, acute lung injury or the acute respiratory distress syndrome, pulmonary fibrosis, asthma, cystic fibrosis, and bronchiectasis.

In certain embodiments the compound(s) and composition(s) disclosed herein may be administered to a patient in need of treatment for an injury, disease or conditions selected from myopathy, steroid-induced myopathy, muscular dystrophy, amyotrophic lateral sclerosis (ALS), muscle weakness, critical illness myopathy, muscle atrophy (e.g., disuse muscle atrophy or muscle atrophy in astronauts), muscle wasting (e.g., muscle wasting in the elderly (e.g., age 60 and older)), rhabdomyolysis, dermatomyositis, myositis, mitochondrial myopathy, chronic obstructive lung disease, organ transplant rejection, psoriasis, myasthenia gravis, Addison's disease, celiac disease, Graves' disease, Hashimoto's thyroiditis, or pernicious anemia.

In certain embodiments the compound(s) and composition(s) disclosed herein may be administered to a subject for muscle building in the subject (i.e., use as a muscle building supplement).

In some embodiments, the patient may be administered an effective amount of the compound or salt, ester, solvate, hydrate, or prodrug thereof, which provides relief from inflammation associated with a respiratory disorder. Such relief may be realized based on clinical parameters of assessment (wheezing, respiratory rate, oxygen saturation), objective tests such as a chest radiograph or CT chest scan, pulmonary function tests including arterial blood gases, or exercise tests (6 minute walk test, cardiopulmonary exercise testing). An effective dose can vary depending upon the particular compound, the mode of administration, and severity of the condition being treated. The dosage to be administered in the treatment of a specific individual typically must be subjectively determined by the attending physician who can base the recommended dosage on the size, health, age, and response pattern of the patient and presence of other conditions associated with the patient. Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth. In therapeutic applications, any compound or salt, ester, solvate, hydrate, or prodrug thereof described above can be administered to a patient already suffering from a disease in an amount sufficient to at least partially ameliorate the symptoms of the disease.

In various embodiments, an effective dose can contain from about 0.5 mg to about 500 mg of compound or salt, ester, solvate, hydrate, or prodrug thereof. In particular embodiments, effective dose may include from about 0.75 mg to about 400 mg, about 1 mg to about 300 mg, about 2 mg to about 250 mg, about 5 mg to about 200 mg, about 10 to about 150 mg, or about 20 to about 100 mg of compound or salt, ester, solvate, hydrate, or prodrug thereof or any individual amount or range encompassed by these example ranges. In other embodiments, an effective amount may be determined based on the weight of the patient. For example, administering may include from about 0.5 mg/kg to about 500 mg/kg of the compounds described above or salts, esters, solvates, hydrates, or prodrugs thereof per kg of body weight, and in some embodiments, from about 0.75 mg/kg to about 400 mg/kg, about 1 mg/kg to about 300 mg/kg, about 2 mg/kg to about 250 mg/kg, about 5 mg/kg to about 200 mg/kg, about 10 mg/kg to about 150 mg/kg, or about 20 mg/kg to about 100 mg/kg may be administered to a patient. In certain embodiments, the effective dose of the compounds of the invention or salts, esters, solvates, hydrates, or prodrugs thereof may be administered at a dosage of from about 1 mg/kg to about 10 mg/kg. In still other embodiments, an effective amount may be based on the plasma concentration of the compound or salt, ester, solvate, hydrate, or prodrug thereof after administration. For example, in some embodiments, sufficient compound or salt, ester, solvate, hydrate, or prodrug thereof may be administered to produce a peak plasma concentration of from about 1 µg/mL to about 250 µg/mL, and in other embodiments, a sufficient amount of a pharmaceutical composition may be administered to produce a peak plasma concentration of about 2 µg/mL to about 200 µg/mL, about 3 µg/mL to about 150 µg/mL, about 5µg/mL to about 100 µg/mL, about 5 µg/mL to about 75 µg/mL, or any individual value or range encompassed by these example ranges.

In certain embodiments, the methods described above may include repeating the step of administering. For example, a patient may receive or be instructed to ingest or otherwise self-administer a pharmaceutical composition containing one or more of the compounds or salts, esters, solvates, hydrates, or prodrugs thereof described above once per day for a prescribed time period or two or more times per day for a prescribed period of time. Repeated administration can be carried out for any time period. For example, repeating one or more daily administration of the compounds or salts, esters, solvates, hydrates, or prodrugs thereof described above can be carried out for 3 days to about 1 year, 1 week to about 6 months, 2 weeks to about 3 months, or any time period encompassed by these example ranges.

Administering can be carried out in any manner, for example, administration can be carried out orally, via implants, parenterally (including intravenous, intraperitoneal and subcutaneous injections) either by bolus injection or infusion, rectally, vaginally, transdermally, intratracheally, and so on, using any of the pharmaceutical compositions described above. In embodiments in which the compounds or salts, esters, solvates, hydrates, or prodrugs thereof described above are administered parenterally, solutions, dispersions, or suspensions can be prepared in water suitably mixed with a surfactant such as hydroxyl-propyl-cellulose. In some embodiments, such dispersions or suspensions can be prepared in glycerol, liquid polyethylene glycols, and mixtures thereof in oils.

In some cases, it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compound or salt, ester, solvate, hydrate, or prodrug thereof described above, including the compounds of Formula I and Formula Ia or any of the compounds of Table 1, dissolved, partially dissolved, or suspended in one or more pharmaceutically acceptable solvents and can be administered by, for example, a pump or a squeeze-actuated nebulized spray dispenser. The solvents can be, for example, isotonic saline, PBS, or bacteriostatic water. In such embodiments, the pH of the pharmaceutical composition to be administered may be from about 5.0 to about 7.0. The solid composition can be, by way of illustration, a powder preparation including one or more compound or salt, ester, solvate, hydrate, or prodrug thereof described above intermixed with lactose or other inert powders that are acceptable for intrabronchial use, and can be administered by, for example, an aerosol dispenser or a device that breaks or punctures a capsule encasing the solid composition and delivers the solid composition for inhalation, i.e., blister packs. In some embodiments, inhaled compositions encompassed by the invention may include one or more additional inhaled therapeutic compounds. For example, in certain embodiments, the inhaled compositions may include compounds of Formula I and Formula Ia, any of the compounds of Table 1, or any other compounds disclosed herein, and one or more additional therapeutic compound such as, for example, bronchodilators such as β2 agonists (SABA/LABA) such as salmeterol, terbutaline, salbutamol, levosalbutamol, pirbuterol, bambuterol, fenoterol, metalproterenol, and formoterol, other bronchodilators such as epinephrine, racemic epinephrine, ephedrine, clenbuterol, indacaterol, vilanterol, and theophylline; corticosteroids such as beclomethasone, budesonide, ciclesonide, flunisolide, fluticasone and triamcinolone, anticholinergics such as ipratropium and tiotropium, anti-inflammatories such as cromolyn and nedocromil, and the like and various combinations thereof. The aerosol composition can include, by way of illustration, one or more compound or salt, ester, solvate, hydrate, or prodrug thereof described above, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable. The dosage of the compounds of the invention administered directly to the respiratory system of the patient by, for example, inhalation may be similar to the dosage administered systemically.

In certain embodiments, the compounds or compositions disclosed herein may be administered via intratracheal delivery, with or without co-administration of a bronchodilator such as β2 agonists (SABA/LABA) such as salmeterol, terbutaline, salbutamol, levosalbutamol, pirbuterol, bambuterol, fenoterol, metalproterenol, and formoterol, other bronchodilators such as epinephrine, racemic epinephrine, ephedrine, clenbuterol, indacaterol, vilanterol, and theophyllines; corticosteroids such as beclomethasone, budesonide, ciclesonide, flunisolide, fluticasone and triamcinolone, anticholinergics such as ipratropium and tiotropium, anti-inflammatories such as cromolyn and nedocromil, and the like and various combinations thereof.

Compounds described herein can be administered transdermally, i.e., administered across the surface of the body and the inner linings of bodily passages including epithelial and mucosal tissues. Administering transdermally can be carried out by applying any of the compounds or salts, esters, solvates, hydrates, or prodrugs thereof to a surface of the body in, for example, lotions, creams, foams, patches, suspensions, solutions, and suppositories (rectal and vaginal). In some embodiments, transdermal administration can be accomplished through the use of a transdermal patch containing a compound and a carrier that is inert to the compound, non-toxic to the skin, and combine with the compound to allow the compound to be absorbed into the blood stream for systemic delivery. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

In particular embodiments, Compound 014 may be administered to a patient in need of treatment. While Compound 014 can be administered in any amount described above, in any dosage form described above, or any administration route described above, in some embodiments, less Compound 014 may be necessary to provide treatment. As discussed above with regard to pharmaceutical compositions containing Compound 014, the data presented in FIG. 1 suggests that less than about half the amount of Compound 014 is necessary to achieve maximum inhibition of IL1β than the structurally similar compounds, and significantly less Compound 014 may be necessary to achieve efficacy when Compound 014 is administered to a patient as compared to structurally similar compounds. Therefore, Compound 014 may be administered at lower doses, less frequently, at reduced infusion or bolus injection volume, and at smaller oral dose and the like while producing fewer side effects.

Additional embodiments are directed to methods for making the compounds or salts, esters, solvates, hydrates, or prodrugs thereof described above. Synthetic methods for the compounds described above may vary among embodiments and can encompass any number of steps, utilize various catalysts, solvents, purification procedures, and so on while falling within the scope of the invention. For example, as illustrated in Scheme I below in some embodiments, the compounds of the invention can be made by combining an aldehyde containing benzene with a alkylene diamine in a solvent such as anhydrous ethanol and heating this solution under reflux until the solvent has evaporated resulting in formation of a Schiff base. The Schiff base can then be isolated and washed before being dissolved in a second solvent such as absolute methanol to create a second solution to which a reducing agent such as sodium borohydride can be added which reduces the Schiff base to secondary amine. The secondary amine containing compound can be isolated and washed or purified to produce the compounds of the invention.

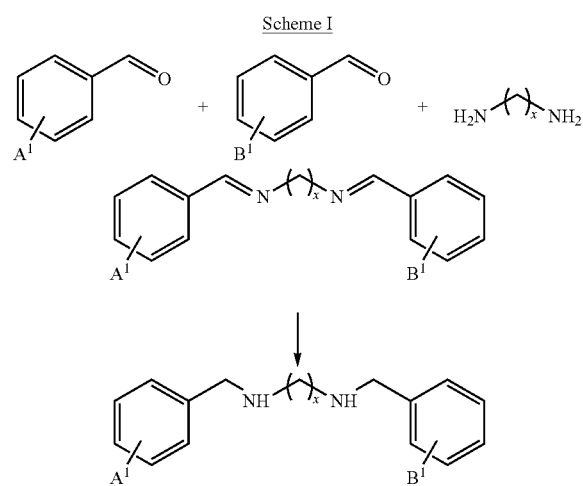

Scheme I

In Scheme I, each $A^1$ and $B^1$ may, independently, be a cyclohexyl, phenyl, 6-membered heteroaryl, 6-membered heterocycloalkyl, cyclopentyl, cyclopentene, cyclopentadiene, 5-membered heteroaryl, 5-membered heterocycloalkyl each of which may be substituted with one or more $R^g$ groups as described above with reference to A and B in Formulae I and Ia. In particular embodiments, A and B can be any of the 6-membered heteroaryl, 6-membered heterocycloalkyl, 5-membered heteroaryl, and 5-membered heterocycloalkyl substituents described above, and in certain embodiments, $A^1$ and $B^1$ may be the same. As in Formulae I and Ia, x may be an integer of from 1 to 10, or 2 to 10, 2 to 8, or 2 to 6, and in particular embodiments, x may be 2. Additionally, while the benzaldehyde is represented as an aldehyde containing benzene in Scheme I, any aldehyde containing benzene can be used. For example, 2-phenylacetaldehyde, 3-phenylpropanal, 4-phenylbutanal, and the like compounds substituted with an $A^1$ or $B^1$ substituent can be used in various embodiments.

In particular embodiments, methods for making the compounds of the invention may further include the step of preparing a salt form of the compound prepared as described above. In such embodiments, the method may include dissolving an isolated form of the secondary amine in a solution and adding an ionizing compound to the solution. Various ionizing compounds are known in the art and include, but are not limited to, hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. For example, in certain embodiments, the secondary amine containing compound may be dissolved in water and concentrated hydrochloric acid or sodium acetate may be added to the solution until the salt form of the compound crystallizes out of the solution. Such method may further include the steps of isolating the crystalline compound, washing the crystals, and redissolving or compounding the crystals.

Methods for making pharmaceutical compositions may include the steps of dissolving the compounds produced as described above in sterile a solution, such as water, saline, Ringer's solution, or an appropriate oil. In other embodiments, methods for making pharmaceutical compositions may include combining or compounding solid, powdered, or crystalline forms of the compounds produced as described above with powdered carriers and excipients, and pressing the mixtures into tablets. In still other embodiments, methods for making pharmaceutical compositions may include the step of forming microparticles or nanoparticles including the compounds produced as described above and encapsulating these microparticles or nanoparticles in a capsule or tablet. In further embodiments, such methods may further include incorporating one or more additional components such as flavoring agents, lubricants, solubilizers, suspending agents, fillers, glidants, compression aids, binders or tablet-disintegrating agents, or various encapsulating materials as discussed above into the various pharmaceutical compositions, and in certain embodiments, such additional agents may be added before pressing the mixtures into tablets or forming or encapsulating microparticles or nanoparticles.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

Example 1

Compound Synthesis

Compound 001: 4-(4-Morpholinyl)benzaldehyde (0.01 mol, 1.91 g) was added to a solution of ethylenediamine (0.005 mol, ~350 ul) in anhydrous ethanol (20 ml), and the resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of Compound 001 were collected, washed with water and dried, followed by recrystallization from ethyl acetate.

Compound 002: 4-(1-Pyrrolidino)-benzaldehyde (0.01 mol, 1.75 g) was added to a solution of ethylenediamine (0.005 mol, ~350 ul) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of Compound 002 were collected, washed with water and dried, followed by recrystallization from ethyl acetate.

Compound 003: 4-(1H-Imidazol-1-yl)benzaldehyde (0.01 mol, 1.72 g) was added to a solution of ethylenediamine (0.005 mol, ~350 ul) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of Compound 003 were collected, washed with water and dried, followed by recrystallization from ethyl acetate.

Compound 004: 4-(1-Piperidinyl)benzaldehyde (0.01 mol, 1.89 g) was added to a solution of ethylenediamine (0.005 mol, ~350 ul) in anhydrous ethanol (20 ml). The resulting solution was refluxed and stirred for 30 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of Compound 004 were collected, washed with water and dried, followed by recrystallization from ethyl acetate.

Compound 005: 4-(2-Pyridinyl)benzaldehyde(0.01 mol, 1.83 g) were added to a solution of ethylenediamine (0.005 mol, ~350 ul) in anhydrous ethanol (20 ml). The resulting solution was heated and stirred for 30 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of Compound 005 were collected, washed with water and dried, followed by recrystallization from ethyl acetate.

Compound 006: 4-(1-Pyrrolidino)-benzaldehyde (0.01 mol, 1.75 g) was added to a solution of 1,4-Diaminobutane (0.005 mol, 0.44 g) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of Compound 006 were collected, washed with water and dried, followed by recrystallization from ethyl acetate.

Compound 007: 4-(1-Pyrrolidino)-benzaldehyde (0.01 mol, 1.75 g) was added to a solution of 1,3-Diaminopropane (0.005 mol, 0.37 g) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of Compound 007 were collected, washed with water and dried, followed by recrystallization from ethyl acetate.

Compound 008: 4-(2-Pyridinyl)benzaldehyde(0.005 mol, 0.92 g), 2-Pyridinecarboxaldehyde (0.005 mol, 0.53 g) was added to a solution of ethylenediamine (0.005 mol, ~350 ul) in anhydrous ethanol (20 ml). The resulting solution was refluxed and stirred for 60 min The reaction was cooled down until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of Compound 008 were collected, washed with water and dried, followed by recrystallization from ethyl acetate.

Compound 009: 4-(1H-Pyrazol-1-yl)benzaldehyde (0.004 mol, 0.7 g) was added to a solution of ethylenediamine (0.002 mol, ~140 ul) in anhydrous ethanol (10 ml). The resulting solution was heated and stirred for 20 min until the precipitation of the relevant Schiff base. The Schiff bases were filtered off, and washed with cold ethanol. The Schiff base was then added to 15 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine. The precipitation of Compound 009 were collected, washed with water and dried, followed by recrystallization from ethyl acetate.

Compound 010: 4-(2-Pyridinyl)benzaidehyde(0.01 mol, 1.83 g) was added to a solution of 1,4-Diaminobutane (0.005 mol, 0.44 g) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of Compound 010 were collected, washed with water and dried, followed by recrystallization from ethyl acetate.

Compound 011: 4-(1,3-Thiazol-2-yl)benzaidehyde (0.004 mol, 0.76 g) was added to a solution of ethylenediamine (0.002 mol, ~140 ul) in anhydrous ethanol (20 ml). The resulting solution was heated and stirred for 20 min until the precipitation of the relevant Schiff base. The Schiff bases were filtered off, and washed with cold ethanol. The Schiff base was then added to 15 ml absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine. The precipitation of Compound 011 were collected, washed with water and dried, followed by recrystallization from ethyl acetate.

Compound 012: 4-2-Thienyl)benzaldehyde (0.004 mol, 0.76 g) was added to a solution of ethylenediamine (0.002 mol, ~140 ul) in anhydrous ethanol (20 ml). The resulting solution was heated and stirred for 40 min until the precipitation of the relevant Schiff base. The Schiff bases were filtered off, and washed with cold ethanol. The Schiff base was then added to 15 ml absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine. The precipitation of Compound 012 were collected, washed with water and dried, followed by recrystallization from ethyl acetate.

Compound 013: 4-(2-furyl)benzaldehyde (0.004 mol, 0.69 g) was added to a solution of ethylenediamine (0.002 mol, ~140 ul) in anhydrous ethanol (20 ml). The resulting solution was heated and stirred for 40 min until the precipitation of the relevant Schiff base. The Schiff bases were filtered off, and washed with cold ethanol. The Schiff base was then added to 15 ml absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine. The precipitation of Compound 013 were collected, washed with water and dried, followed by recrystallization from ethyl acetate.

Compound 014: 4-(pyrimidin-2-yl)benzaldehyde (0.004 mol, 0.74 g) was added to a solution of ethylenediamine (0.002 mol, ~140 ul) in anhydrous ethanol (20 ml). The resulting solution was heated and stirred for 30 min until the precipitation of the relevant Schiff base. The Schiff bases were filtered off, and washed with cold ethanol. The Schiff base was then added to 15 ml absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine. The precipitation of Compound 014 were collected, washed with water and dried, followed by recrystallization from ethyl acetate.

Compound 015: 4-Phenylbenzaldehyde (0.004 mol, 0.73 g) were added to a solution of ethylenediamine (0.002 mol, ~140 ul) in anhydrous ethanol (20 ml). The resulting solution was heated and stirred for 20 min until the precipitation of the relevant Schiff base. The Schiff bases were filtered off, and washed with cold ethanol. The Schiff base was then added to 15 ml absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine. The precipitation of Compound 015 were collected, washed with water and dried, followed by recrystallization from ethyl acetate.

Example 2

Therapeutic Index Formula I Compounds

Peripheral blood mononuclear cells (PBMC) (0.2 ml at 0.3×106/ml) were treated with lipopolysaccharide (LPS) (50 ng/ml) for 16 hours concurrently with each compound tested at different concentrations. TNFα cytokine release was monitored by ELISA. These concentrations were used to calculate the IC50.

U937 monocytes (0.2 ml at 0.3 x 106/ml) were treated with each compound at different concentrations for 16 hours. The cells were then stained with Trypan blue to identify dead cells, and to calculate the LC50. Combined values were used to generate therapeutic indexes (TI)=LC50/IC50.

FIG. 1 provides examples of data resulting from IC50 and LD50 tests described above for benzathine (FIG. 1A), Compound 014 (FIG. 1B) Compound 004 (FIG. 1C), Compound 005 (FIG. 1D), Compound 010 (FIG. 1E), and Compound 015 (FIG. 1F). Similar tests were carried out for each of the compounds presented in TABLE 1. The results are presented in TABLE 2:

TABLE 2

| Compound | IC50 (µg/ml) | LC50 (µg/ml) | TI |
| --- | --- | --- | --- |
| Benzathine | 25 | 400 | 16 |
| Compound 001 | 20 | 260 | 13 |
| Compound 002 | 0.6 | 7 | 11 |
| Compound 003 | 0.7 | 130 | 142 |
| Compound 004 | 0.8 | 27 | 33 |
| Compound 005 | 0.9 | 87 | 96 |
| Compound 006 | 1 | 1 | 1 |
| Compound 007 | 1.1 | 3.2 | 2.9 |
| Compound 008 | 1.5 | 45 | 30 |
| Compound 009 | 1.4 | 80 | 57 |
| Compound 010 | 1.5 | 22 | 14.7 |
| Compound 011 | 0.4 | 8.5 | 21.3 |
| Compound 012 | 1.1 | 1.8 | 1.6 |
| Compound 013 | 1.9 | 5.5 | 2.8 |
| Compound 014 | 0.4 | 410 | 1025 |
| Compound 015 | 2 | 2 | 1 |
| Compound 016 | 4 | >100 | >25 |
| Compound 017 | 0.2 | 4 | 20 |
| Compound 018 | 0.1 | 0.4 | 4 |
| Compound 019 | 0.5 | 1 | 2 |
| Compound 020 | 0.2 | 2 | 10 |
| Compound 021 | 0.4 | 1 | 2.5 |

These data show that compounds of Formula I exhibit good anti-cytokine activity (IC50) with relatively low toxicity (LC50). In particular, compounds of Formula I having pyrimidine substitutions appear to provide excellent high activity and very low toxicity.

Example 3

Compound 005 Reduces Lung Injury in *Pseudomonas* Induced Pneumonia.

Mice were administered 100 ug of Compound 005 by IP injection, and these mice were then challenged with *Pseudomonas aeruginosa* strain PA103 ($10^4$ CFU/mouse, i.t.) for 18 hours. Mice were monitored on a FlexiVent to measure lung mechanics throughout the procedure. The mice were then sacrificed and lungs were lavaged with saline, harvested, and then homogenized. Lavage protein, cell count and cytokine secretion, was measured H&E staining was performed on lung samples. (n=4-6 mice/group, *p<0.05 versus Vehicle)

Figure 3A:
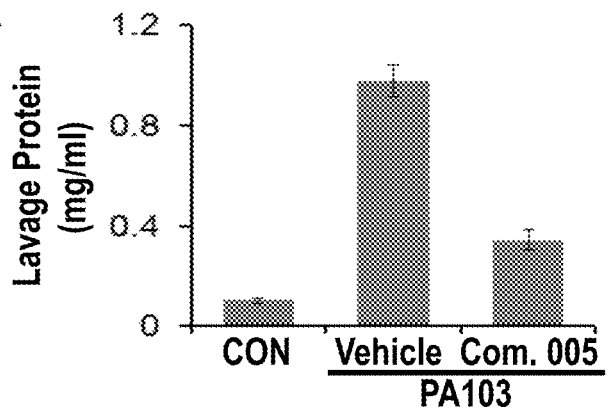
FIGS. 3A-3C show representative data, including lavage protein concentration (FIG. 3A), lavage cell concentration (FIG. 3B), and relative cytokine concentrations (FIG. 3C) for mice treated with Compound 005 and challenged with *Pseudomonas aeruginosa* strain PA103 compared to untreated and unchallenged mice.
Figure 3B:
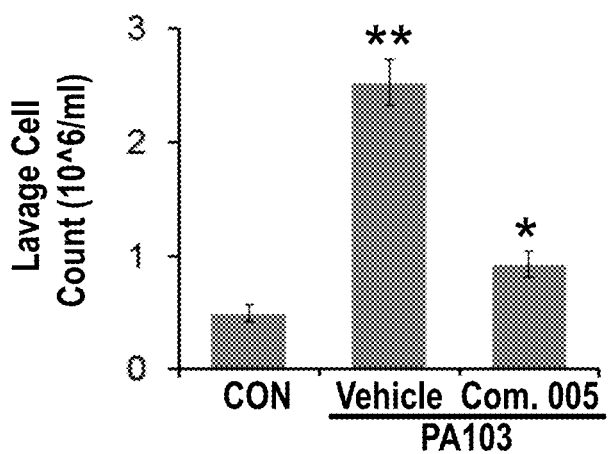
Figure 3C:
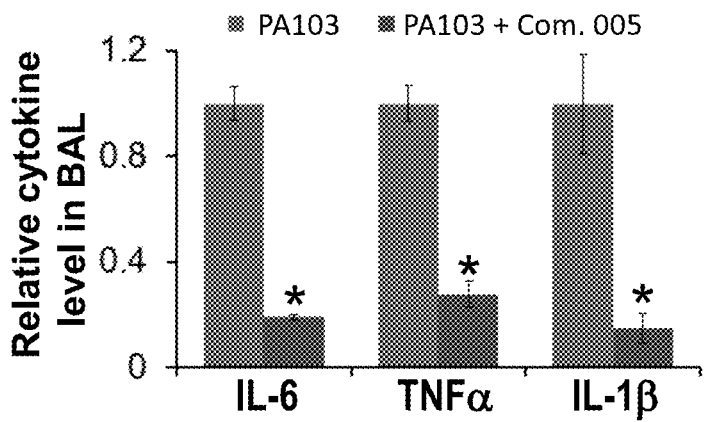
Figure 4:
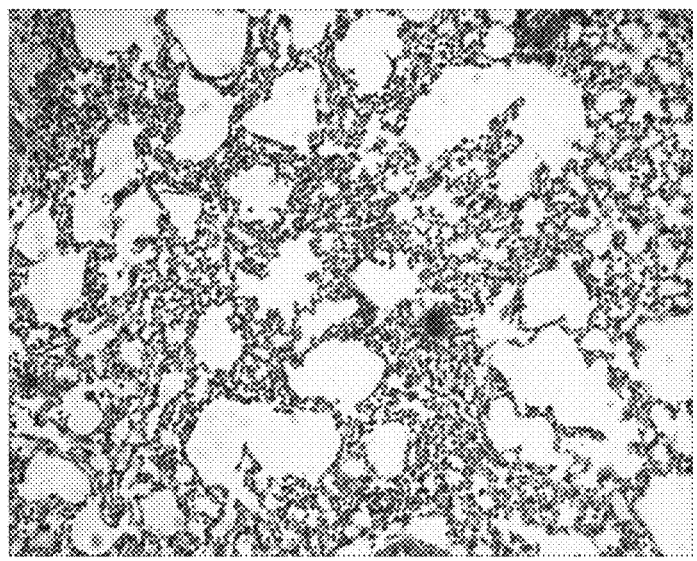
FIG. 4 shows micrographs of lung tissue for mice treated with Compound 005 and challenged with *Pseudomonas aeruginosa* strain PA103 (PA103+005) compared to untreated challenged mice (PA103+Vehicle).
Figure 4:
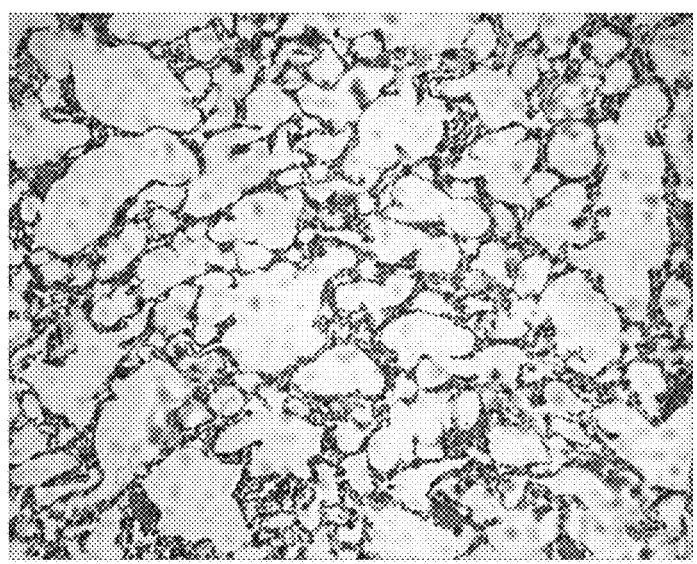

Compound 005 significantly ameliorated adverse effects of *Pseudomonas* on lung mechanics As illustrated in FIG. 2A-D, Compound 005 decreased lung resistance (FIG. 2A), reduced elastance (FIG. 2B), increased compliance (FIG. 2C), and improved lung volume (FIG. 2D) compared to untreated, vehicle only mice resulting in resistance, elastance, compliance, and lung volumes that were nearly equal to unchallenged controls. In addition, lavage protein concentration (FIG. 3A), lavage cell counts (FIG. 3B), and lavage pro-inflammatory cytokine levels were significantly decreased in PA103 infected mice (FIG. 3C), and cell infiltrates were significantly reduced in treated PA103 infected mice as compared to untreated, vehicle only mice as indicated by H&E staining (FIG. 4).

Example 4

Compound 005 Ameliorates H1N1 Influenza Induced Lung Injury.

Mice were challenged with H1N1 ($10^5$ PFU/mouse, i.t.) and observed for 9 d. For Compound 005 treated mice, a stock solution (5 mg/ml) of Compound 005 was added to drinking water (containing 2% sucrose) to the final concentration of 30 ug/ml. Mice were carefully monitored, and moribund, preterminal animals were immediately euthanized and recorded as deceased. Lung mechanics were measured at day 5 using a FlexiVent. Mice were then sacrificed, their lungs were photographed, and lungs were lavaged with saline, harvested, and then homogenized, and H&E staining was performed on lung samples. (n=5-8 mice/group, *p<0.05 versus H1N1)

Figure 5:
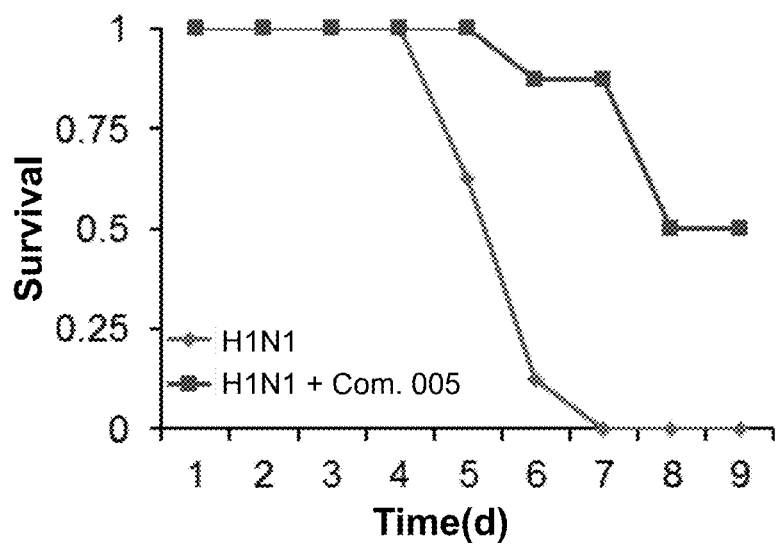
FIG. 5 is a graph depicting representative survival rates for mice treated with Compound 005 and challenged with H1N1 compared to untreated, challenged mice.
Figure 6A:
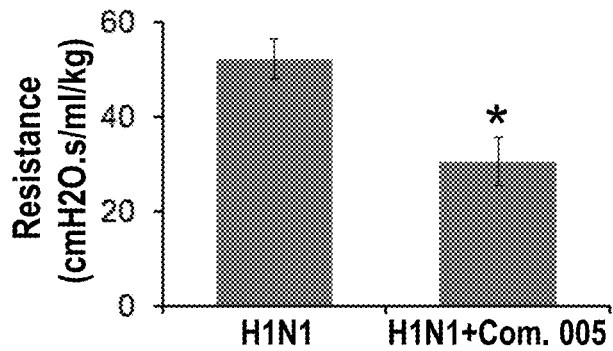
FIG. 6A-6C show representative data, including lung resistance (FIG. 6A), lung elastance (FIG. 6B), and lung compliance (FIG. 6C), for mice treated with Compound 005 and challenged with H1N1 compared to untreated, challenged mice and unchallenged, control mice.
Figure 6B:
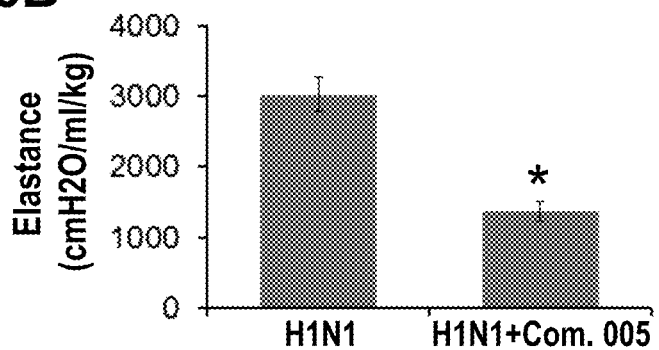
Figure 6C:
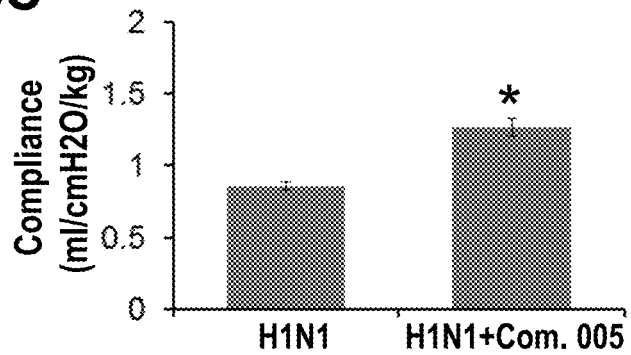
Figure 7A:
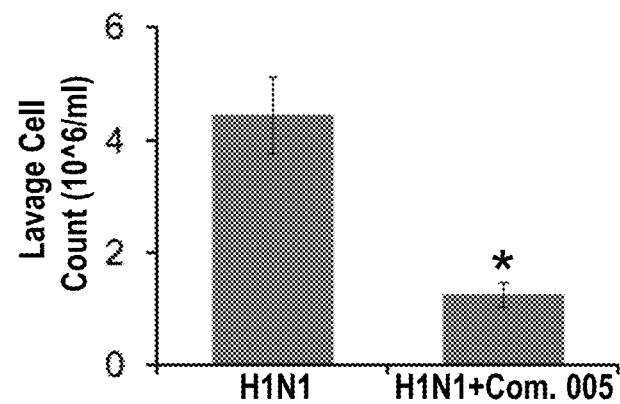
FIGS. 7A-7B show representative data, including lavage protein concentration (FIG. 7A) and lavage cell concentration (FIG. 7B) for mice treated with Compound 005 and challenged with H1N1 compared to untreated, challenged mice and unchallenged, control mice.
Figure 7B:
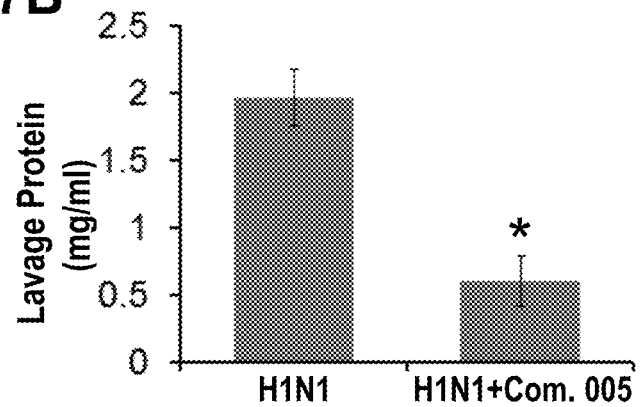
Figure 8A:
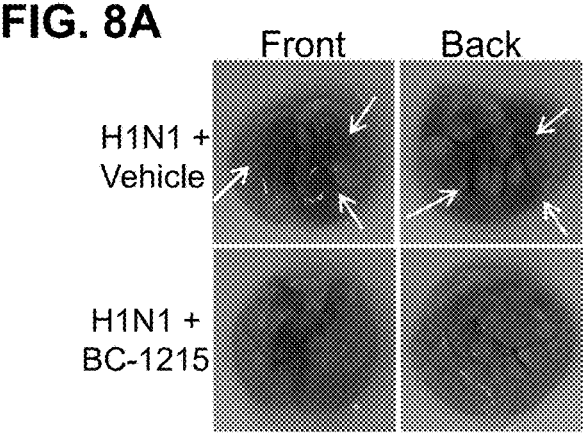
FIGS. 8A-8B show photographs of lung tissue for mice treated with Compound 005 and challenged with H1N1 (H1N1+005) compared to untreated, challenged mice (H1N1+Vehicle)
Figure 8B:
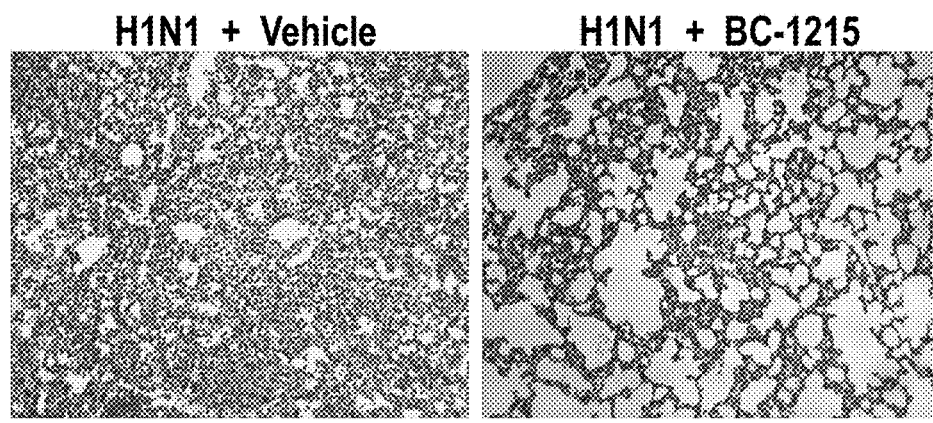

Initially, Compound 005 treated mice showed significantly increased survival rate compared to untreated infected mice (FIG. 5). Additionally, like the PA103 in Example 2, H1N1 challenged mice that were treated with Compound 005 exhibited decreased lung resistance (FIG. 6A), reduced elastance (FIG. 6B), and increased compliance (FIG. 6C). Compound 005 mice also exhibited decreased lavage protein concentration (FIG. 7A) and lavage cell counts (FIG. 7B). Photographs of lungs from treated mice appeared exhibited less lung edema than lungs from untreated, vehicle only mice (FIG. 8A), and H&E staining showed fewer cell infiltrates (FIG. 8B). Thus, Compound 005 treated lungs appeared more healthy after challenge by H1N1 treated mice both visually and biochemically.

Example 5

Compound 014 Reduces Lung Injury in *Pseudomonas* Induced Pneumonia.

Mice were administered either 30 μg or 150 μg of Compound 014 by IP injection, and these mice were then challenged with *Pseudomonas aeruginosa* strain PA103 ($2.5 \times 10^4$ CFU/mouse, i.t.) for 18 hours. Mice were monitored on a FlexiVent to measure lung mechanics throughout the procedure. The mice were then sacrificed and lungs were lavaged with saline, harvested, and then homogenized. Lavage cells were processed with cytosin and stained with May-Grunwald and Geimsa, and H&E staining was performed on lung samples. Lavage protein, cell count, and cytokine secretion were measured. (n=4 mice/group, *P<0.05 versus PA103 versus Vehicle)

Figure 9A:
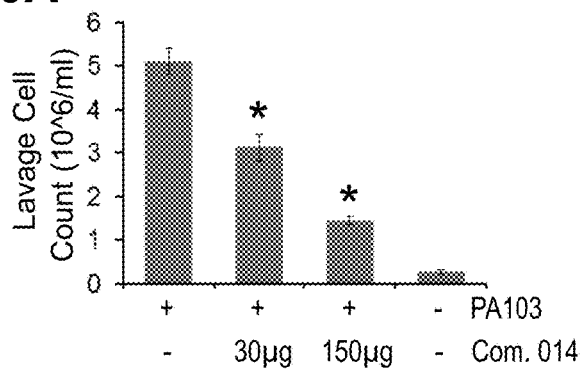
FIGS. 9A-9C show representative data, including lavage protein concentration (FIG. 9A), lavage cell concentration (FIG. 9B), and relative cytokine concentrations (FIG. 9C) for mice treated with 30 µg or 150 µg of Compound 014 and challenged with *Pseudomonas aeruginosa* strain PA103 compared to untreated, challenged mice and unchallenged, control mice.
Figure 9B:
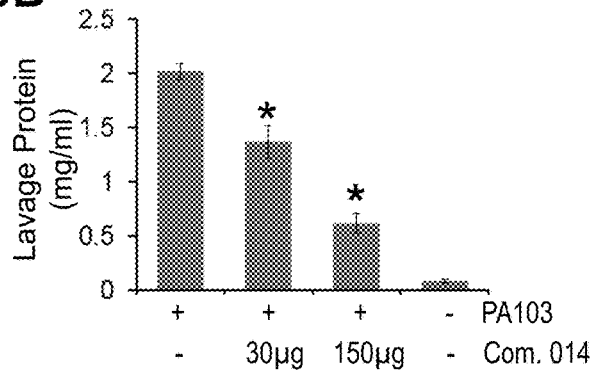
Figure 9C:
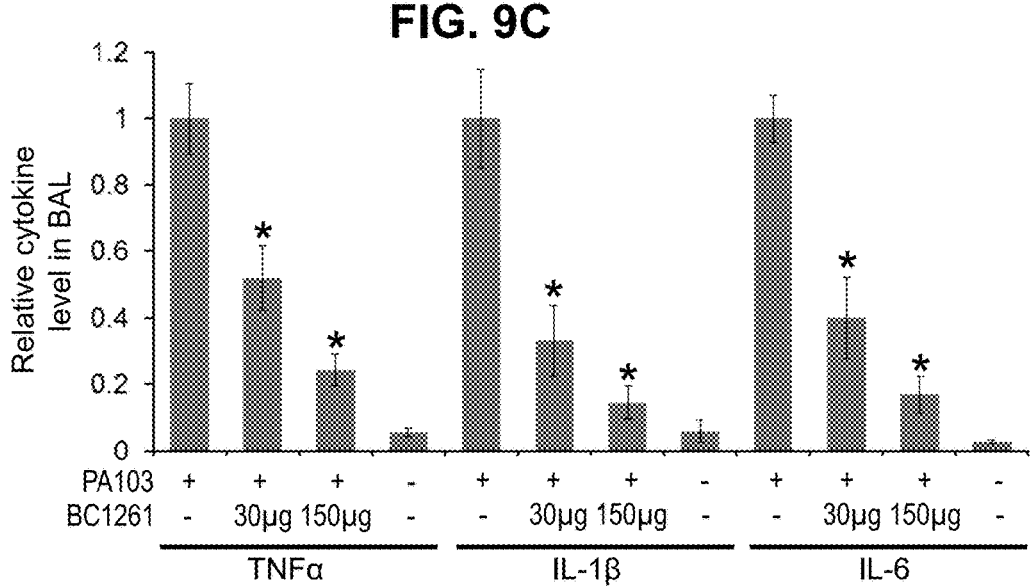
Figure 10:
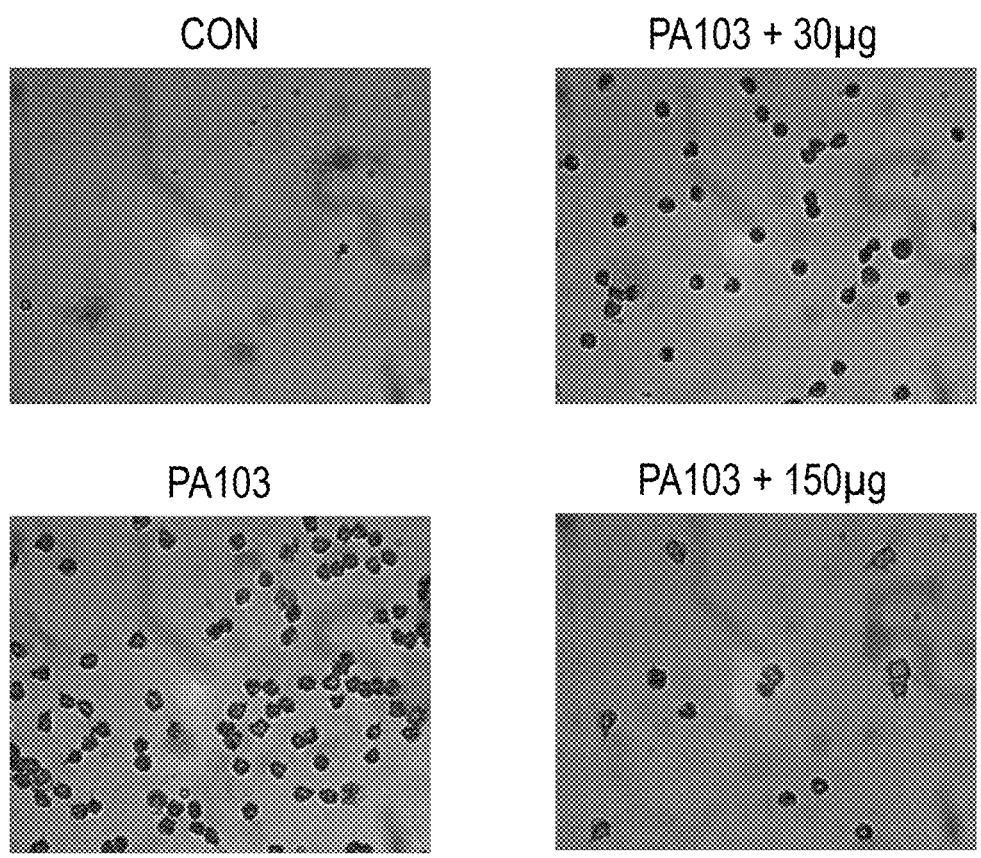
FIG. 10 shows micrographs of lung tissue from mice treated with 30 µg (PA103+30 µg) or 150 µg (PA103+150µg) of Compound 014 and challenged with *Pseudomonas aeruginosa* strain PA103 compared to untreated, challenged mice (PA103) and unchallenged, control mice (CON) that were processed with cytosin and stained with May-Grunwald and Geimsa.
Figure 11:
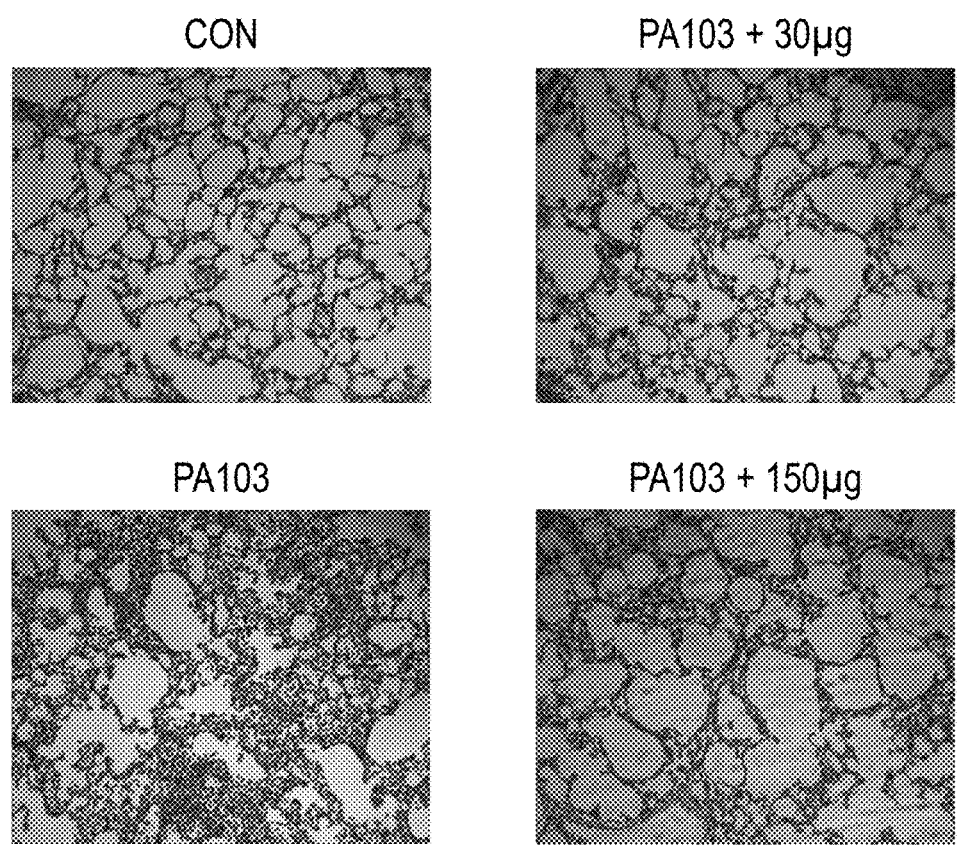
FIG. 11 shows micrographs of lung tissue from mice treated with 30 µg (PA103+30 µg) or 150 µg (PA103+150 µg) of Compound 014 and challenged with *Pseudomonas aeruginosa* strain PA103 compared to untreated, challenged mice (PA103) and unchallenged, control mice (CON).

Compound 014 significantly ameliorated adverse effects of *Pseudomonas* on lung mechanics Mice treated with Compound 0014 exhibited reduced lavage cell counts (FIG. 9A) and reduced lavage protein concentration (FIG. 9B), as well as a reduction in lavage pro-inflammatory cytokine levels (FIG. 9C) compared to untreated, vehicle control infected mice. In addition significantly fewer neutrophils were evident in May-Grunwald and Geimsa smears for mice treated with Compound 014 when compared to untreated, vehicle control smears (FIG. 10), and cell infiltrates were significantly reduced in treated PA103 infected mice as compared to untreated, vehicle control mice as indicated by H&E staining (FIG. 11).

Example 6

Compound 0014 Reduces Smoke Induced Chronic Lung Inflammation.

Mice were exposed to cigarette smoke for 5 weeks before a single 100 ug dose of Compound 014 was administered by i.p. injection. The mice were euthanized 18 hours later, and lungs were lavaged with saline, harvested, and then homogenized. Lavage protein, cell counts and cytokine secretion were measured. (n=3 mice/group, *P<0.05 versus control)

Figure 12A:
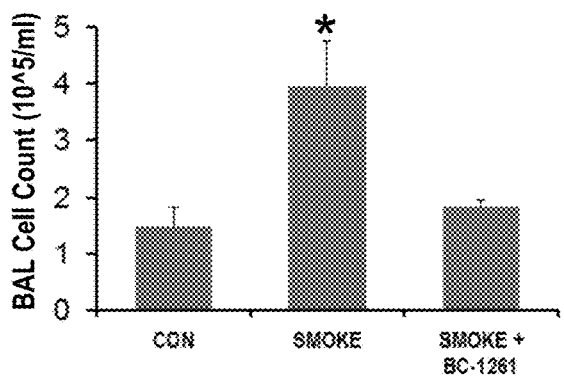
FIGS. 12A-12C show representative data, including lavage protein concentration (FIG. 12A), lavage cell concentration (FIG. 12B), and relative cytokine concentrations (FIG. 12C) for mice treated with Compound 014 after being exposed to cigarette smoke or 5 weeks compared to untreated, challenged mice and unchallenged, control mice.
Figure 12B:
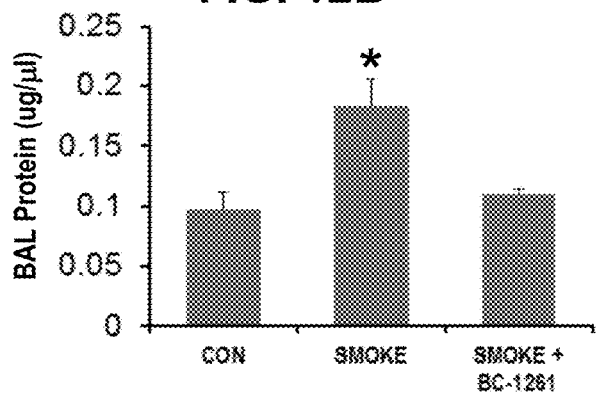
Figure 12C:
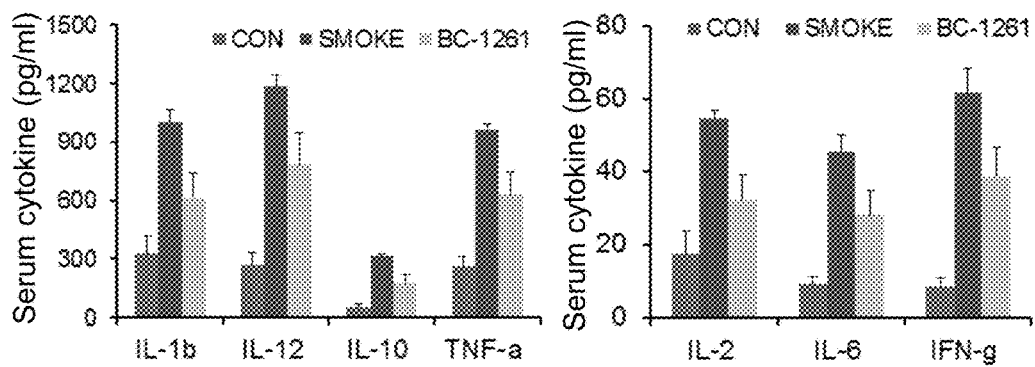
Figure 13:
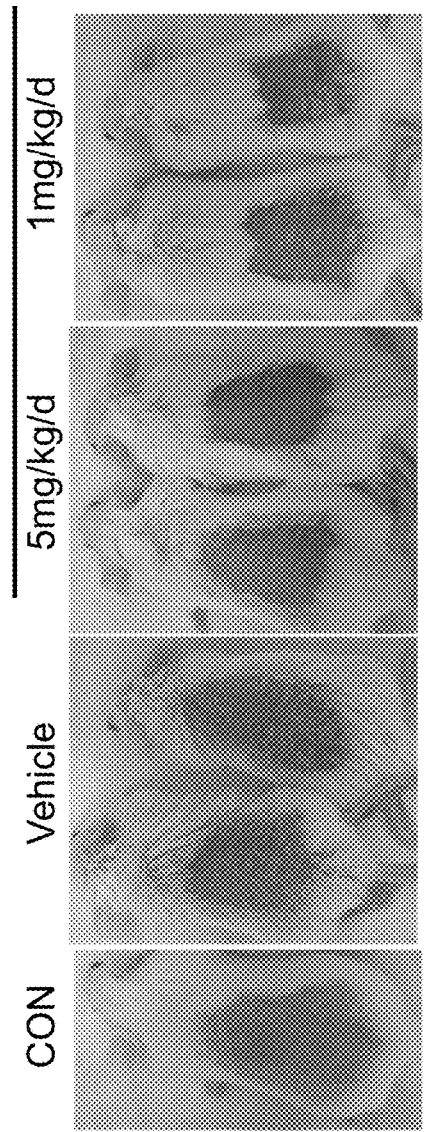
FIG. 13 shows gross images of the back of the BALB/C mice treated with IMQ (3.125 mg/d topical). Compound 014 were either given in drinking water or applied topically daily.
Figure 13:
Figure 14:
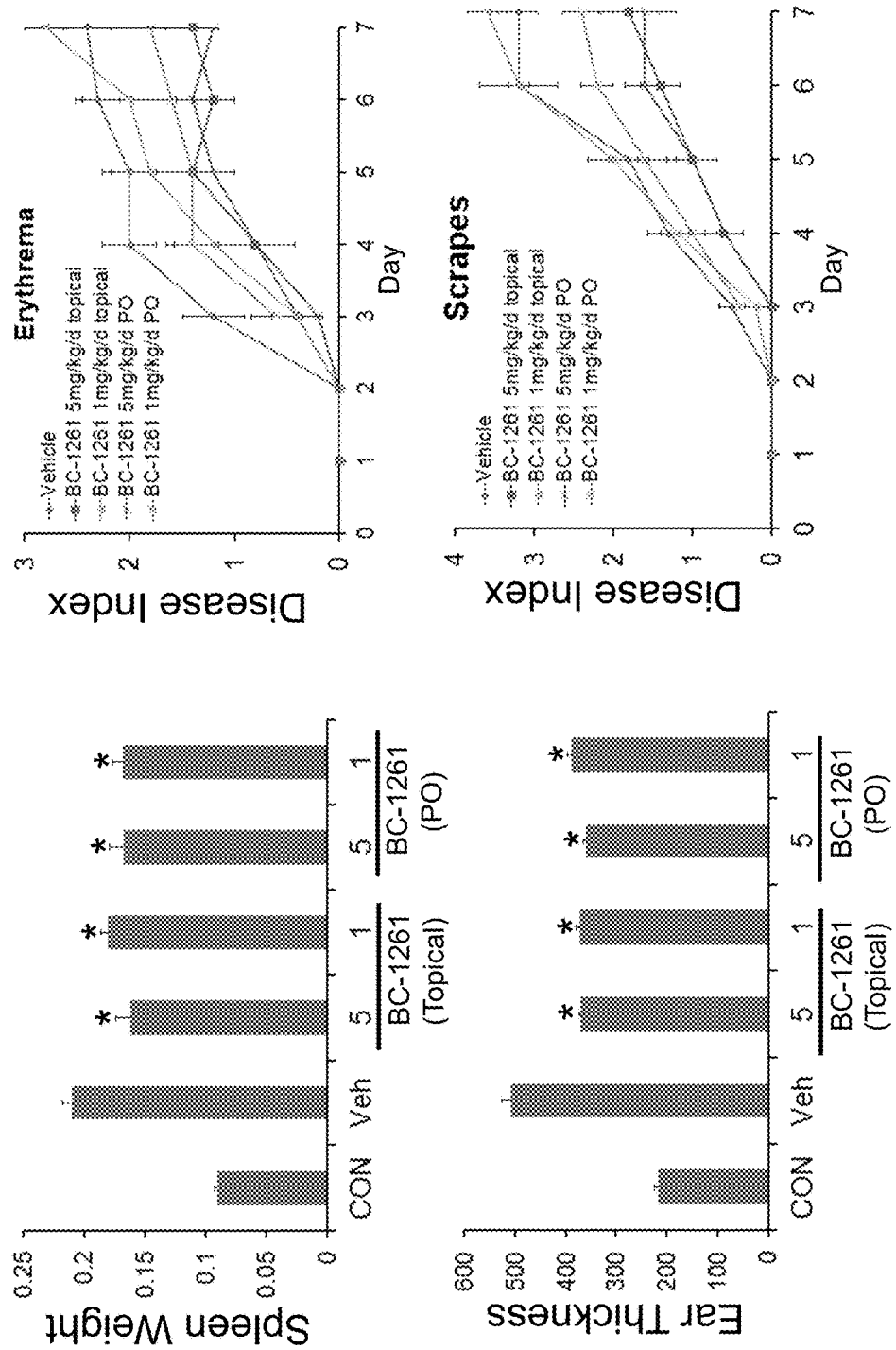
FIG. 14 shows the severity of inflammation of the back skin. An objective scoring system was developed based on the clinical Psoriasis Area and Severity Index (PASI), except that for the mouse model the affected skin area is not taken into account in the overall score. Erythema and scaling were scored independently on a scale from 0 to 4: 0, none; 1, slight; 2, moderate; 3, marked; 4, very marked. The level of erythema was scored using a scoring table with red taints. At day 7, mice were euthanized and spleens were removed for weight measuring.
Figure 15:
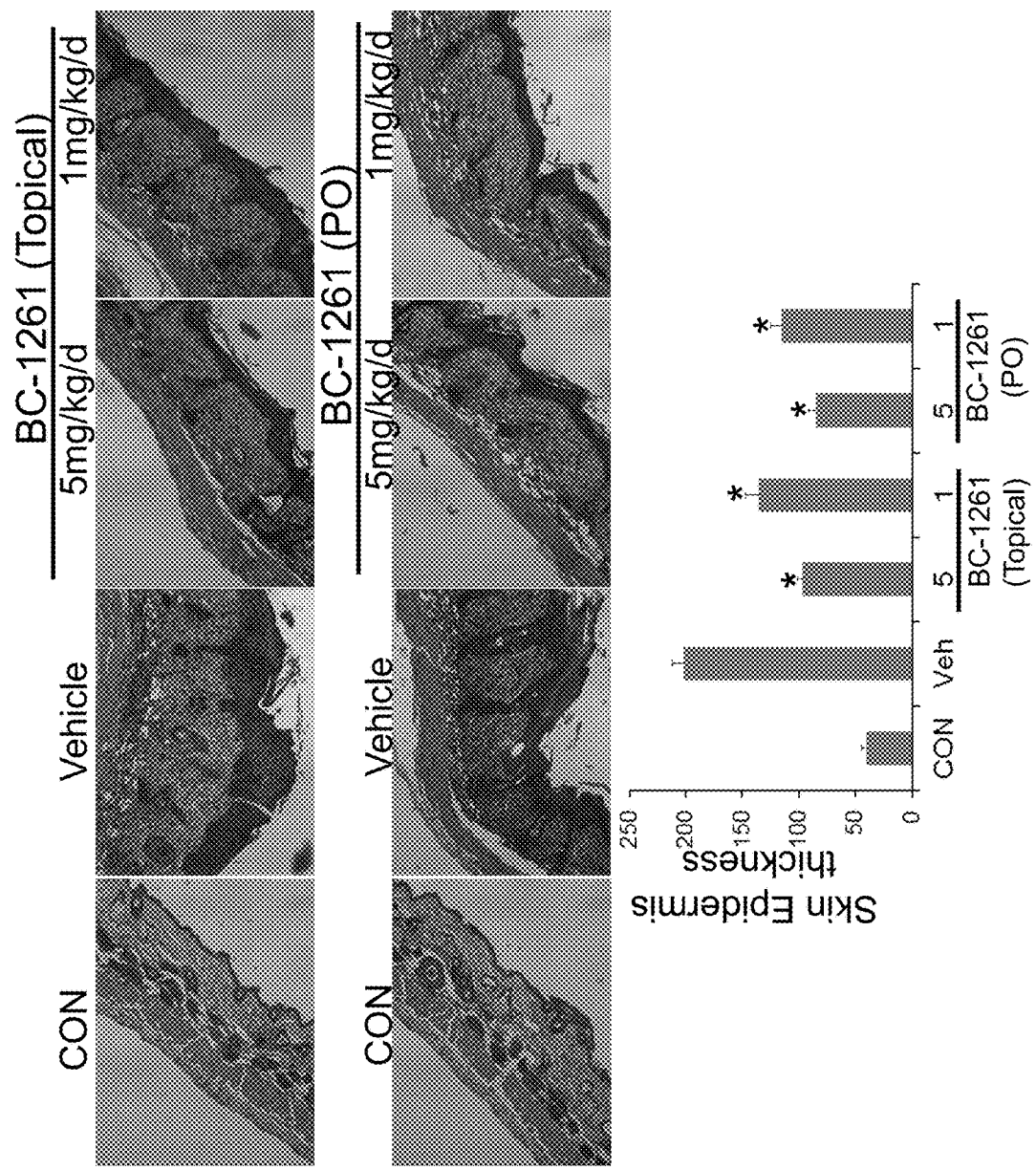
FIG. 15 shows the H&E staining from the skin sample and epidermis thickness were measured and graphed.
Figure 16:
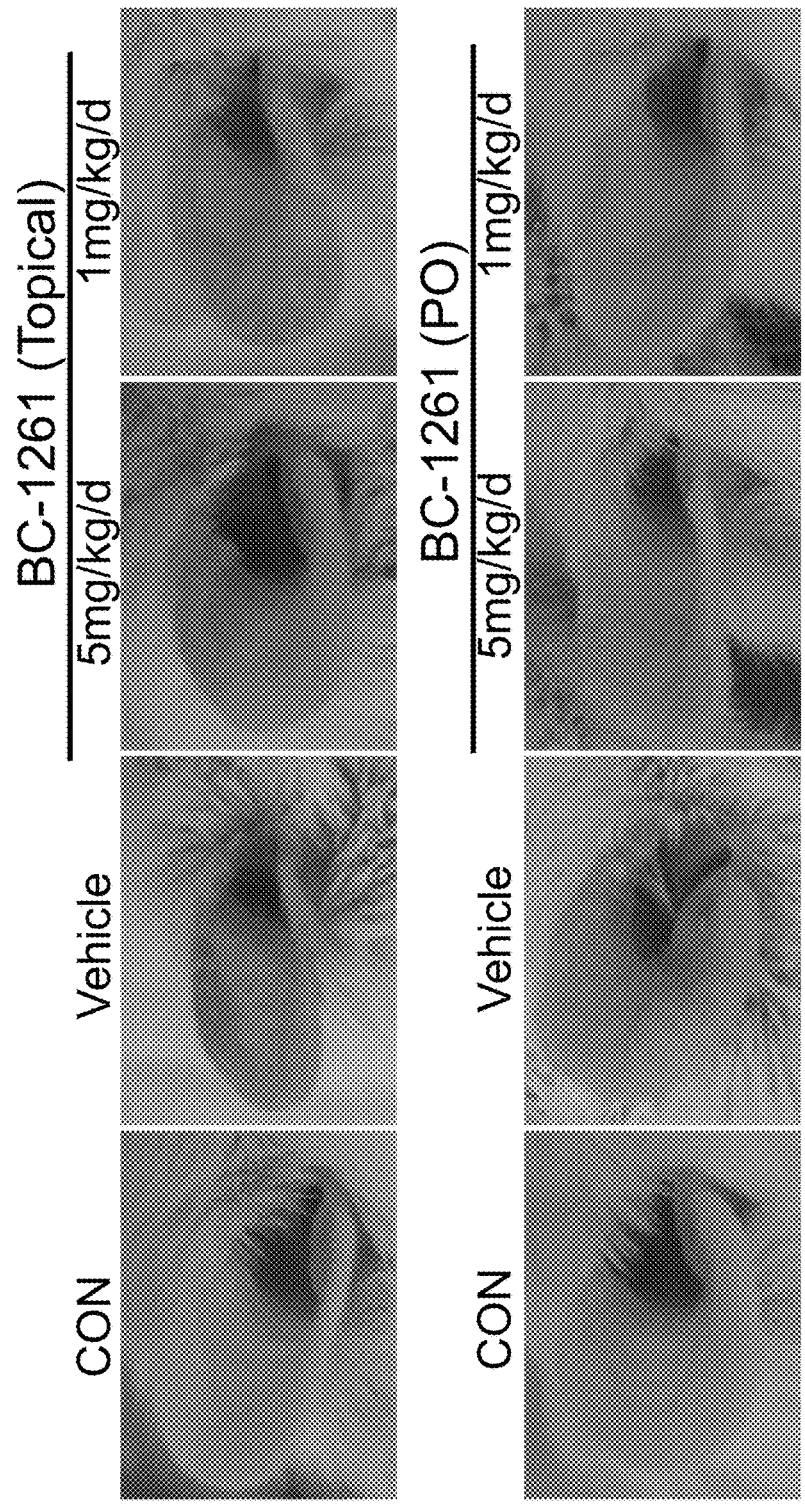
FIG. 16 shows gross images of the ears of the BALB/C mice treated with IMQ (3.125 mg/d topical). Compound 014 were either given in drinking water or applied topically daily.
Figure 17:
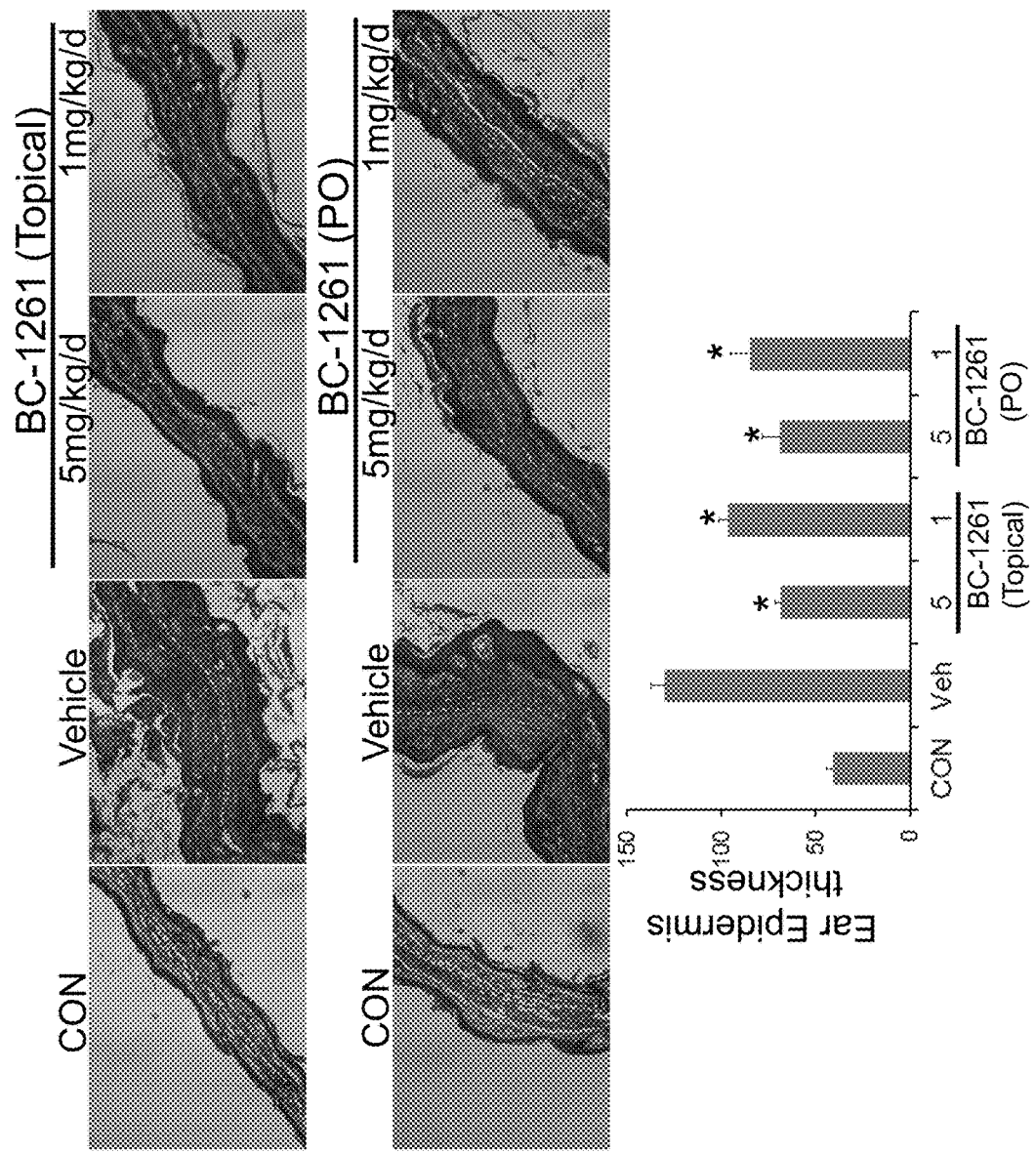
FIG. 17 shows the H&E staining from the ear samples and epidermis thickness were measured and graphed.
Figures 18C, 18D, 18E:
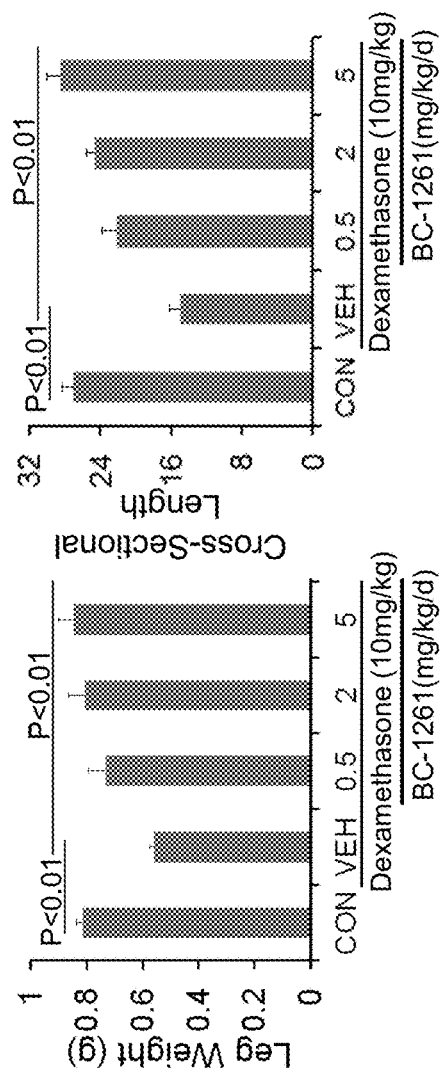
Figure 19:
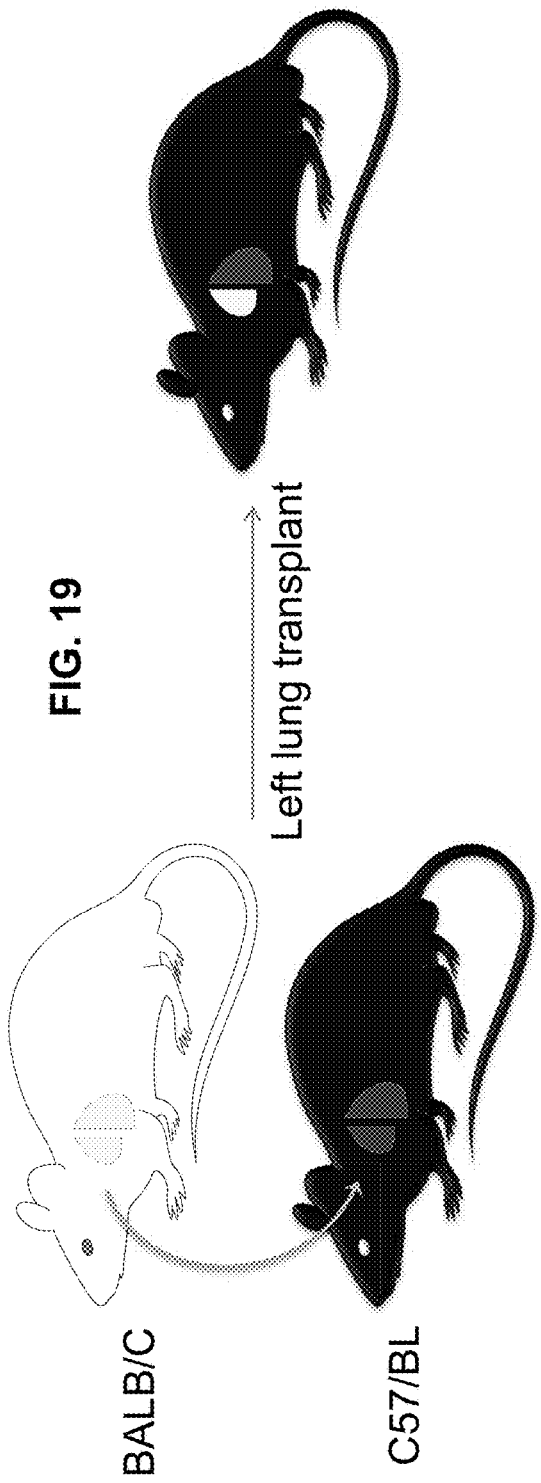
FIG. 19 shows lung transplant rejection model. H&E staining indicated that the severe infiltrates in rejected lung (vehicle group) compared to completely protected lung (BC-1261 group). BC-1261 effectively ameliorates neutrophilia infiltrates induced by lung transplant rejection.
Figure 19:
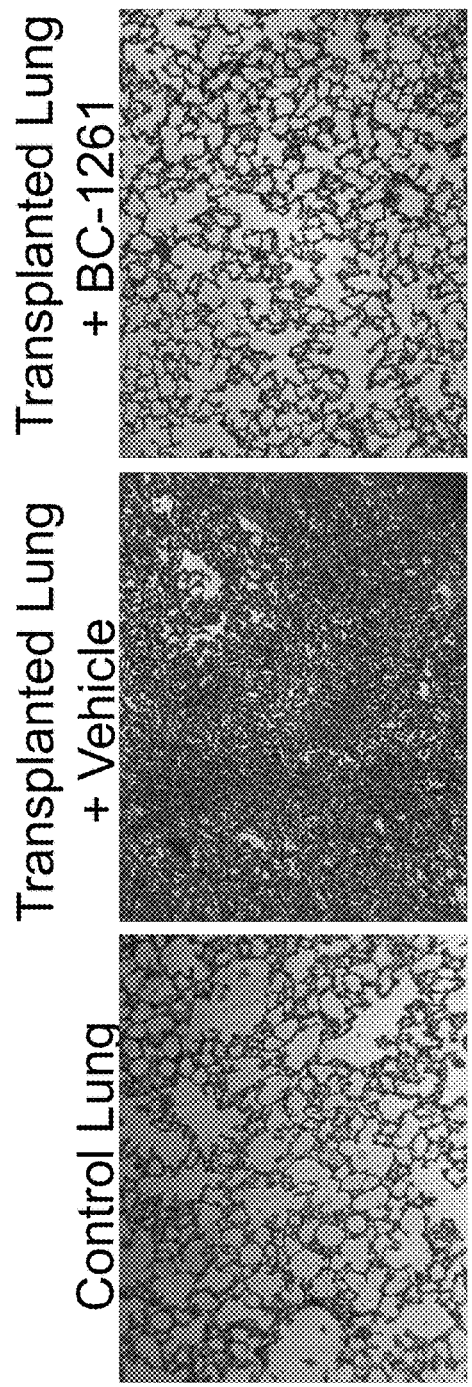

Mice treated with Compound 014 exhibited reduced lavage cell counts (FIG. 12A) and reduced lavage protein concentration (FIG. 12B), with measured levels near that of control mice. Additionally, mice treated with Compound 014 exhibited a reduction in lavage pro-inflammatory cytokine levels (FIG. 12C) compared to control mice that were not exposed to cigarette smoke.

Example 7

Psoriasis

Female BALB/c mice at 8 to 11 wk of age received a daily topical dose of 62.5 mg of commercially available IMQ cream (5%) (Aldara; 3M Pharmaceuticals) on the shaved back and the right ear for 5 or 6 consecutive days, translating in a daily dose of 3.125 mg of the active compound. Control mice were treated similarly with a control vehicle cream (Vaseline Lanette cream; Fagron). BC-1261 (also referred to herein as compound 014) were either given in drinking water or applied topically daily. To score the severity of inflammation of the back skin, an objective scoring system was developed based on the clinical Psoriasis Area and Severity Index (PASI), except that for the mouse model the affected skin area is not taken into account in the overall score. Erythema and scaling were scored independently on a scale from 0 to 4: 0, none; 1, slight; 2, moderate; 3, marked; 4, very marked. The level of erythema was scored using a scoring table with red taints. At day 7, mice were euthanized and spleens were removed for weight measuring. Skin and ear sample were also collected for H&E staining and epidermis thickness were measured and graphed. n=5-10 per group, *p<0.05.

The results shown in FIGS. 13-17 demonstrate that BC-1261 effectively ameliorates IMQ induced psoriasis in BALB/C mice. Specifically, BC-1261 reduces spleen weight, ear thickness, psoriasis index, and gross appearance in this model.

Example 8

Muscle Myopathy

C57BL mice were given daily i.p. injection of 0.1 ml of vehicle or Dexamethasone (10 mg/kg/d) for 14 days. Some mice were also given BC-1261 (also referred to herein as compound 014) in drinking water with estimated dose of 0.5, 2 and 5 mg/kg/d. Mice were then sacrificed and (tibialis anterior)TA muscle were removed, photographed (A), weighted (C), processed for H&E staining (B) and protein immunoblotting (E). Bar graphs in (D) showed the cross sectional length measurements from (B). n=4-8 PER GROUP, *P<0.01 versus Vehicle. #P<0.01 versus control.

Dexamethasone significantly increases FBXO3/TRAF6 protein levels in the TA muscle, induces a significant decrease in muscle weight and cross-sectional length. BC-1261 attenuates Dexamethasone-induced muscle atrophy in mice by degrading up-regulated TRAF6 protein. BC-1261 significantly ameliorates dexamethasone-induced tibialis anterior muscle loss even at the lost treatment dose at 0.5 mg/kg/d. Muscle wasting was also prevented indicated by the cross sectional measurements in the TA muscle H&E staining Example 9

Lung Transplant Acute Rejection Model

Left lung from BALB/C mouse was surgically removed and transplanted into C57/BL mouse. Mice were given vehicle or BC-1261 (5 mg/kg/d i.p. injection) for 2 days until fully recovered. After that, BC-1261 (also referred to herein as compound 014) was administered through drinking water (5 mg/kg/d) for additional 5 days. Mice were then sacrificed, and the transplanted lungs were removed for H&E staining. Note the severe infiltrates in rejected lung (vehicle group) compared to completely protected lung (BC-1261 group). BC-1261 effectively ameliorates neutrophilia infiltrates induced by lung transplant rejection.

Certain embodiments are described below with reference to the following numbered paragraphs:

1. A compound of general Formula I:

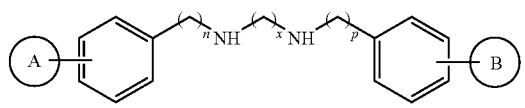

or salt, ester, solvate, hydrate, or prodrug thereof; wherein:
x is an integer from 1 to 10;
A and B are each, independently, $C_{3-7}$cycloalkyl, $C_{3-7}$cycloalkyl-$C_{1-6}$alkyl, $C_{3-7}$heterocycloalkyl, $C_{3-7}$heterocycloalkyl-$C_{1-6}$ alkyl, $C_{6-10}$aryl, $C_{6-10}$aryl-$C_{1-6}$alkyl, $C_{3-9}$heteroaryl, and $C_{3-9}$heteroaryl-$C_{1-6}$alkyl; and
n and p are each, independently, integers from 1 to 10.

2. The compound of paragraph 1, wherein at least one of A and B is substituted with at least one substituent independently selected the group consisting of halogen, $C_{1-6}$alkyl, $C_{1-6}$haloalkyl, hydroxyl, $C_{1-6}$alkoxy, $C_{1-6}$haloalkoxy, amino, $C_{1-6}$alkylamino, or di-$C_{1-6}$alkylamino.

3. The compound of paragraph 1, wherein A and B are the same.

4. The compound of paragraph 1, wherein A and B are in para configuration.

5. The compound of paragraph 1, wherein A and B are each, independently selected from the group consisting of cyclohexyl, phenyl, 6-membered heteroaryl, 6-membered heterocycloalkyl, cyclopentyl, cyclopentene, cyclopentadiene, 5-membered heteroaryl, 5-membered heterocyloalkyl.

6. The compound of paragraph 1, wherein A and B are each, independently, selected from the group consisting of pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, pyranyl, thiopyranyl, piperidinyl, morpholinyl, thiomorpholinyl, piperazinyl, and triazinyl.

7. The compound of paragraph 1, wherein A and B are each, independently, selected from the group consisting of imidazolyl, pyridyl, pyrazolyl, oxadiazolyl and pyrimidinyl.

8. The compound of paragraph 1, wherein A and B are each, independently, selected from the group consisting of:

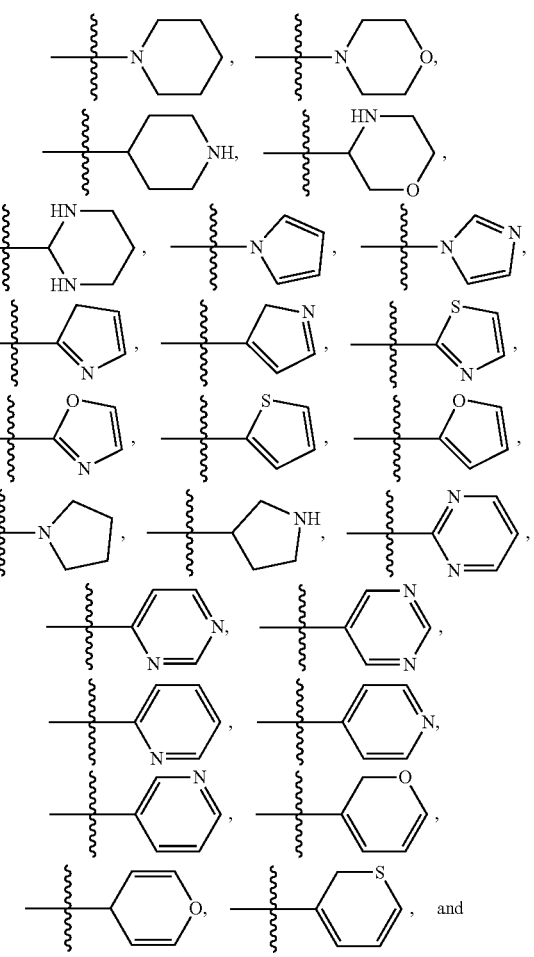

-continued

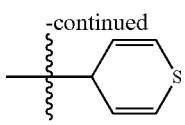

9. The compound of paragraph 1, wherein the compound is of Formula Ia:

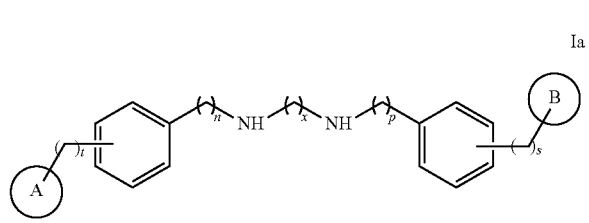

Ia or salt, ester, solvate, hydrate, or prodrug thereof; wherein:
x is an integer from 1 to 10;
A and B are each, independently, $C_{3-7}$cycloalkyl, $C_{3-7}$cycloalkyl-$C_{1-6}$alkyl, $C_{3-7}$heterocycloalkyl, $C_{3-7}$heterocycloalkyl-$C_{1-6}$ alkyl, $C_{6-10}$aryl, C6-10aryl-$C_{1-6}$alkyl, $C_{3-9}$heteroaryl, and $C_{3-9}$heteroaryl-$C_{1-6}$alkyl;
n and p are each, independently, integers from 1 to 10; and
s and t are each, independently, integers from 1 to 5

10. A pharmaceutical composition comprising:
a compound of general Formula I:

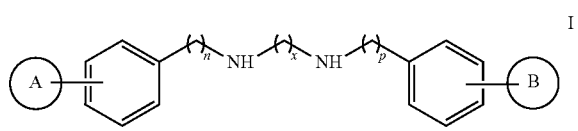

I or salt, ester, solvate, hydrate, or prodrug thereof; wherein:
x is an integer from 1 to 10;
A and B are each, independently, $C_{3-7}$cycloalkyl, $C_{3-7}$cycloalkyl-$C_{1-6}$alkyl, $C_{3-7}$heterocycloalkyl, $C_{3-7}$heterocycloalkyl-$C_{1-6}$alkyl, $C_{6-10}$aryl, $C_{6-10}$aryl-$C_{1-6}$alkyl, $C_{3-9}$ heteroaryl, and $C_{3-9}$heteroaryl-$C_{1-6}$alkyl; and
n and p are each, independently, integers from 1 to 10;
a pharmaceutically acceptable carrier, excipient, or diluent.

11. The pharmaceutical composition of paragraph 10, wherein A and B are each, independently, selected from the group consisting of pyrrolyl, H-pyrrolyl, pyrrolinyl, pyrrolidinyl, oxazolyl, oxadiazolyl, (including 1,2,3; 1,2, 4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, pyranyl, thiopyranyl, piperidinyl, morpholinyl, thiomorpholinyl, piperazinyl, and triazinyl.

12. The pharmaceutical composition of paragraph 10, wherein A and B are each, independently, selected from the group consisting of imidazolyl, pyridyl, pyrazolyl, oxadiazolyl and pyrimidinyl.

13. The pharmaceutical composition of paragraph 10, wherein the carrier is selected from the group consisting of carrier water, ethanol, polyol, glycerol, propylene glycol, liquid polyethylene glycol, vegetable oils, nut oils, and mixtures thereof.

14. The pharmaceutical composition of paragraph 10, further comprising at least one flavoring agent, binding agent, lubricant, disintegrant, surface modifying agent, surfactant, suspending agent, stabilizing agent, fillers, glidant, compression aid, disintegrating agent, encapsulating material, or combinations thereof.

15. The pharmaceutical composition of paragraph 10, further comprising at least one anti-inflammatory agents, antimicrobial agents, matrix metalloprotease inhibitors, lipoxygenase inhibitors, cytokine antagonists, immunosuppressants, anti-cancer agents, anti-viral agents, cytokines, growth factors, immunomodulators, prostaglandins, anti-vascular hyperproliferation compounds, and combinations thereof.

16. The pharmaceutical composition of paragraph 10, wherein the compound of Formula I or salt, ester, solvate, hydrate, or prodrug thereof comprises about 15 wt. % to about 95 wt. % of a total weight of the pharmaceutical composition.

17. The pharmaceutical composition of paragraph 10, wherein the pharmaceutical composition is in unit dose form.

18. The pharmaceutical composition of paragraph 17, wherein each unit dose comprises about 0.5 mg to about 500 mg of the compound of Formula I or salt, ester, solvate, hydrate, or prodrug thereof.

19. A method for treating a respiratory injury or disease comprising:
administering to a patient in need of treatment a pharmaceutical composition comprising a compound of general Formula I:

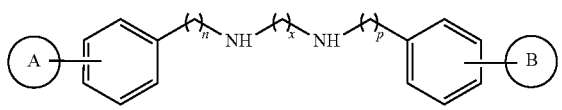

I or salt, ester, solvate, hydrate, or prodrug thereof; wherein:
x is an integer from 1 to 10;
A and B are each, independently, $C_{3-7}$cycloalkyl, $C_{3-7}$cycloalkyl-$C_{1-6}$alkyl, $C_{3-7}$heterocycloalkyl, $C_{3-7}$heterocycloalkyl-$C_{1-6}$ alkyl, $C_{6-10}$aryl, $C_{6-10}$aryl-$C_{1-6}$alkyl, $C_{3-9}$heteroaryl, and $C_{3-9}$heteroaryl-$C_{1-6}$alkyl; and
n and p are each, independently, integers from 1 to 10; and
a pharmaceutically acceptable carrier, excipient, or diluent.

20. The method of paragraph 19, wherein A and B are each, independently, selected from the group consisting of pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, pyranyl, thiopyranyl, piperidinyl, morpholinyl, thiomorpholinyl, piperazinyl, and triazinyl.

21. The method of paragraph 19, wherein A and B are each, independently, selected from the group consisting of imidazolyl, pyridyl, pyrazolyl, oxadiazolyl and pyrimidinyl.

22. The method of paragraph 19, wherein the compound of Formula I or salt, ester, solvate, hydrate, or prodrug thereof is administered in an effective amount.
23. The method of paragraph 23, wherein an effective amount comprises from about 0.5 mg to about 500 mg of the compound of Formula I or salt, ester, solvate, hydrate, or prodrug thereof.
24. The method of paragraph 23, wherein an effective amount comprises about 0.5 mg/kg to about 500 mg/kg per kg of patient body weight of the compound of Formula I or salt, ester, solvate, hydrate, or prodrug thereof.
25. The method of paragraph 19, wherein administering comprises oral administration, administration via implants, parenteral injection, intravenous injection, intraperitoneal injection, subcutaneous injection, bolus injection, infusion, rectal administration, vaginal administration, transdermal administration, inhalation, and combinations thereof.
26. The method of paragraph 19, further comprising administrating at least one anti-inflammatory agents, antimicrobial agents, matrix metalloprotease inhibitors, lipoxygenase inhibitors, cytokine antagonists, immunosuppressants, anti-cancer agents, anti-viral agents, cytokines, growth factors, immunomodulators, prostaglandins, anti-vascular hyperproliferation compounds, and combinations thereof.
27. The method of paragraph 19, wherein the respiratory injury or disease is selected from the group consisting of acute and chronic bronchitis, emphysema, respiratory infections (pneumonia, pleurisy), flu (including influenza), post-lung transplant rejection including acute and chronic rejection and bronchiolitis obliterans, acute lung injury or the acute respiratory distress syndrome, pulmonary fibrosis, asthma, cystic fibrosis, and bronchiectasis.
28. The method of paragraph 19, wherein the respiratory injury or disease is acute or chronic bronchitis.
29. A compound having the structure:

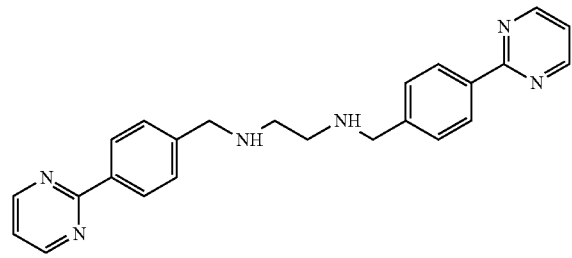 [SMILES: c1cnc(-c2ccc(CNCCNCc3ccc(-c4ncccn4)cc3)cc2)nc1]

30. A composition comprising a compound having the structure:

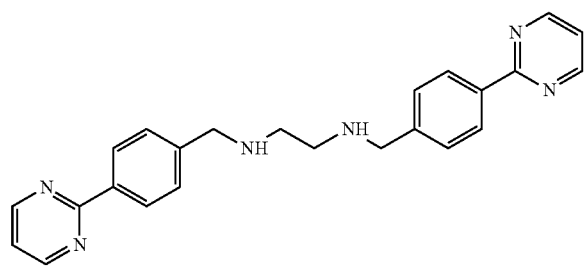 [SMILES: c1cnc(-c2ccc(CNCCNCc3ccc(-c4ncccn4)cc3)cc2)nc1]

31. A pharmaceutical composition comprising:
   a compound having the structure:

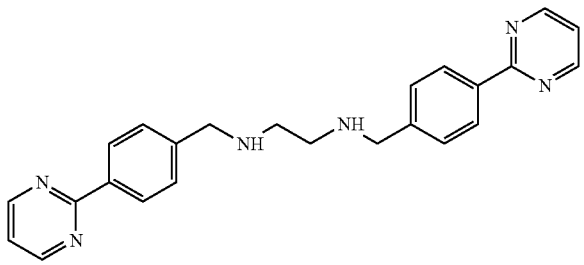 [SMILES: c1cnc(-c2ccc(CNCCNCc3ccc(-c4ncccn4)cc3)cc2)nc1]

or salt, ester, solvate, hydrate, or prodrug thereof, and
   a pharmaceutically acceptable carrier, excipient, or diluent.
32. The pharmaceutical composition of paragraph 31, wherein the carrier is selected from the group consisting of carrier water, ethanol, polyol, glycerol, propylene glycol, liquid polyethylene glycol, vegetable oils, nut oils, and mixtures thereof.
33. The pharmaceutical composition of paragraph 31, further comprising at least one flavoring agent, binding agent, lubricant, disintegrant, surface modifying agent, surfactant, suspending agent, stabilizing agent, fillers, glidant, compression aid, disintegrating agent, encapsulating material, or combinations thereof.
34. The pharmaceutical composition of paragraph 31, further comprising at least one anti-inflammatory agents, antimicrobial agents, matrix metalloprotease inhibitors, lipoxygenase inhibitors, cytokine antagonists, immunosuppressants, anti-cancer agents, anti-viral agents, cytokines, growth factors, immunomodulators, prostaglandins, anti-vascular hyperproliferation compounds, and combinations thereof.
35. The pharmaceutical composition of paragraph 31, wherein the compound having the structure:

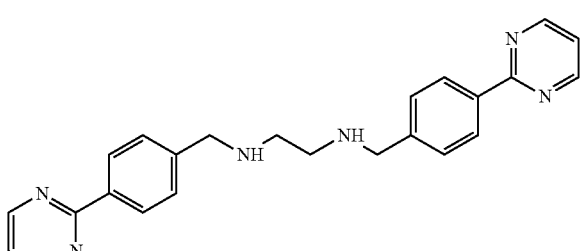

or salt, ester, solvate, hydrate, or prodrug thereof comprises about 15 wt. % to about 95 wt. % of a total weight of the pharmaceutical composition.
36. The pharmaceutical composition of paragraph 31, wherein the pharmaceutical composition is in unit dose form.
37. The pharmaceutical composition of paragraph 36, wherein each unit dose comprises about 0.5 mg to about 500 mg of the compound having the structure:

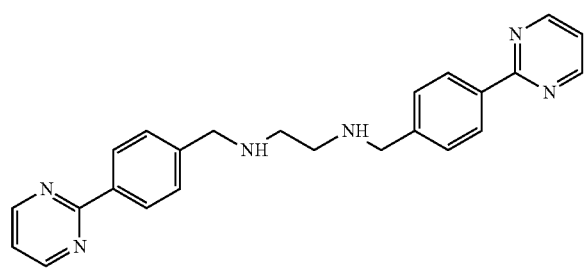 [SMILES: c1cnc(-c2ccc(CNCCNCc3ccc(-c4ncccn4)cc3)cc2)nc1]

or salt, ester, solvate, hydrate, or prodrug thereof.

38. A method for treating a respiratory injury or disease comprising:
administering to a patient in need of treatment a pharmaceutical composition comprising a compound having the structure:

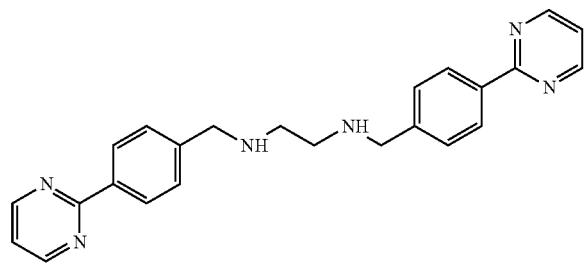 [SMILES: c1cnc(-c2ccc(CNCCNCc3ccc(-c4ncccn4)cc3)cc2)nc1]

or salt, ester, solvate, hydrate, or prodrug thereof; and
a pharmaceutically acceptable carrier, excipient, or diluent.

39. The method of paragraph 38, wherein the compound having the structure:

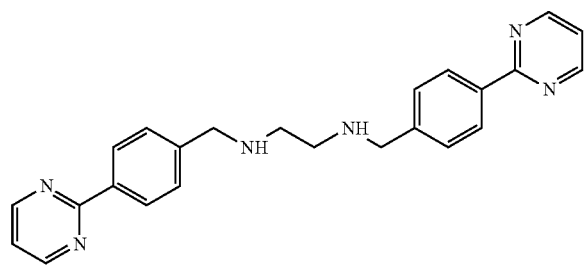 [SMILES: c1cnc(-c2ccc(CNCCNCc3ccc(-c4ncccn4)cc3)cc2)nc1]

or salt, ester, solvate, hydrate, or prodrug thereof is administered in an effective amount.

40. The method of paragraph 39, wherein an effective amount comprises from about 0.5 mg to about 500 mg of the compound having the structure:

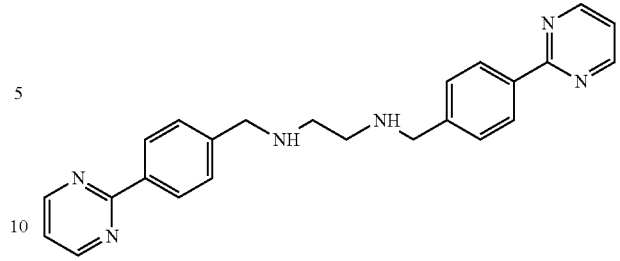

or salt, ester, solvate, hydrate, or prodrug thereof.

41. The method of paragraph 39, wherein an effective amount comprises about 0.5 mg/kg to about 500 mg/kg per kg of patient body weight of compound having the structure:

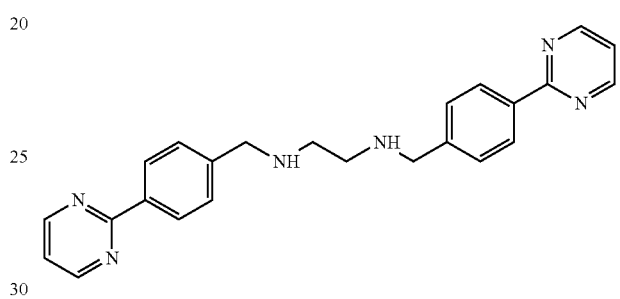

or salt, ester, solvate, hydrate, or prodrug thereof.

42. The method of paragraph 38, wherein administering comprises oral administration, administration via implants, parenteral injection, intravenous injection, intraperitoneal injection, subcutaneous injection, bolus injection, infusion, rectal administration, vaginal administration, transdermal administration, inhalation, and combinations thereof.

43. The method of paragraph 38, wherein the pharmaceutical composition further comprises a carrier selected from the group consisting of carrier water, ethanol, polyol, glycerol, propylene glycol, liquid polyethylene glycol, vegetable oils, nut oils, and mixtures thereof.

44. The method of paragraph 38, wherein the pharmaceutical composition further comprises at least one flavoring agent, binding agent, lubricant, disintegrant, surface modifying agent, surfactant, suspending agent, stabilizing agent, fillers, glidant, compression aid, disintegrating agent, encapsulating material, or combinations thereof.

45. The method of paragraph 38, further comprising administrating at least one anti-inflammatory agents, antimicrobial agents, matrix metalloprotease inhibitors, lipoxygenase inhibitors, cytokine antagonists, immunosuppressants, anti-cancer agents, anti-viral agents, cytokines, growth factors, immunomodulators, prostaglandins, anti-vascular hyperproliferation compounds, and combinations thereof.

46. The method of paragraph 38, wherein the respiratory injury or disease is selected from the group consisting of acute and chronic bronchitis, emphysema, respiratory infections (pneumonia, pleurisy), flu (including influenza), post-lung transplant rejection including acute and chronic rejection and bronchiolitis obliterans, acute lung injury or the acute respiratory distress syndrome, pulmonary fibrosis, asthma, cystic fibrosis, and bronchiectasis.

47. The method of paragraph 38, wherein the respiratory injury or disease is acute or chronic bronchitis.

In view of the many possible embodiments to which the principles of the disclosed compounds, compositions and methods may be applied, it should be recognized that the illustrated embodiments are only preferred examples of the invention and should not be taken as limiting the scope of the invention.

What is claimed is:

1. A method for treating a respiratory injury or disease comprising:
   administering to a patient in need of treatment a pharmaceutical composition comprising a compound, or a pharmaceutically acceptable salt thereof, having a structure of formula V:

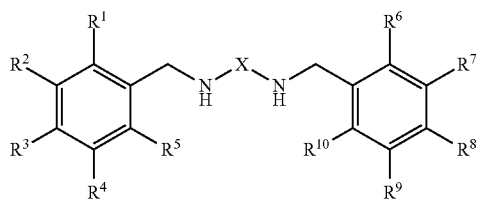

wherein X is —CH$_2$CH$_2$—; and
   R$^1$-R$^{10}$ are each individually H, optionally-substituted alkyl, optionally-substituted alkoxy, optionally-substituted aryl, optionally-substituted cycloalkyl, optionally-substituted heterocyclic, halogen, amino, or hydroxy; and
   a pharmaceutically acceptable carrier, excipient, or diluent,
   wherein the respiratory injury or disease is selected from the group consisting of acute and chronic bronchitis, emphysema, respiratory infections, flu, post-lung transplant rejection including acute and chronic rejection and bronchiolitis obliterans, acute lung injury or the acute respiratory distress syndrome, and bronchiectasis.

2. The method of claim 1, wherein the respiratory injury or disease is acute or chronic bronchitis.

3. The method of claim 1, wherein the composition is administered via intratracheal delivery.

4. The method of claim 1, wherein the composition is administered via inhalation.

5. The method of claim 1, wherein the composition is co-administered with a bronchodilator, a corticosteroid, or a combination thereof.

6. The method of claim 1, wherein R$^3$ and R$^8$ are each a 6-membered N-heterocycle.

7. The method of claim 6, wherein R$^1$, R$^2$, R$^4$, R$^5$, R$^6$, R$^7$, R$^9$ and R$^{10}$ are each individually H or halogen.

8. A method for treating a respiratory infection comprising:
   administering to a patient in need of treatment a pharmaceutical composition comprising a compound, or a pharmaceutically acceptable salt thereof, having a structure of formula V:

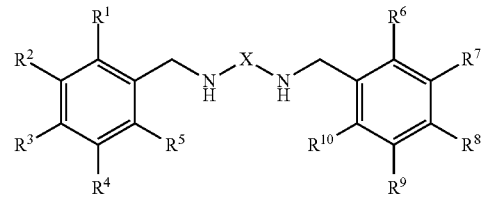

wherein X is a divalent or tetravalent linking moiety; and
   R$^1$-R$^{10}$ are each individually H, optionally-substituted alkyl, optionally-substituted alkoxy, optionally-substituted aryl, optionally-substituted cycloalkyl, optionally-substituted heterocyclic, halogen, amino, or hydroxy, provided at least one of R$_3$ or R$_8$ is an optionally-substituted heterocyclic; and
   a pharmaceutically acceptable carrier, excipient, or diluent.

9. The method of claim 8, wherein the respiratory injury or disease is acute or chronic bronchitis.

10. The method of claim 8, wherein the composition is administered via intratracheal delivery.

11. The method of claim 8, wherein the composition is administered via inhalation.

12. The method of claim 8, wherein the composition is co-administered with a bronchodilator, a corticosteroid, or a combination thereof.

13. The method of claim 8, wherein at least one of R$^3$ or R$^8$ is an N-heterocyclic.

14. The method of claim 8, wherein R$^3$ is an N-heterocyclic and R$^8$ is an N-heterocycle.

15. The method of claim 8, wherein R$^3$ and R$^8$ are each a 6-membered N-heterocycle.

16. The method of claim 15, wherein R$^1$, R$^2$, R$^4$, R$^5$, R$^6$, R$^7$, R$^9$ and R$^{10}$ are each individually H or halogen.

17. A method for treating a respiratory injury or disease comprising:
   administering to a patient in need of treatment a pharmaceutical composition comprising a compound, or a pharmaceutically acceptable salt thereof, having a structure of

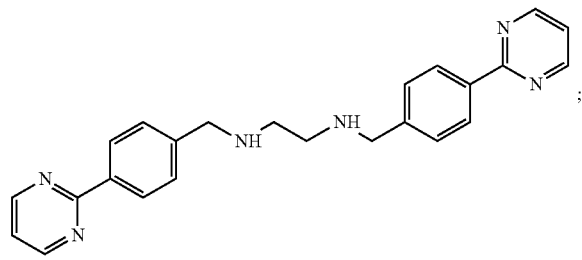 [SMILES: c1cnc(-c2ccc(CNCCNCc3ccc(-c4ncccn4)cc3)cc2)nc1]

and a pharmaceutically acceptable carrier, excipient, or diluent,
   wherein the respiratory injury or disease is selected from the group consisting of acute and chronic bronchitis, emphysema, respiratory infections, flu, post-lung transplant rejection including acute and chronic rejection and bronchiolitis obliterans, acute lung injury or the acute respiratory distress syndrome, and bronchiectasis.

18. The method of claim 17, wherein the respiratory injury or disease is acute or chronic bronchitis.

19. The method of claim 17, wherein the composition is administered via intratracheal delivery.

20. The method of claim 17, wherein the composition is administered via inhalation.

21. The method of claim 17, wherein the composition is co-administered with a bronchodilator, a corticosteroid, or a combination thereof.

* * * * *

UNITED STATES PATENT AND TRADEMARK OFFICE
CERTIFICATE OF CORRECTION

PATENT NO. : 10,092,526 B2
APPLICATION NO. : 15/816963
DATED : October 9, 2018
INVENTOR(S) : Chen et al.

Page 1 of 1

It is certified that error appears in the above-identified patent and that said Letters Patent is hereby corrected as shown below:

In the Specification

Column 1, Lines 23-26, Acknowledgement of Government Support:
"This invention was made with government support under grants HL068135, HL081784, HL096376, and HL098174 awarded by the National Institutes of Health. The government has certain rights in the invention."

Should read:
--This invention was made with government support under HL068135, HL081784, HL096376, HL097376, HL098174, and HL116472 awarded by the National Institutes of Health. The government has certain rights in the invention.--

Signed and Sealed this
Eighth Day of July, 2025

Coke Morgan Stewart
*Acting Director of the United States Patent and Trademark Office*